US009746415B2

(12) United States Patent
Holm et al.

(10) Patent No.: US 9,746,415 B2
(45) Date of Patent: Aug. 29, 2017

(54) SAMPLE HOLDER, DETECTOR MASK, AND SCOPE SYSTEM

(71) Applicant: THE UNITED STATES OF AMERICA, AS REPRESENTED BY THE SECRETARY OF COMMERCE, Washington, DC (US)

(72) Inventors: Jason D. Holm, Louisville, CO (US); Robert R. Keller, Louisville, CO (US); Katherine P. Rice, Fitchburg, WI (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/403,931

(22) Filed: Jan. 11, 2017

(65) Prior Publication Data

US 2017/0199113 A1 Jul. 13, 2017

Related U.S. Application Data

(60) Provisional application No. 62/277,640, filed on Jan. 12, 2016.

(51) Int. Cl.

*G02B 21/36* (2006.01)
*G01N 3/02* (2006.01)
*G01N 21/00* (2006.01)
*G01N 21/03* (2006.01)
*G01N 3/04* (2006.01)

(52) U.S. Cl.

CPC ............... *G01N 21/03* (2013.01); *G01N 3/04* (2013.01); *G02B 21/361* (2013.01)

(58) Field of Classification Search

CPC ...... G02B 21/361; G02B 21/34; G02B 21/06; G02B 27/56; G02B 21/02; G02B 21/26; G02B 7/003; G01N 3/04; G01N 2203/0411; G01N 21/03

See application file for complete search history.

(56) References Cited

U.S. PATENT DOCUMENTS

| | | | | |
|---|---|---|---|---|
| 7,677,110 B2 * | 3/2010 | Perez Blanco | .......... | G01N 3/08 73/826 |
| 7,739,919 B2 * | 6/2010 | Lemmer | .................. | G01N 3/04 73/857 |
| 7,827,868 B2 * | 11/2010 | Lindeman | ................ | G01N 3/04 73/760 |
| 8,371,182 B1 * | 2/2013 | Israelachvili | ............ | G01N 3/04 356/244 |
| 8,586,922 B2 | 11/2013 | Nagaoki et al. | | |

(Continued)

*Primary Examiner* — Sang Nguyen
(74) *Attorney, Agent, or Firm* — Toby D. Hain

(57) ABSTRACT

A detector mask transmits selectively a plurality of probe particles to a particle detector, the detector mask includes: a plate including a plate wall disposed in the plate and enclosing a transmission orifice arranged in a transmission profile to: transmit probe particles having a trajectory coincident with the transmission orifice, block probe particles having a trajectory external to the transmission orifice, and form a probe particle beam comprising the probe particles transmitted by the transmission orifice to the particle detector, wherein the transmission profile includes a sector, a semi-circle, an annular sector, or a combination including at least one of the foregoing first transmission profiles.

10 Claims, 47 Drawing Sheets

(56) References Cited

U.S. PATENT DOCUMENTS

| | | | | |
|---|---|---|---|---|
| 2002/0166387 | A1* | 11/2002 | Grote | G01N 3/04<br>73/857 |
| 2013/0193970 | A1* | 8/2013 | Alexson | G01N 24/08<br>324/309 |
| 2017/0023611 | A1* | 1/2017 | Martinez-Martin | G01N 21/65 |
| 2017/0082846 | A1* | 3/2017 | Rowlette | G02B 21/361 |

* cited by examiner

100

(A)

(B)

(C)

(A)

(B)

(A)

(B)

(A)

(B)

(A)

(B)

(A)

(B)

(A)

(b)

SAMPLE HOLDER, DETECTOR MASK, AND SCOPE SYSTEM

CROSS REFERENCE TO RELATED APPLICATIONS

This application claims the benefit of U.S. Provisional Patent Application Ser. No. 62/277,640, filed Jan. 12, 2016, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is a detector mask to transmit selectively a plurality of probe particles to a particle detector, the detector mask comprising: a plate comprising a plate wall disposed in the plate and enclosing a transmission orifice arranged in a transmission profile to: transmit probe particles having a trajectory coincident with the transmission orifice, block probe particles having a trajectory external to the transmission orifice, and form a probe particle beam comprising the probe particles transmitted by the transmission orifice to the particle detector, wherein the transmission profile comprises a sector, a semi-circle, an annular sector, or a combination comprising at least one of the foregoing first transmission profiles.

Further disclosed is a detector mask to transmit selectively a plurality of probe particles to a particle detector, the detector mask comprising: a first plate comprising a first plate wall disposed in the first plate and enclosing a first transmission orifice arranged in a first transmission profile to: transmit probe particles having a trajectory coincident with the first transmission orifice, block probe particles having a trajectory external to the first transmission orifice, and form a first probe particle beam comprising the probe particles transmitted by the first transmission orifice; and a second plate comprising a second plate wall disposed in the second plate and enclosing a second transmission orifice arranged in a second transmission profile to: receive the first probe particle beam, transmit probe particles in the first probe particle beam having a trajectory coincident with the second transmission orifice, block probe particles in the first probe particle beam having a trajectory external to the second transmission orifice, and form a second probe particle beam comprising the probe particles transmitted by the second transmission orifice, the first plate and the second plate arranged in a stack in the detector mask such that the first transmission profile and the second transmission profile in combination provide a mask transmission profile through which the probe particles are transmitted to the particle detector.

Also disclosed is a sample holder to hold a sample for microscopy or spectroscopy comprising: a basal member; an inferior cantilever arm disposed on the basal member to receive the sample and comprising: a first mount end proximately attached to the basal member; and a first free end disposed distal to and protruding away from the basal member, the first free end being flexible relative to the first mount end; and a superior cantilever arm disposed on the basal member opposing the inferior cantilever arm such that the inferior cantilever arm is interposed between the basal member and the superior cantilever arm, the superior cantilever arm comprising: a second mount end proximately attached to the basal member; a second free end disposed distal to and protruding away from the basal member, the second free end being flexible relative to the second mount end; and a curved intermediate armlet interposed between the second mount end and the second free end, the curved intermediate armlet comprising a depressible crook in which the depressible crook is in a relaxed position when not depressed, and the depressible crook is in a stretched position when depressed, wherein the first free end and the second free end opposingly engage and retain the sample between the first free end and the second free end when the depressible crook is in the relaxed position, and the first free end is spaced apart from the second free end to release or to receive the sample between the first free end and the second free end when the depressible crook is in the stretched position.

Further also disclosed is a scope system comprising: the sample holder to receive the sample and to expose the sample to a plurality of source particles such that the probe particles are communicated from the sample in response to receipt of the source particles; and either of the detector masks described above, wherein the first plate of the detector mask receives the probe particles from the sample held by the sample holder.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a sample holder provides holding a sample via opposing cantilever arms to engage and clamp the sample into an arbitrary position with respect to a particle source or particle detector. The sample holder supports the sample between two flexible cantilever arms and aligns the sample with an optic axis of a scope, e.g., a microscope of spectroscope. Advantageously, one cantilever arm is flat, and the other cantilever arm includes a crook that provides tool-free clamping of the sample. Beneficially, the sample can be edge-clamped (e.g., for self-supporting samples) or fully supported between the cantilever arms. Moreover, the cantilever arms are flexible so damage to components of the scope such as a particle detector or particle source is avoided, mitigated, or unlikely. Also, the sample holder is easy to use and fabricate, cost effective to produce and maintain, and robust with respect to damage of the scope were an accidental collision to occur between the cantilever arms of the sample holder and other components of the scope. Unexpectedly, the sample holder positions the sample in arbitrary any orientation in a space between, e.g., a pole piece of an electron source and an electron detector in an electron microscope.

It also has been discovered that a detector mask provides fine control or coarse control over acceptance angle of the particle detector. Further, the detector mask provides an imaging mode such as a bright field, dark field, or a combination of those imaging modes in an imaging device such as a light microscope, electron microscope, ion microscope, and the like.

A combination of the sample holder and the detector mask are included in a scope system for positioning a sample with angularly-selective transmission and acceptance angle control for improved transmission imaging, e.g., in scanning transmission electron microscopy.

Figure 1:
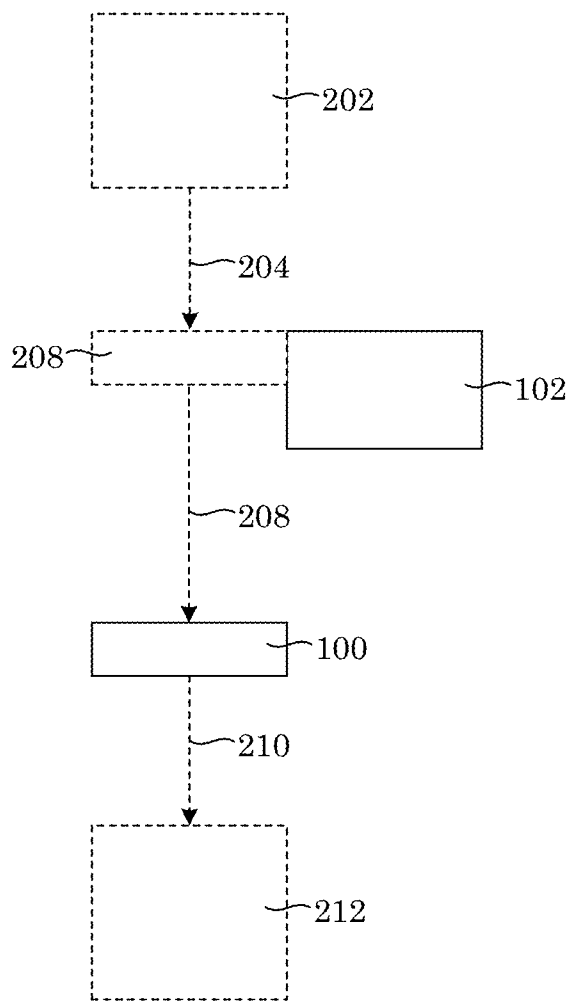
FIG. 1 shows a scope system.

In an embodiment, with reference to FIG. 1, scope system 200 includes sample holder 102 on which sample 206 is disposed to expose sample 206 to a plurality of source particles 204 from particle source 202 such that probe particles 208 are communicated from sample 206 in response to receipt of source particles 204. Additionally, detector mask 100 receives probe particles 208 from sample 206 held by sample holder 102 and communicates probe particle beam 210 to particle detector 212. Here, probe particle beam 210 includes probe particles transmitted through detector mask 100.

Figure 2:
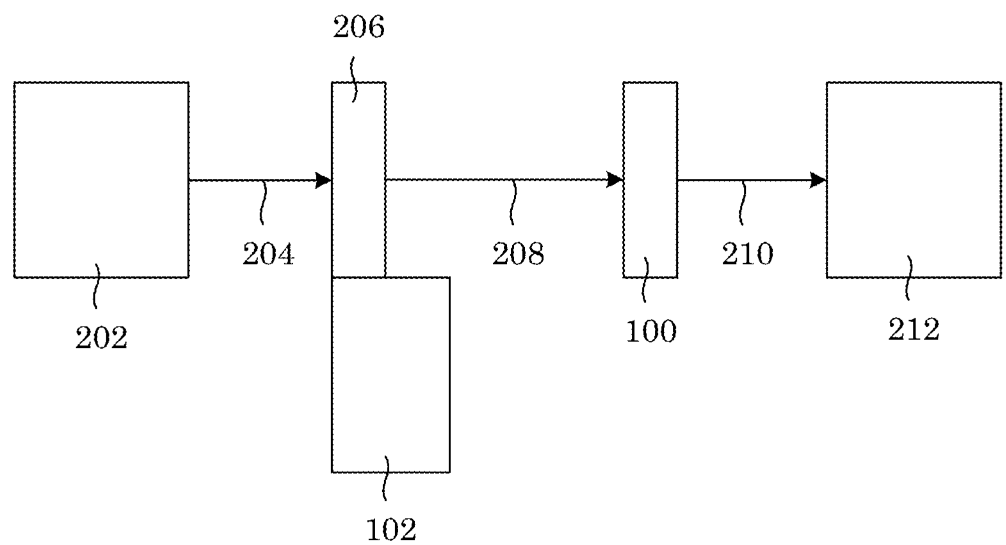
FIG. 2 shows a scope system.

According to an embodiment, with reference to FIG. 2, scope system 200 is a spectroscope for spectroscopy or spectrometry that includes laser 202 that produces source photons 204 as source particles that are received by sample 206 held by sample holder 102. In response to receipt of photons 204, probe particles 208 (e.g., ions (atomic, molecular, or a combination thereof), photons, neutral atoms or neutral molecules, electrons, or a combination thereof) are communicated from sample 206 to detector mask 100 that selectively transmits certain probe particles to detector 212 as probe particle beam 210. Here, detector 212 can be a photon detector, ion detector, position sensitive detector, or electron detector based on whether probe particles in probe particle beam 210 are ions, photons, neutral atoms, neutral molecules, or electrons.

Figure 3:
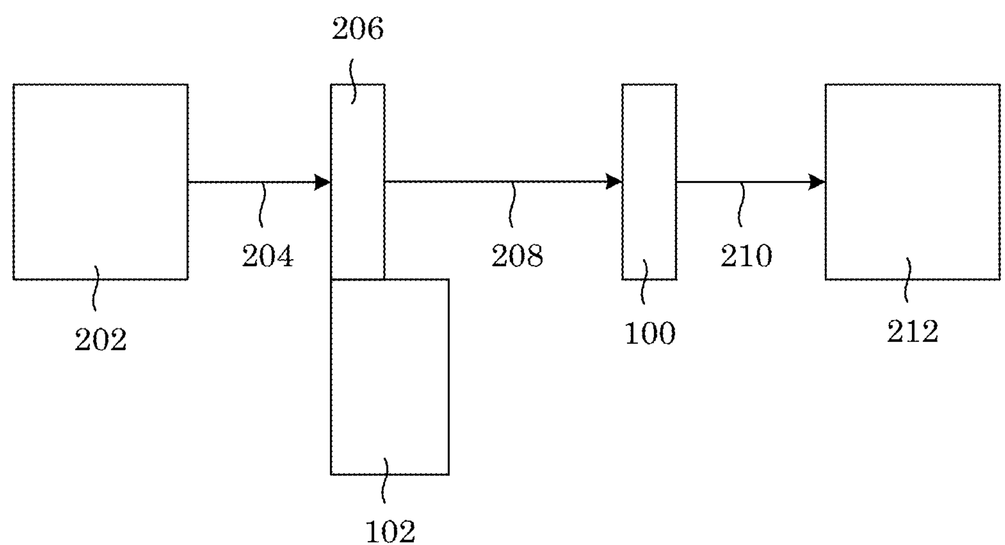
FIG. 3 shows a scope system.

According to an embodiment, with reference to FIG. 3, scope system 200 is a microscope for microscopy or spectroscopy that includes electron source 202 that produces source electrons 204 as source particles that are received by sample 206 held by sample holder 102. In response to receipt of source electrons 204, probe particles 208 (e.g., ions, electrons, or a combination thereof) are communicated from sample 206 to detector mask 100 that selectively transmits certain probe particles to detector 212 as probe particle beam 210. Here, detector 212 can be an ion detector or electron detector based on whether probe particles in probe particle beam 210 are ions or electrons.

Figure 4:
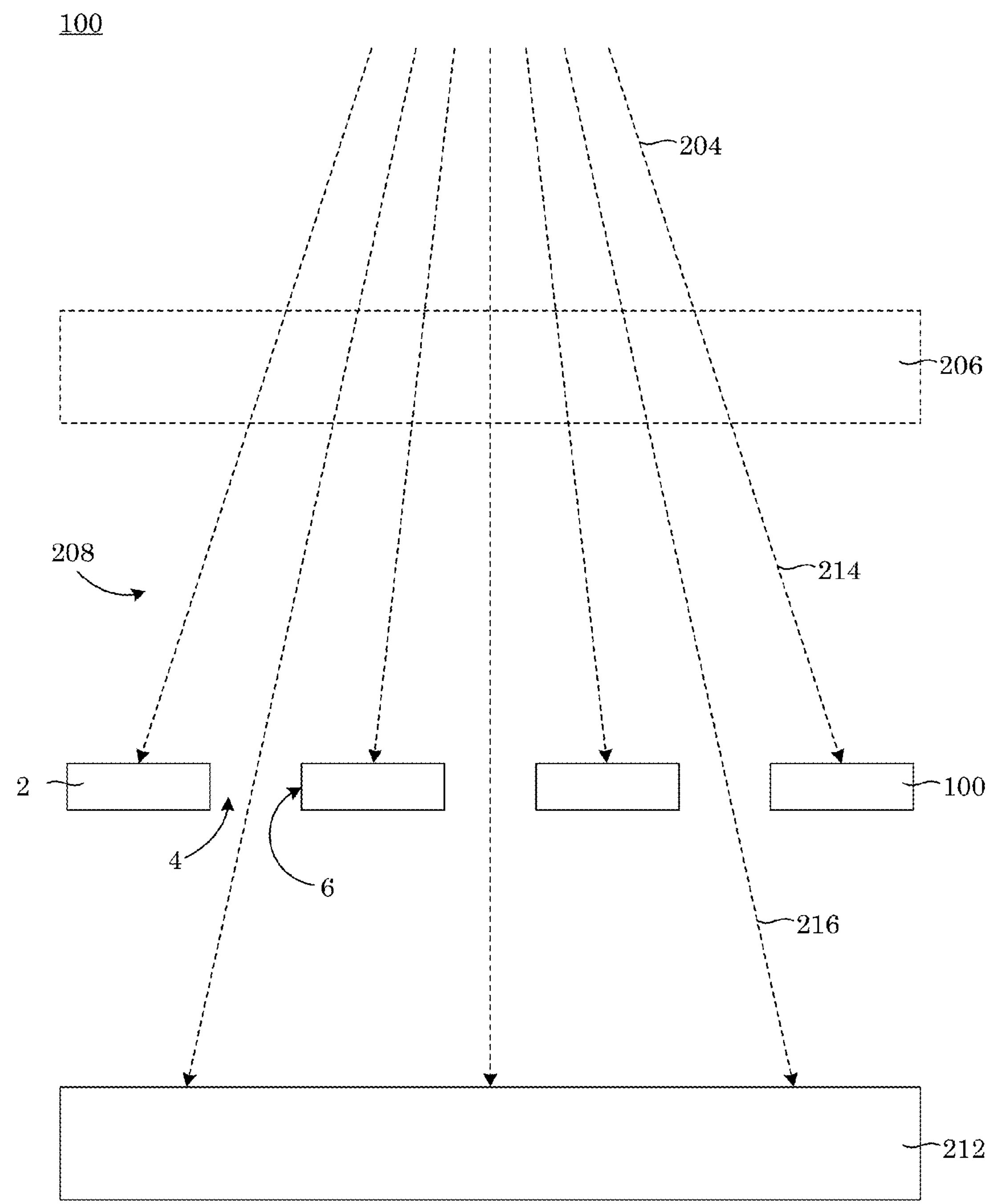
FIG. 4 shows a cross-section of a detector mask.
Figure 5:
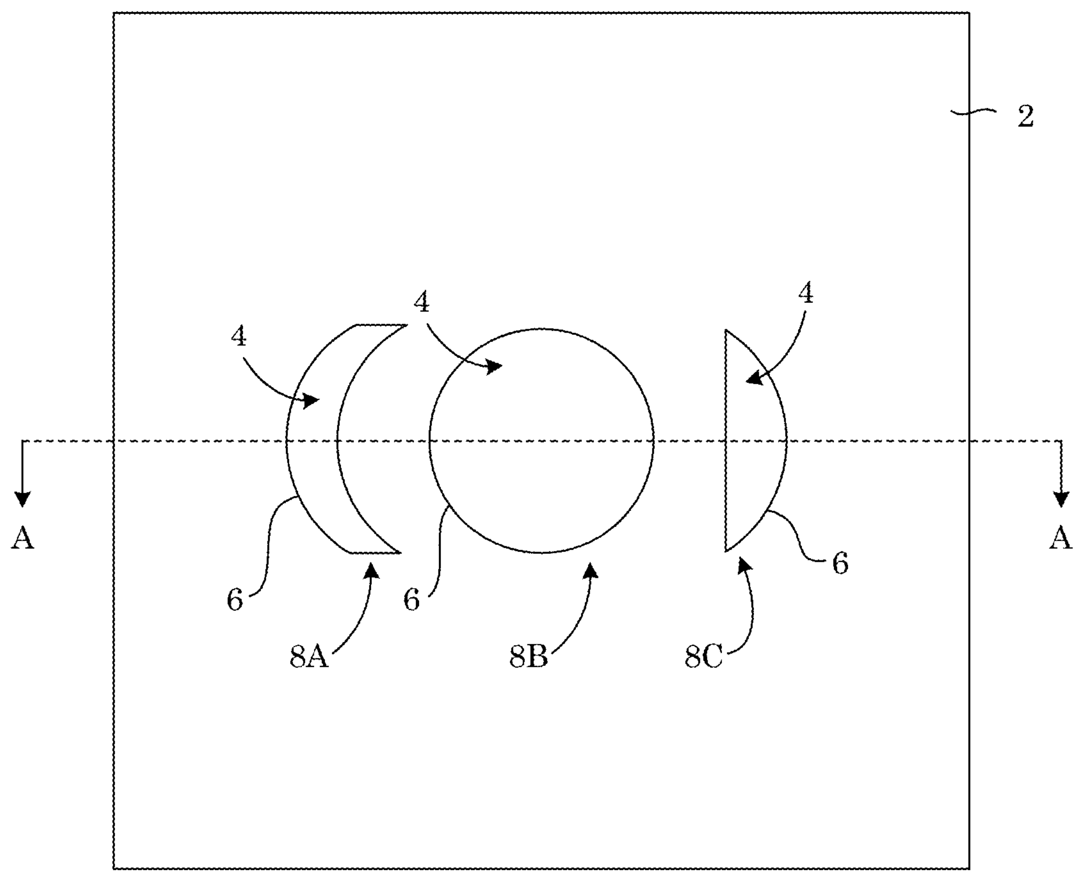
FIG. 5 shows a top view of a detector mask.

In an embodiment, with reference to FIG. 4 (cross-section along line A-A shown in FIG. 5) and FIG. 5 (top view), detector mask 100 transmits selectively a plurality of probe particles 216 to particle detector 212. Here, detector mask 100 includes plate 2 that includes plate wall 6 disposed in plate 2 and enclosing transmission orifice 4 arranged in a transmission profile. Detector mask 100 receives probe particles 208 from sample 206, transmits probe particles 216 having a trajectory coincident with transmission orifice 4, blocks probe particles 214 having a trajectory external to transmission orifice 4, and forms probe particle beam 210 comprising probe particles 216 transmitted by transmission orifice 4 to particle detector 212. It is contemplated that the transmission profile includes a sector, a semi-circle, an annular sector, or a combination thereof. The transmission profile provides the shape of transmission orifice 4 provided by plate wall 6 such that a particular imaging mode (e.g., bright-field imaging) can be performed. As shown in FIG. 5, transmission orifices 4 can independently have various transmission profiles (e.g., 8A, 8B, and 8C), wherein transmission profile 8A is an annular transmission profile; transmission profile 8B is a circular transmission profile, and transmission profile 8C is a semi-circular transmission profile.

Figure 6:
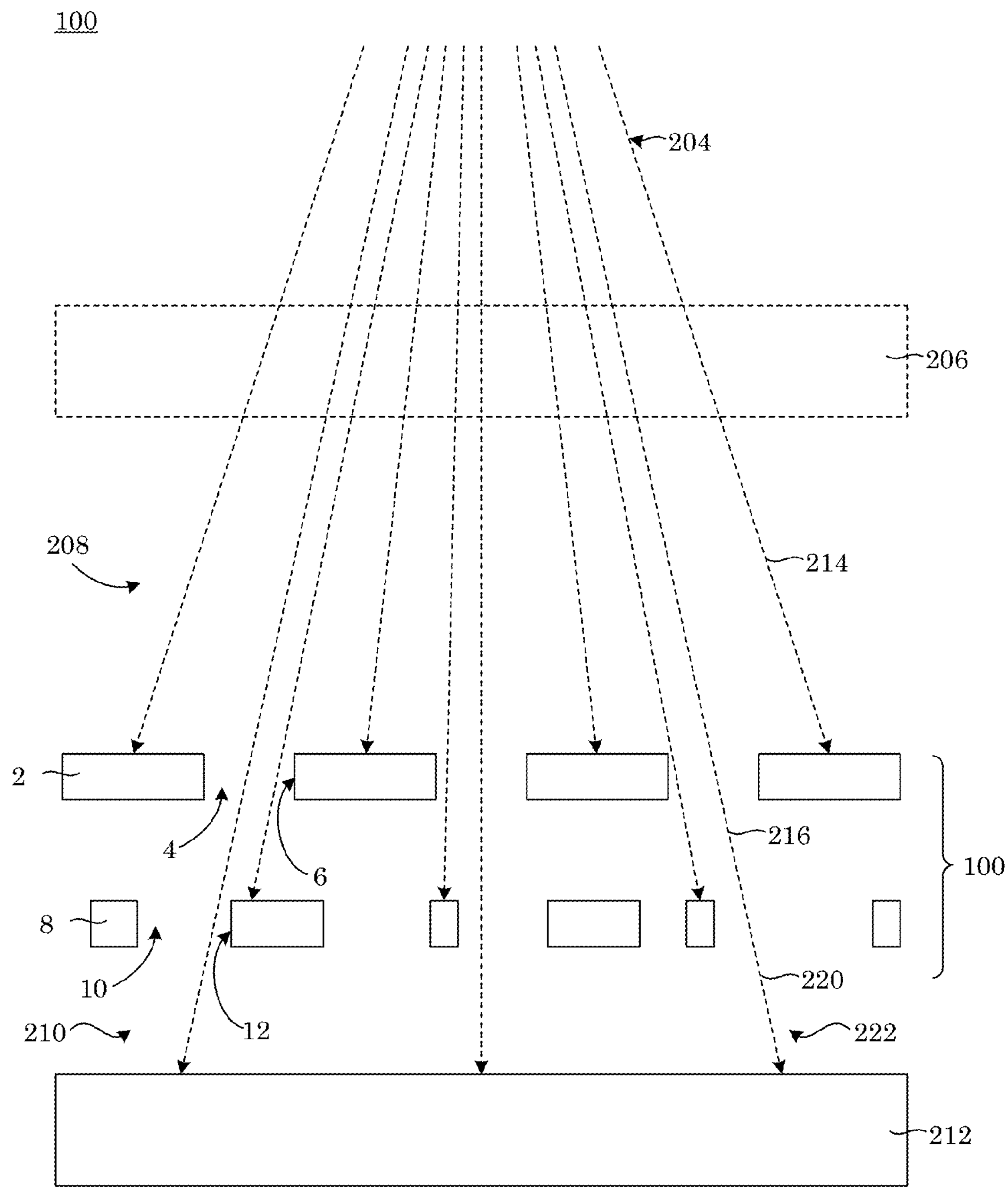
FIG. 6 shows a cross-section of a detector mask that includes a plurality of plates.
Figure 7:
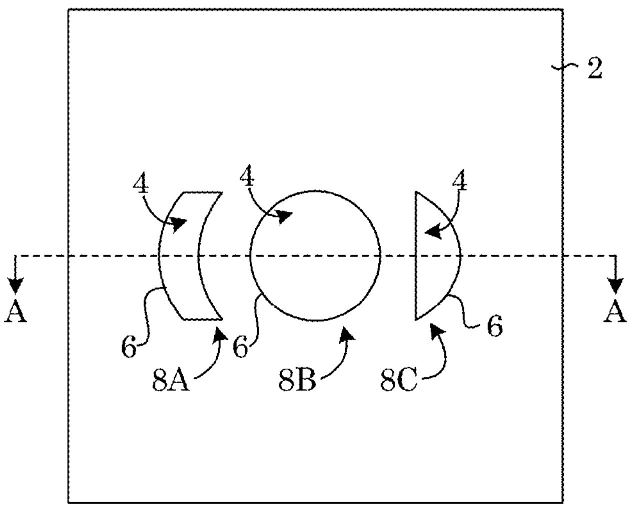
FIG. 7 shows a top view of plates of the plates of the detector mask shown in FIG. 6.
Figure 7:
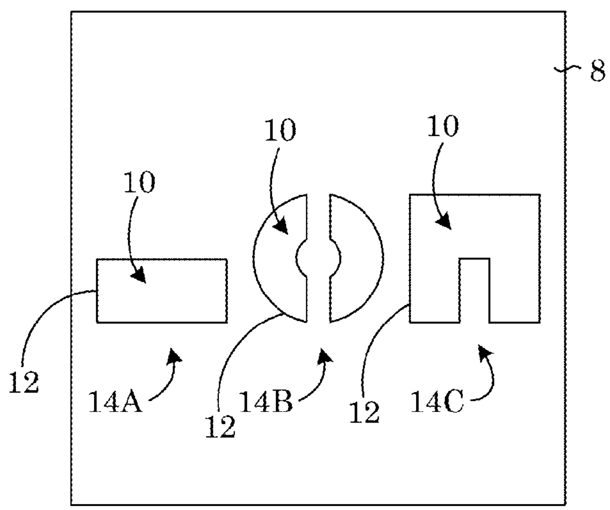
Figure 7:
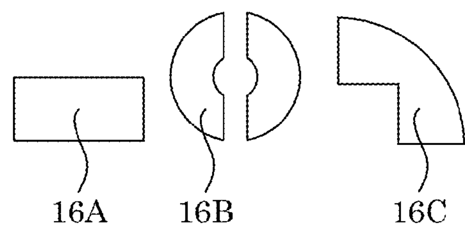

In an embodiment, with reference to FIG. 6 (cross-section along line A-A shown in FIG. 7) and FIG. 7 (top view), detector mask 100 transmits selectively a plurality of probe particles 216 to particle detector 212. Here, detector mask 100 includes first plate 2 that includes first plate wall 6 disposed in first plate 2 and enclosing first transmission orifice 4 arranged in a first transmission profile. First plate 2 receives probe particles 208 from sample 206, transmits probe particles 216 having a trajectory coincident with first transmission orifice 4, blocks probe particles 214 having a trajectory external to first transmission orifice 4, and forms first probe particle beam comprising probe particles 216 transmitted by transmission orifice 4.

Second plate 8 is disposed proximate to first plate 2 and includes second plate wall 12 disposed in second plate 8 and enclosing second transmission orifice 10 arranged in second transmission profile 14 that receives the first probe particle beam transmitted through first transmission orifice 4 of first plate 2, transmits probe particles 220 in the first probe particle beam having a trajectory coincident with second transmission orifice 10, blocks probe particles 218 in the first probe particle beam having a trajectory external to second transmission orifice 10, and forms second probe particle beam 222 that includes probe particles 220 transmitted by second transmission orifice 10. First plate 2 and second plate 8 are arranged in a stack in detector mask 100 such that the first transmission profile and second transmission profile 14 in combination provide a mask transmission profile through which the probe particles 220 are transmitted to particle detector 212.

It is contemplated that the first transmission and second transmission profile interpedently include a circle, sector, a semi-circle, an annular sector, a rectangle, or a combination thereof. The transmission profile provides the shape of transmission orifice (4 or 10) provided by plate wall (6 or 12) such that a particular imaging mode (e.g., bright field imaging) can be performed. As shown in panel B of FIG. 7, second transmission orifices 10 can independently have various second transmission profiles (e.g., 14A, 14B, and 14C), wherein second transmission profile 14A is a rectangular transmission profile; second transmission profile 14B is an annular transmission profile, and second transmission profile 14C is a U-shaped transmission profile. Also shown in panel C of FIG. 7 is mask transmission profile 16 formed by overlap of the first transmission profile and the second transmission profiles. It should be appreciated that a shape of a cross-section of probe particles 220 incident on a surface of probe detector 212 have the profile provided by mask transmission profile 16. As used herein, "profile" refers to a shape formed by the transmission orifices (e.g., 4, 10, and the like) bounded by respective plate walls (e.g., 6, 12, and the like).

Detector mask 100 can include a number (e.g., 1, 2, 3, 4, or more) of plates to form a selected mask transmission profile. According to an embodiment, with reference to panel A of FIG. 8, detector mask 100 includes third plate 20 disposed on first plate 2, wherein second plate 8 is interposed between first plate 2 and third plate 20. Here, third plate 20 can include a third plate wall disposed in third plate 20 and enclosing a third transmission orifice arranged in a third transmission profile to receive the second probe particle beam, to transmit probe particles in the second probe particle beam having a trajectory coincident with the third transmission orifice, to block probe particles in the second probe particle beam having a trajectory external to the third transmission orifice, and to form a third probe particle beam including the probe particles transmitted by the third transmission orifice. First plate 2, second plate 8, and third plate 20 are arranged in a stack in detector mask 100 such that the first transmission profile, the second transmission profile, and the third transmission profile in combination provide the mask transmission profile through which the probe particles are transmitted to the particle detector.

Figure 8:
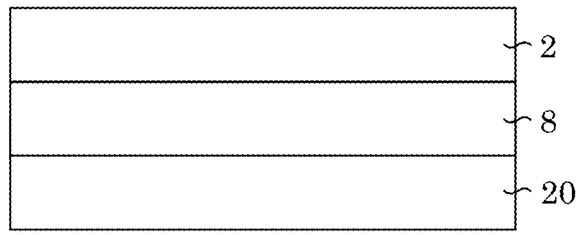
FIG. 8 shows a side view of a detector mask.
Figure 8:
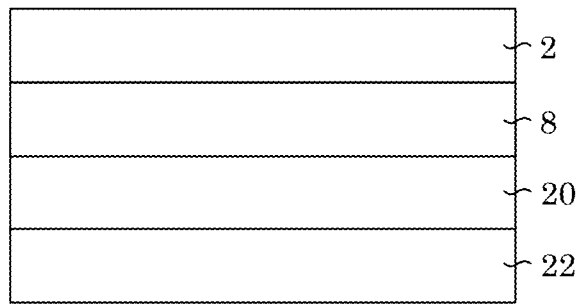

According to an embodiment, with reference to panel B of FIG. 8, detector mask 100 includes fourth plate 22 disposed on third plate 20. Here, fourth plate 22 includes a fourth plate wall disposed in the fourth plate and enclosing a fourth transmission orifice arranged in a fourth transmission profile to receive the third probe particle beam, to transmit probe particles in the third probe particle beam having a trajectory coincident with the fourth transmission orifice, to block probe particles in the third probe particle beam having a trajectory external to the fourth transmission orifice, and to form a fourth probe particle beam comprising the probe particles transmitted by the fourth transmission orifice. In this manner, first plate 2, second plate 8, third plate 20, and fourth plate 22 are arranged in a stack in detector mask 100 such that the first transmission profile, the second transmission profile, the third transmission profile, and the fourth transmission profile in combination provide the mask transmission profile through which the probe particles are transmitted to the particle detector.

An arrangement of transmission orifices (e.g., 4, 10) in plate (e.g., 2, 8) of detector mask 100 can be selected, e.g., to accommodate an imaging modality or to accommodate a layout of an active region or a shape of an active region in particle detector 212. In an embodiment, with reference to FIG. 9, plate 2 is segmented into a plurality of quadrants (16, 18, 20, 22; indicated by dashed lines) in which quadrants (16, 18, 20, 22) independently include transmission orifice 4 having independent transmission profiles that can include a circle, a sector, a semi-circle, an annular sector, a rectangle, or a combination comprising at least one of the foregoing first transmission profiles. Here, quadrant 16 can include transmission orifice 4 bounded by plate wall 6 with transmission profile 32 that is a rectangle. Similarly, quadrant 18 can include transmission orifices 4 bounded by plate walls 6 with respectively transmission profile 26 (a rectangle) and 24 (a circle). Quadrant 20 includes annular sector transmission profile 30, and quadrant 22 includes semi-circle transmission profile 28. Plate 2 further can include center transmission orifice 34 disposed centrally among quadrants (16, 18, 20, 22).

Figure 9:
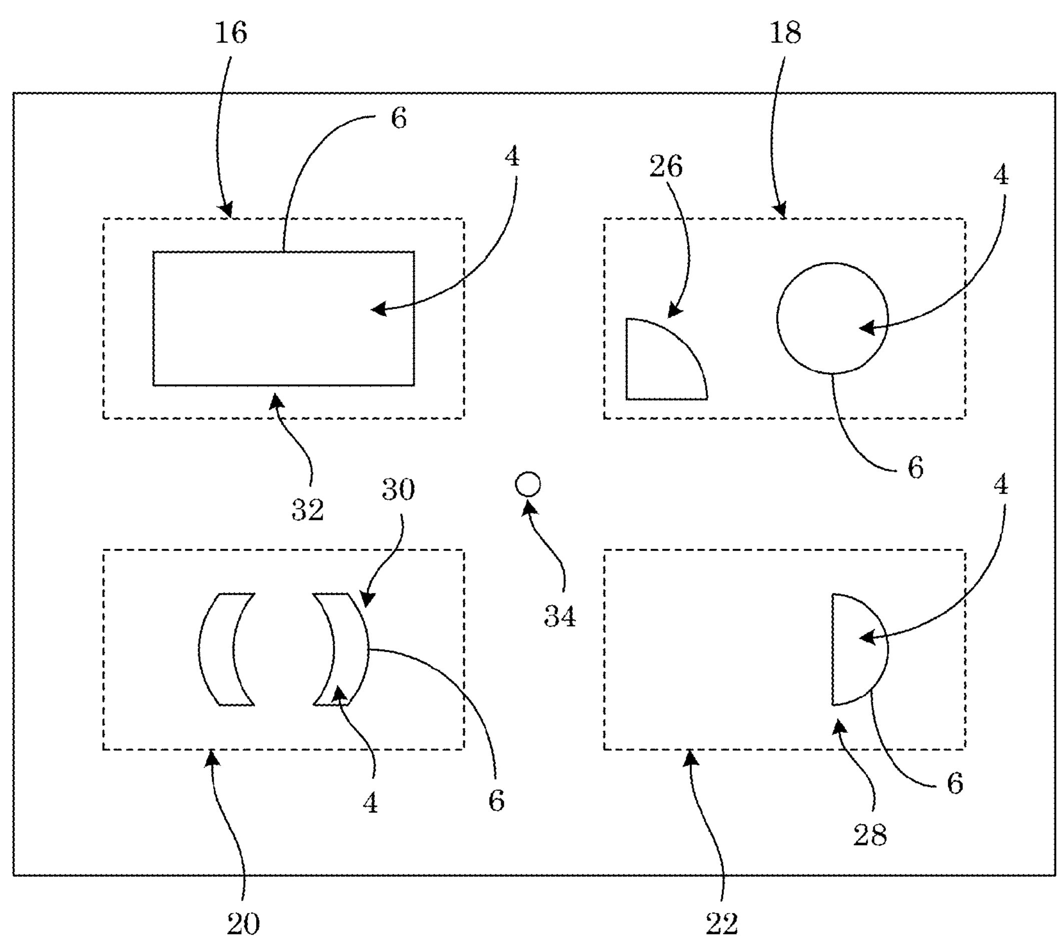
FIG. 9 shows a top view of a plate for a detector mask, wherein the plate includes a plurality of quadrants with transmission orifices.
Figure 10:
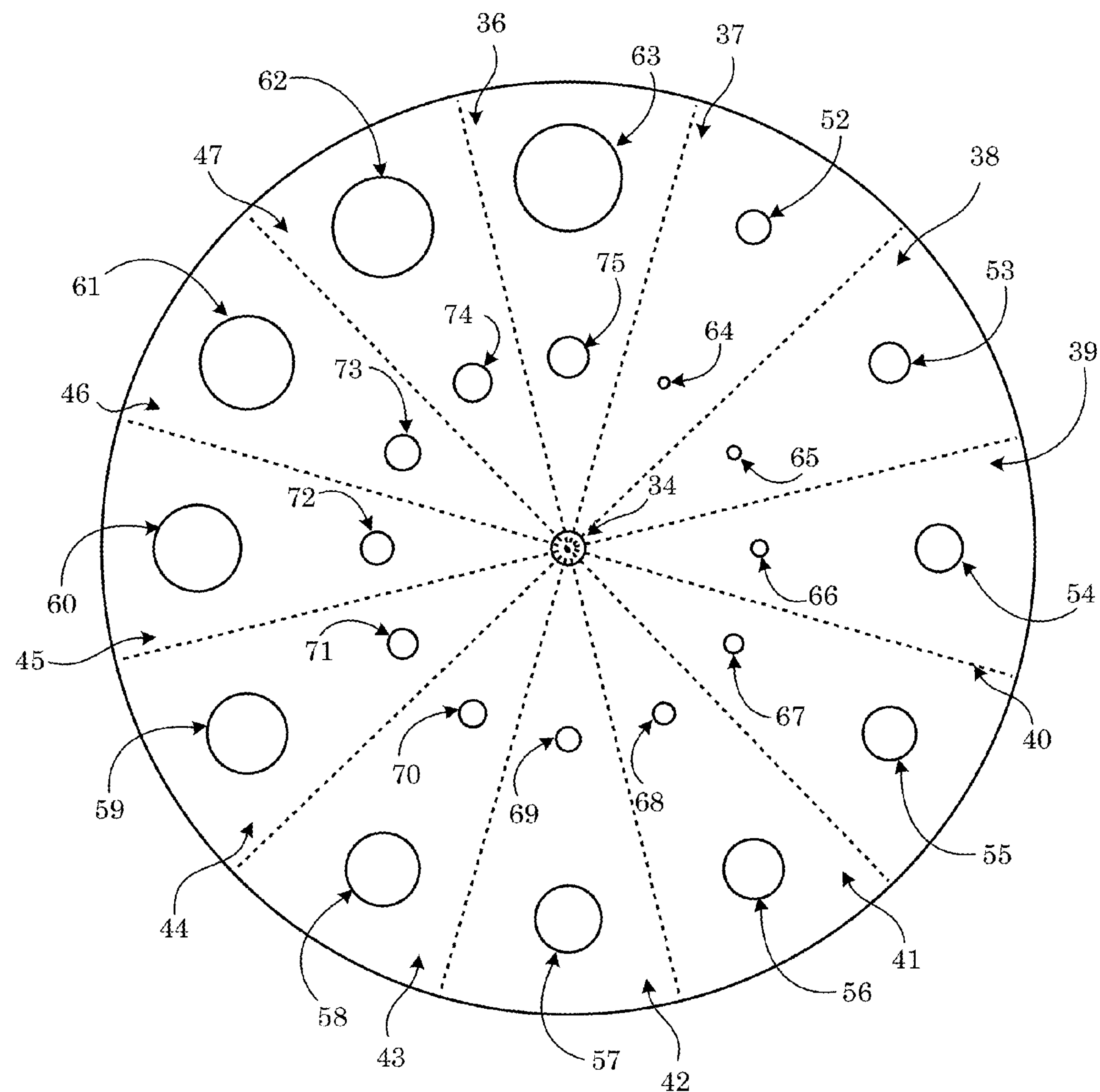
FIG. 10 shows a top view of a plate for a detector mask, wherein the plate includes a plurality of sectors with transmission orifices.
Figure 18:
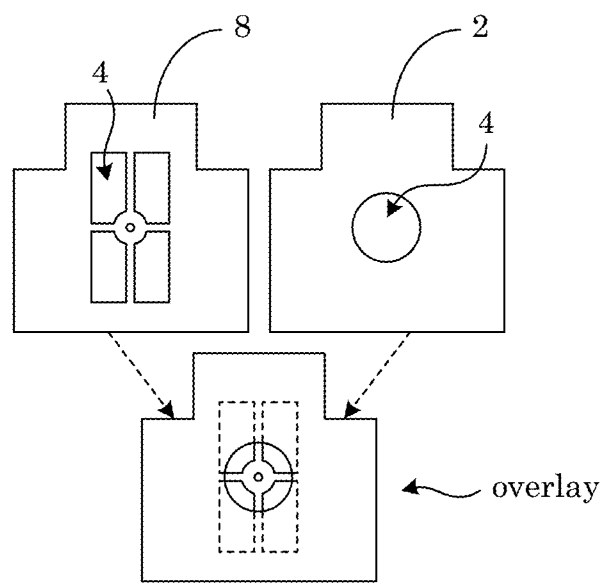
FIG. 18 shows exemplary plates for the detector mask shown in FIG. 14.
Figure 18:
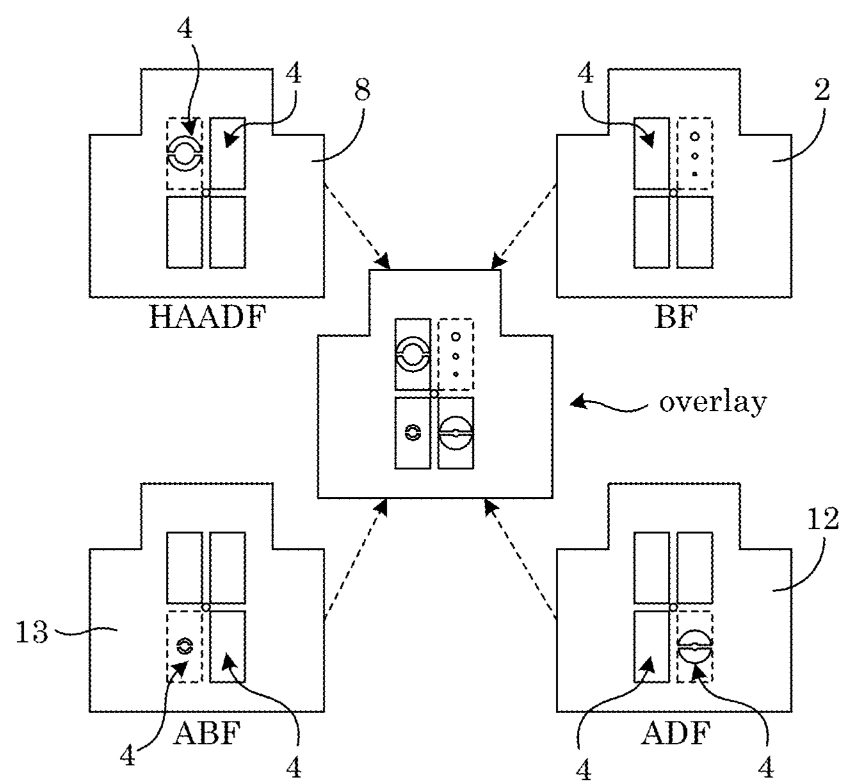

A shape of plate 2 can be selected, e.g., to accommodate an imaging modality, to accommodate a layout of an active region or a shape of an active region in particle detector 212, or based on available physical space available in a scope such as a spectroscope or microscope. The shape of plate 2 can be square, round, rectangle, irregular, polygonal, a truncated shape thereof, and the like. An exemplary rectangular shape of plate 2 is shown in FIG. 9. An exemplary circular shape of plate 2 is shown in FIG. 10. An exemplary truncated rectangular shape of plate 2 is shown in FIG. 18.

Figure 11:
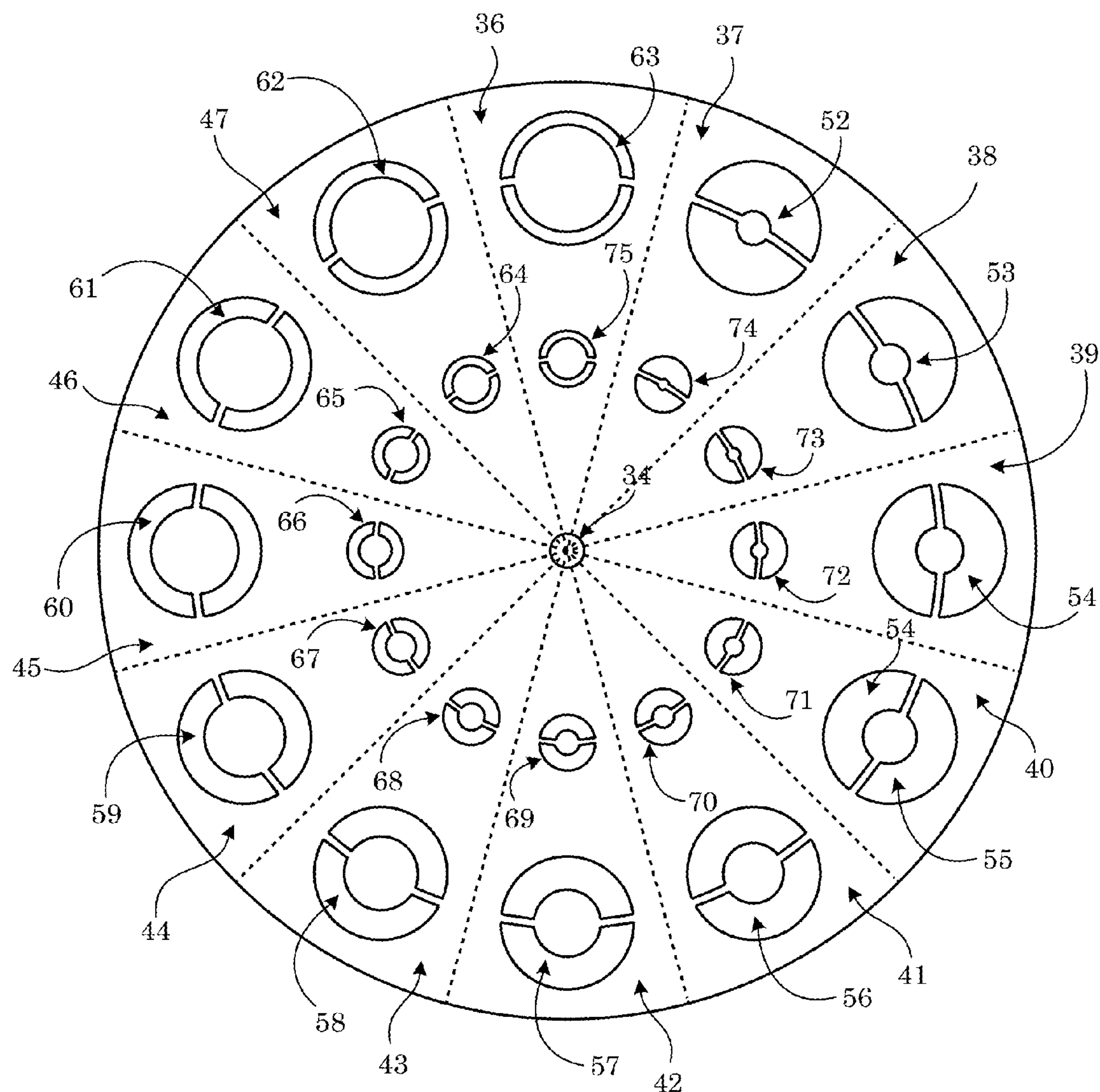
FIG. 11 shows a top view of a plate for a detector mask, wherein the plate includes a plurality of sectors with transmission orifices.

In an embodiment, with reference to FIG. 10 and FIG. 11, plate 2 is segmented into a plurality of sectors (36-47, separated by dashed lines in FIG. 10 and FIG. 11) in which sectors (36-47) independently include transmission orifice 4 having independent transmission profiles (52-63) that can include a circle, a sector, a semi-circle, an annular sector, a rectangle, or a combination comprising at least one of the foregoing first transmission profiles. The sectors are distributed azimuthally about a center of rotation of plate 2. Moreover, sector (36-47) includes transmission orifice second transmission orifice 4 with transmission profiles (64-75) bounded by plate wall 6 with transmission profiles that are, e.g., circular transmission profiles (in FIG. 10) and annular sector transmission profiles (in FIG. 11). Plate 2 further can include center transmission orifice 34 disposed centrally among the sectors.

Figure 12:
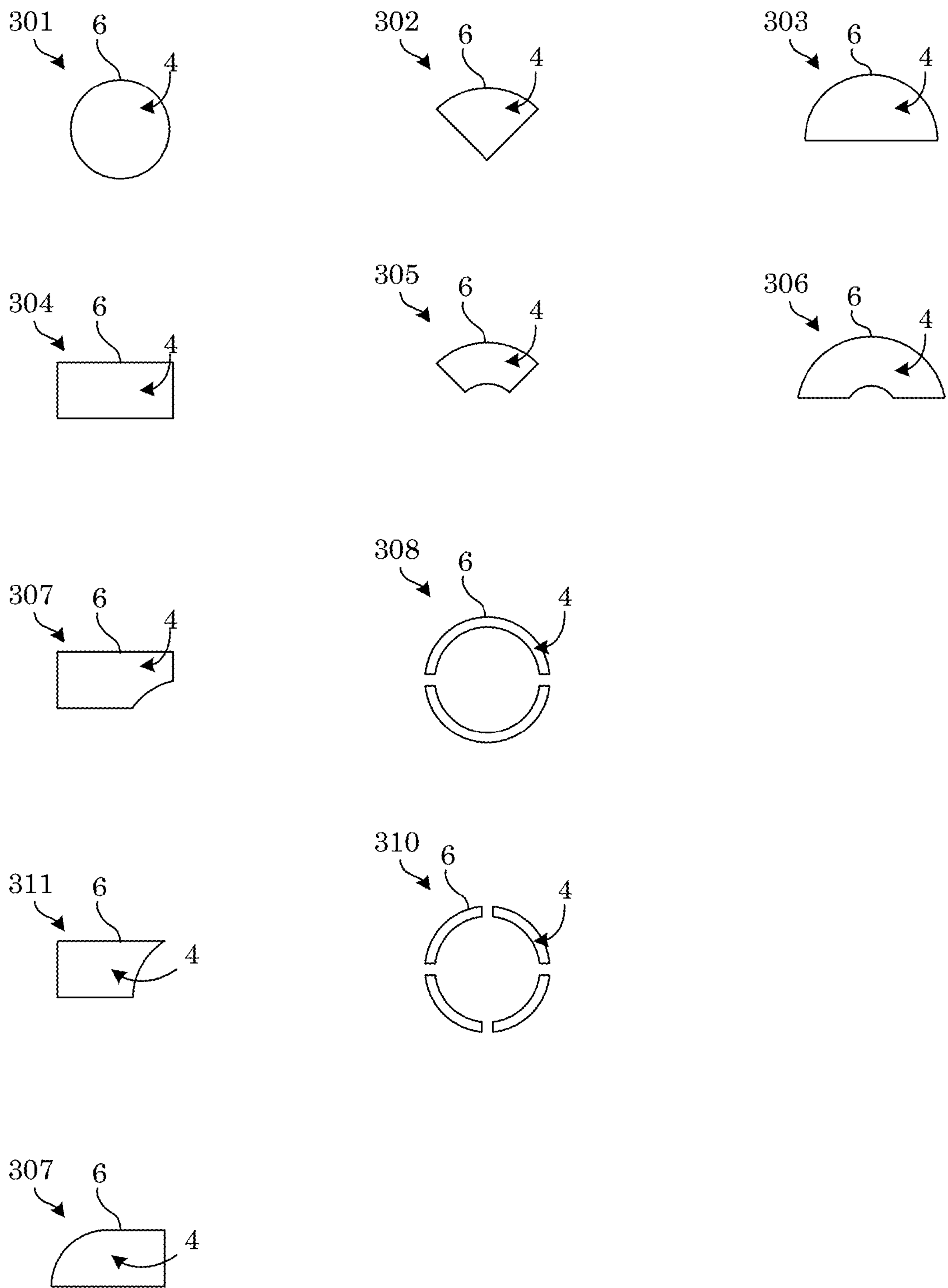
FIG. 12 shows a plurality of transmission profiles for a plate of a detector mask.
Figure 13:
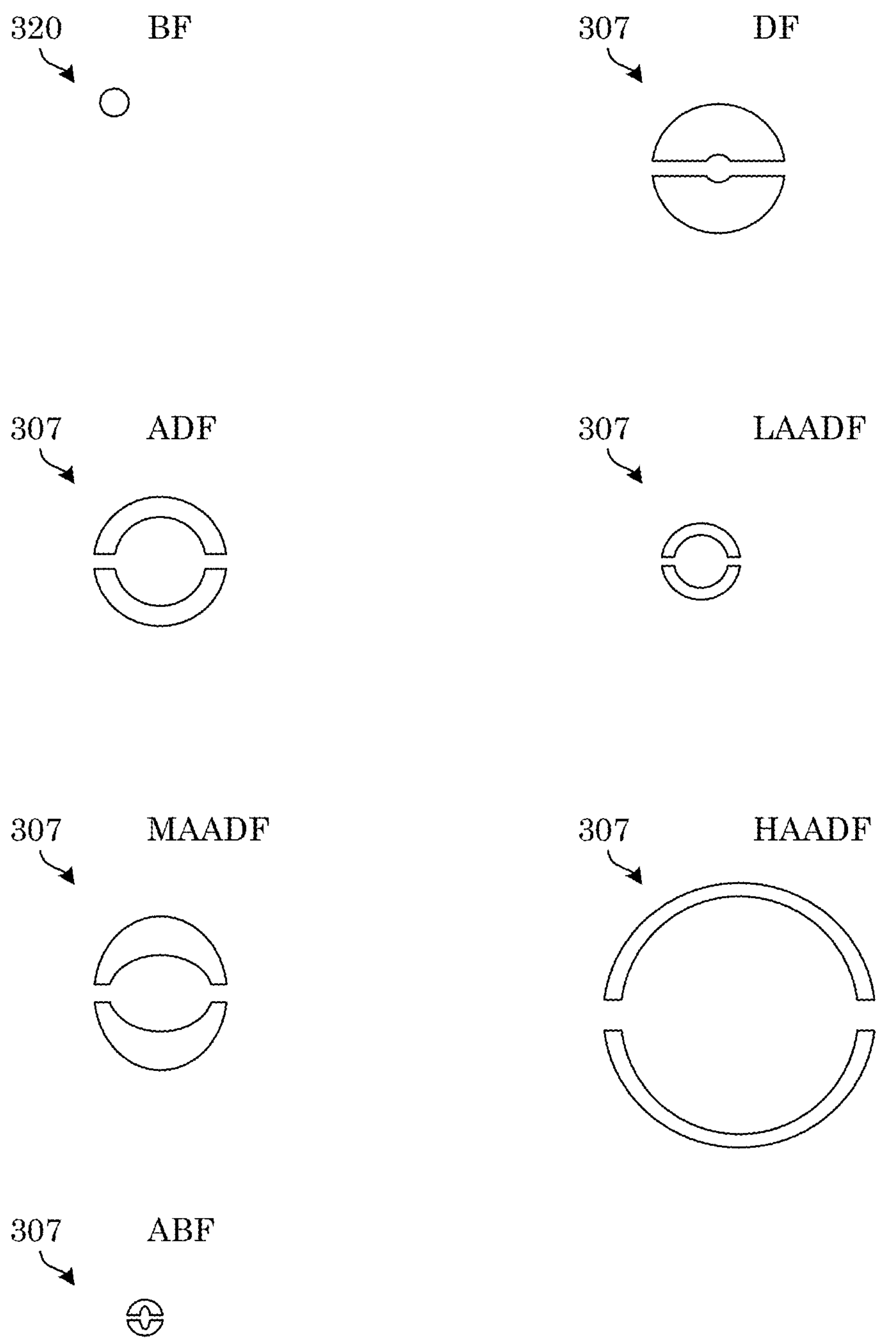
FIG. 13 shows a plurality of transmission profiles for a plate of a detector mask.

The transmission profile of plate 2 can be selected to provide a particular imaging modality, to accommodate a layout of an active region, or to accommodate a shape of an active region in particle detector 212. FIG. 12 shows exemplary transmission profiles 301 to 311 that include, e.g., circular sector, semi-circle, rectangular, annular sector, and the like. The transmission profiles can be selected to provide a particular imaging modality, e.g., in charged particle (e.g., electron) microscopy such as bright field imaging, dark field imaging, annular dark field imaging, low angle annular dark field imaging, medium angle annular dark field imaging, high angle annular dark field imaging, annular bright field imaging, or a combination comprising at least one of the foregoing imaging modalities, and the like. In an embodiment, with reference to FIG. 13, the transmission profiles of the of the transmission orifice can include a bright field (BF) transmission profile 320; a dark field (DF) transmission profile 321; an annular dark field (ADF) transmission profile 322; a low-angle annular dark field (LAADF) transmission profile 323; a medium angle annular dark field (MAADF) transmission profile 324; a high angle annular dark field (HAADF) transmission profile 326; an annular bright field (ABF) transmission profile 327; or a combination comprising at least one of the foregoing transmission profiles.

Figure 14:
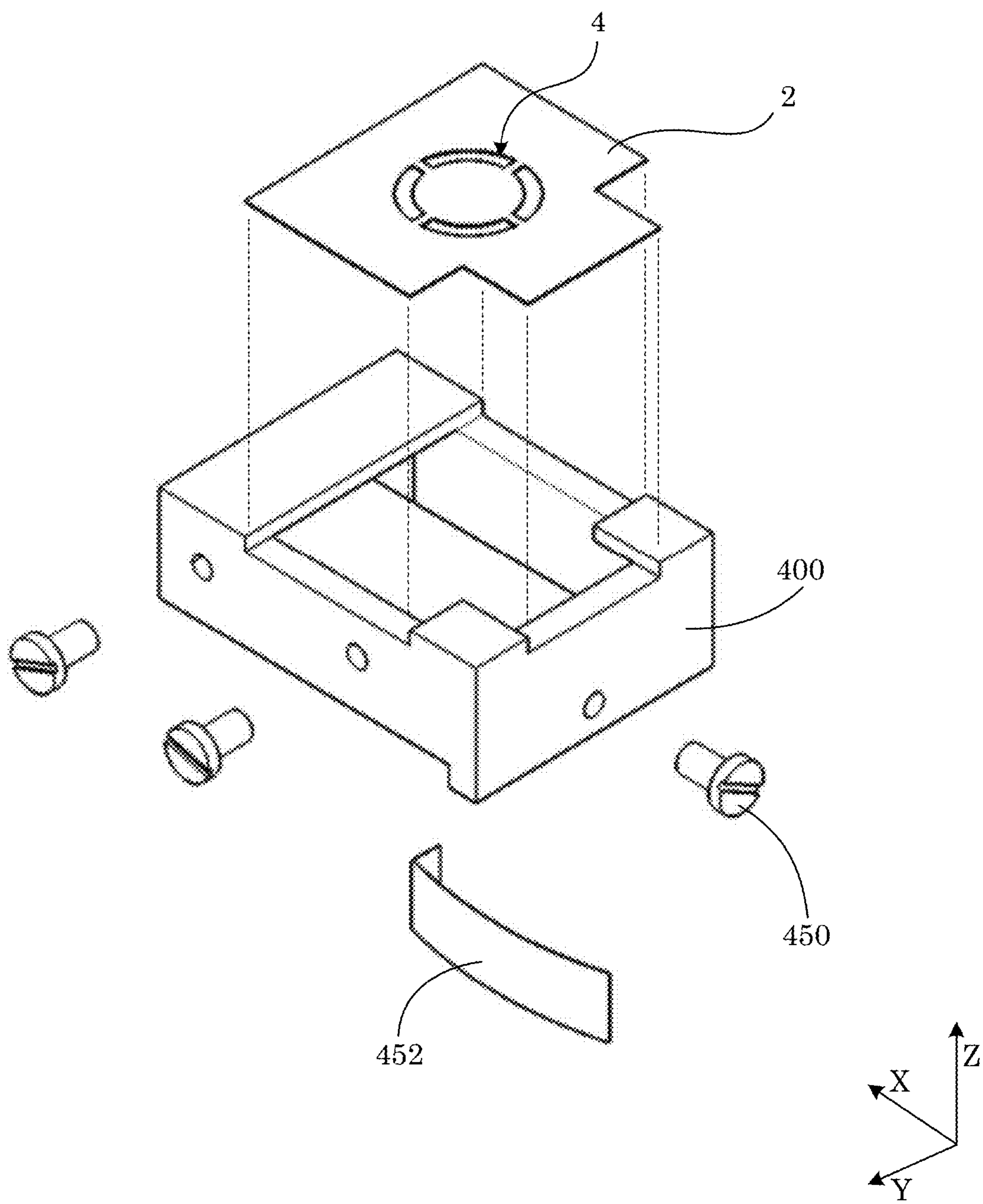
FIG. 14 shows an exploded view of a detector mask.
Figure 15:
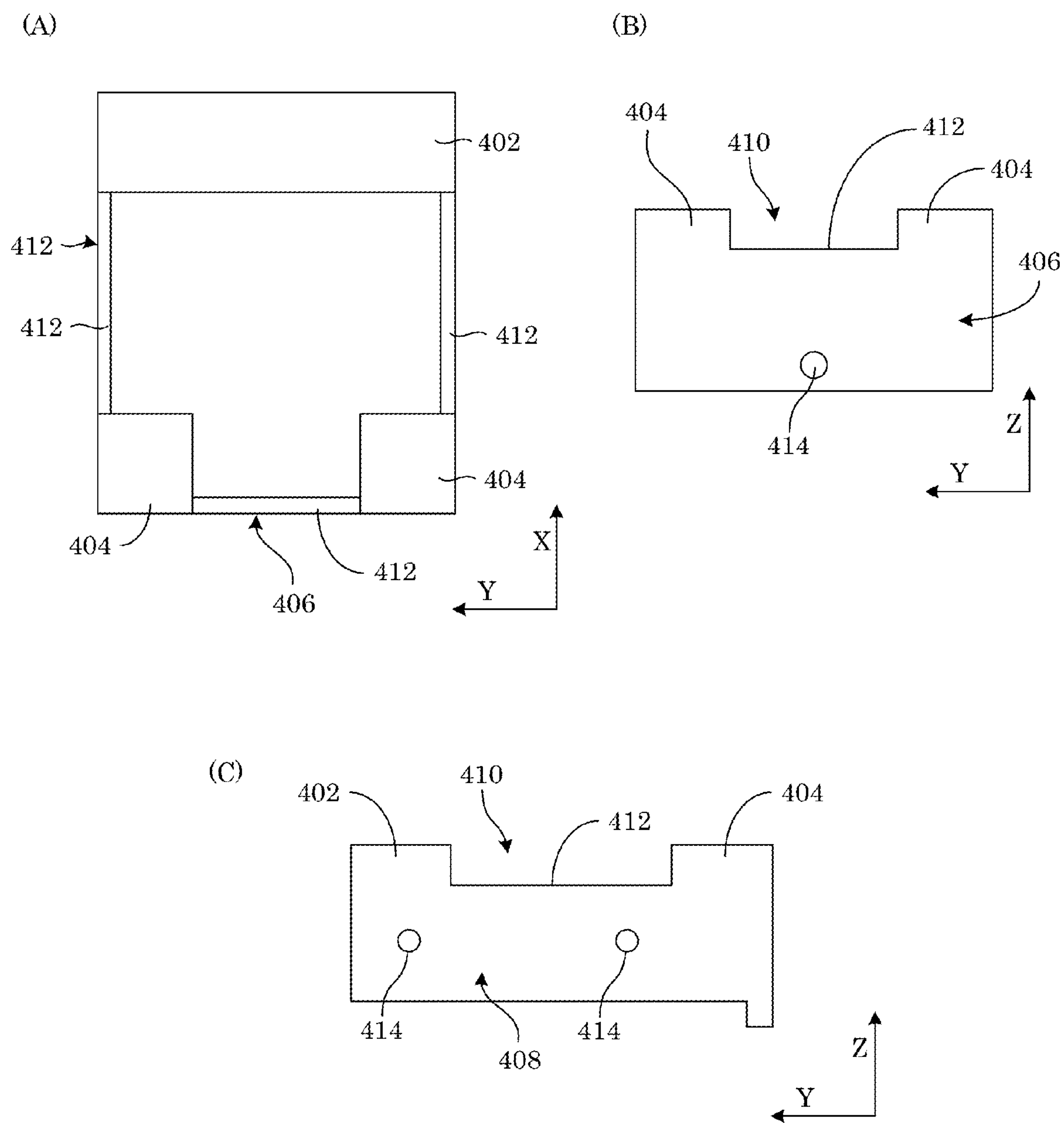
FIG. 15 shows several views of the support of the detector mask shown in FIG. 14.
Figure 16:
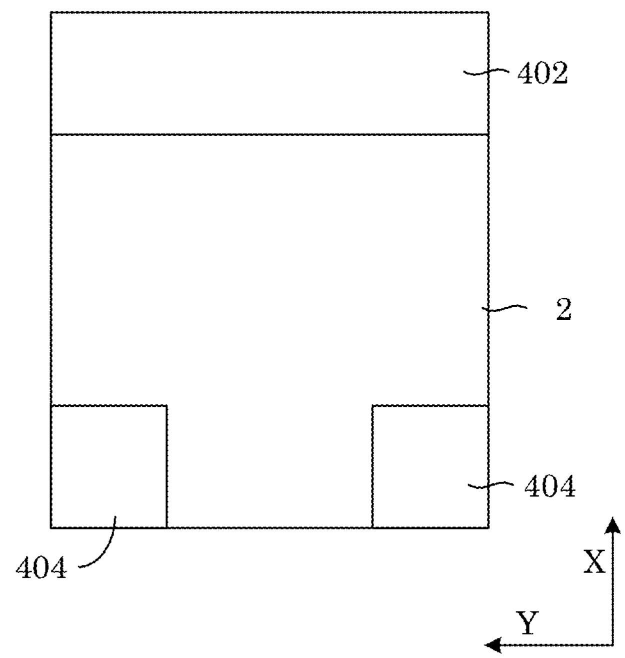
FIG. 16 shows several views of the detector mask and of the support of the detector mask shown in FIG. 14.
Figure 16:
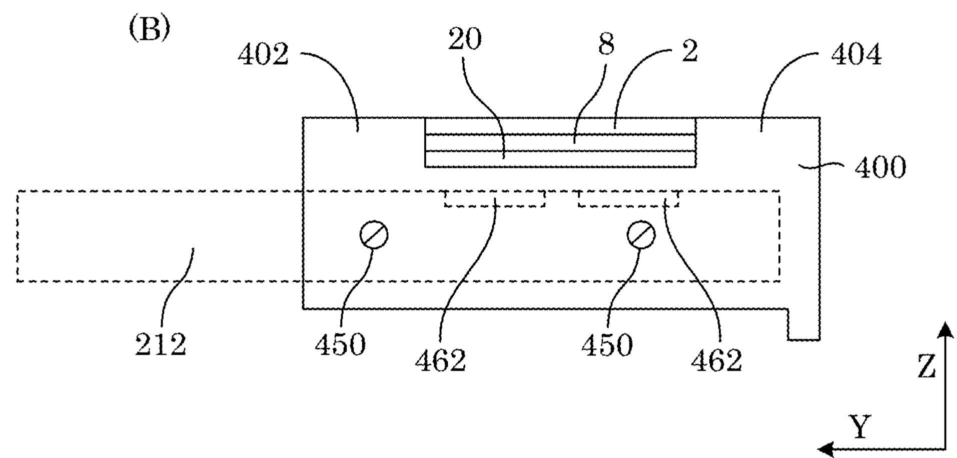

In an embodiment, with reference to FIG. 14, detector mask 100 includes support 400 on which plate 2 is disposed. It is contemplated that support 400 can mount on particle detector 212 in some embodiments in which fasteners 450 can fasten and align support 400 to particle detector 212. Additionally, retaining spring 452 can be included to provide tension between particle detector 212 and support 400 in combination with fasteners 450. FIG. 15 shows a top view (panel A), front view (panel B), and side view (panel C) of support 400. Here, support 400 includes mating surfaces 412 disposed on top surface 410 to receive and to mate to plate 2; shelf (402, 404) to dispose support 400 on particle detector 212; fastener mate 414, e.g., a threaded receptacle) in surface 406 to receive and engage fastener 450 (e.g., a screw) for aligning transmission orifice 4 to the active region of particle detector 212; and fastener mate 414 disposed on surface 408 to receiver fastener 450 to attach support 400 of detector mask 100 to particle detector 212. Panel A (top view) and panel B (side view) of FIG. 16 show plates (2, 8, 20) disposed on support 400, wherein particle detector 212 includes active area 462.

Figure 17:
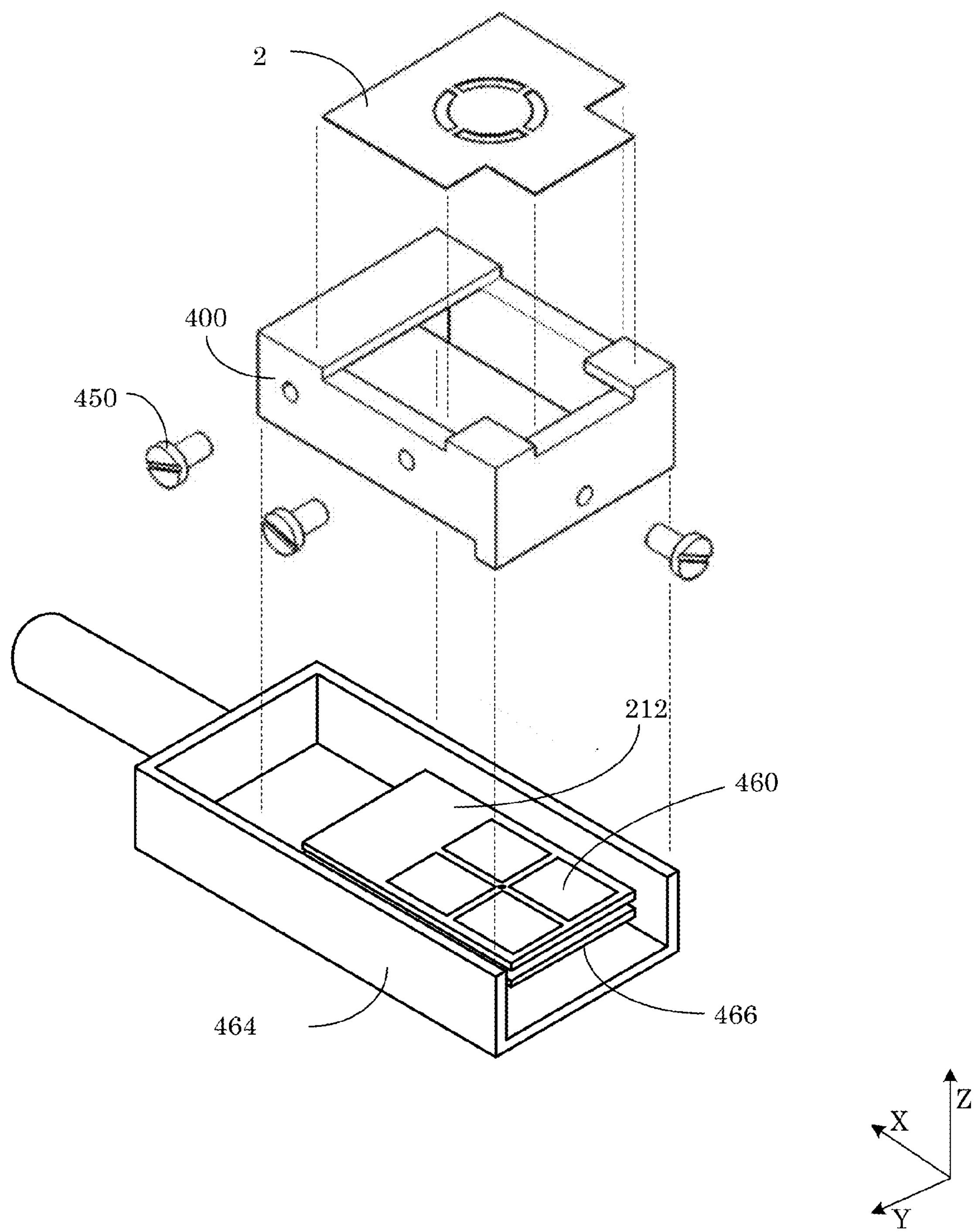
FIG. 17 shows an exemplary detector mask disposed on a particle detector.

In an embodiment, with reference to FIG. 17, detector mask 100 includes plate 2 disposed on support 400. Support 400 can be attached to detector housing 464 in which particle detector 212 is disposed. Here, particle detector 212 can include a plurality of active areas 462 disposed on first detector plate 460. First detector plate 462 is interposed between plate 2 and second detector plate 466.

FIG. 18 shows exemplary plates (2, 8, 12, 13) having a truncated rectangular shape with various transmission profiles for their transmission orifice. Panel A of FIG. 18 include plates (2, 8) with transmission orifices that respectively include a circular transmission profile and a plurality of truncated rectangular transmission profiles with a central circular orifice, wherein plate 2 disposed on plate 8 (indicated as "overlaid" in FIG. 18, panel A) produces mask transmission profile that includes the annular sector transmission profile with a central circular orifice. Similarly, panel B of FIG. 18 include plates (2, 8, 12, 13) with transmission orifices that respectively include a BF transmission profile and a plurality of truncated rectangular transmission profiles with a central circular orifice (plate 2); an HAADF transmission profile and a plurality of truncated rectangular transmission profiles with a central circular orifice (plate 8); an ADF transmission profile and a plurality of truncated rectangular transmission profiles with a central circular orifice (plate 12); and an ABF transmission profile and a plurality of truncated rectangular transmission profiles with a central circular orifice (plate 13), wherein plate 2, plate 8, and plate 12 disposed on plate 13 (indicated as "overlaid" in FIG. 18, panel B) produce a mask transmission profile that include the BF transmission profile, HAADF transmission profile, ADF transmission profile, and the ABF transmission profile with a central circular orifice.

Figure 19:
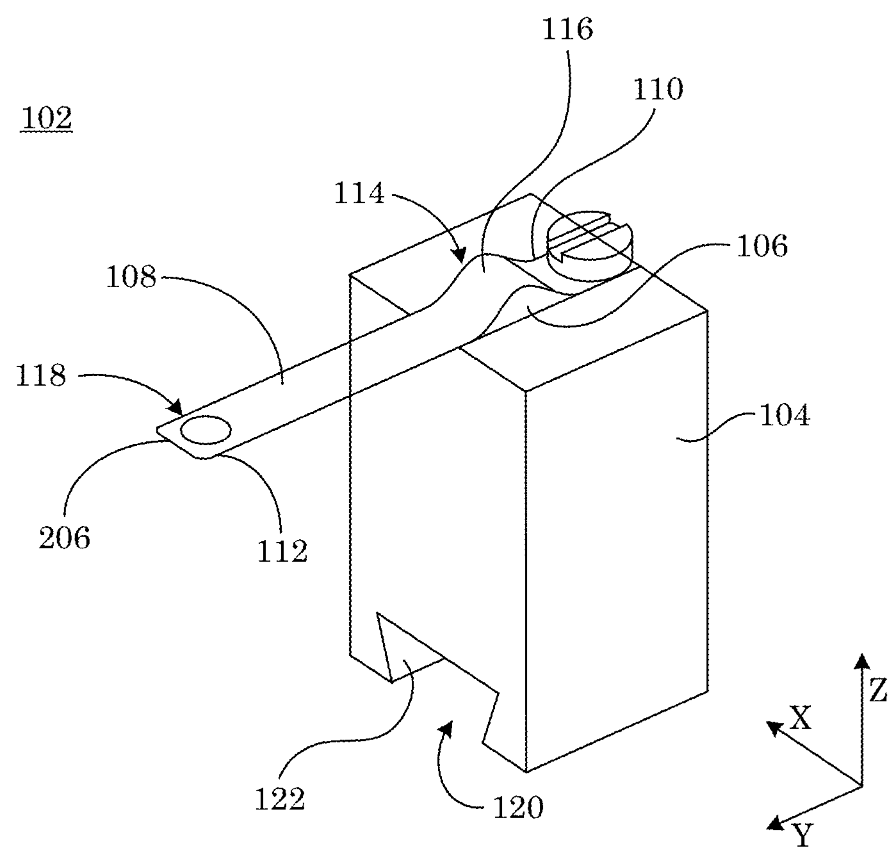
FIG. 19 shows a perspective view of a sample holder.
Figure 24:
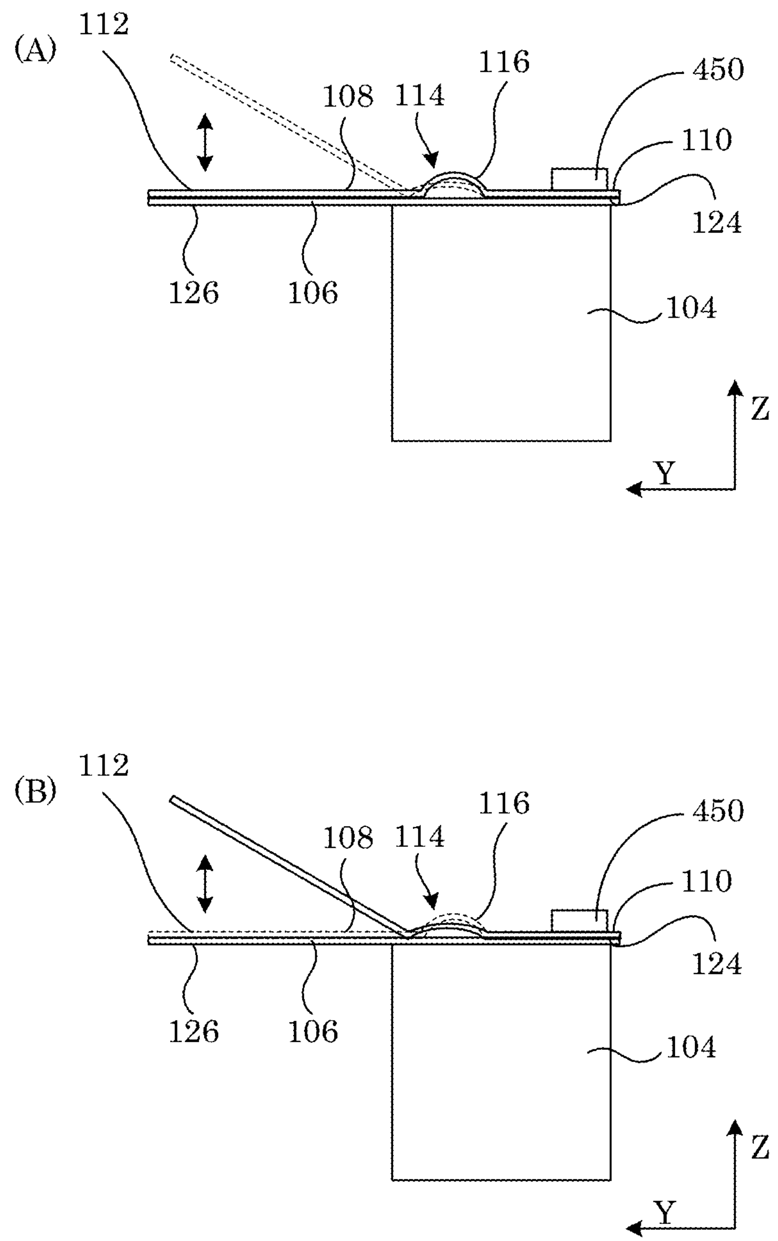
FIG. 24 shows a sample holder in a relaxed position (panel A) and a stretched position (panel B)

Probe particles are communicated from sample 206 to detector mask 100. In an embodiment, with reference to FIG. 19 (perspective view), FIG. 20 (exploded view), and FIG. 21 (side view (panel A), top view (panel B), side view from surface 142 (panel C), and bottom view (panel D)), sample 206 is received by and held by sample holder 102. Sample holder 102 includes basal member 104; inferior cantilever arm 106 disposed on basal member 104 to receive sample 206 and including: first mount end 124 proximately attached to basal member 104 and first free end 126 disposed distal to and protruding away from basal member 104 and first mount end 124, wherein first free end 126 is flexible relative to first mount end 124; and superior cantilever arm 108 disposed on basal member 104 opposing inferior cantilever arm 106 such that inferior cantilever arm 106 is interposed between basal member 104 and superior cantilever arm 108. Superior cantilever arm 108 includes: second mount end 110 proximately attached to basal member 104; second free end 112 disposed distal to and protruding away from basal member 104 and second mount end 110. Second free end 112 is flexible relative to second mount end 110. Superior cantilever arm 108 also includes curved intermediate armlet 114 interposed between second mount end 110 and second free end 112, wherein curved intermediate armlet 114 includes depressible crook 116. Depressible crook 116 is in a relaxed position when not depressed, and depressible crook 116 is in a stretched position when depressed. Moreover, first free end 126 and second free end 112 opposingly engage and retain sample 206 between first free end 126 and second free end 112 when depressible crook 116 is in the relaxed position (see FIG. 24), and first free end 126 is spaced apart from second free end 112 to release or to receive sample 206 between first free end 126 and second free end 112 when depressible crook 116 is in the stretched position (FIG. 24). Fastener 450 can attach cantilever arms (106, 108) to basal member 104 at arm surface 146 of basal member 104, wherein fastener hole 140 (e.g., threaded hole) of basal member receives and engages fastener 450 (e.g., a screw). Basal member 104 can have first surface 142 and second surface 144 that can be at an arbitrary angle, e.g., orthogonal, with respect to one another.

Sample holder 102 further can include first eyelet 128 disposed on first free end 126 and second eyelet 118 disposed on second free end 112. First eyelet 128 and second eyelet 118 provide exposure of a portion of sample 206 to a plurality of source particles such that sample 206 communicates probe particles to detector mask 100. Basal member 104 can include receiver 120 bounded by mating member 122 to attach sample holder 102 to a sample position manipulator of a scope, e.g., a microscope or spectroscope.

Figure 20:
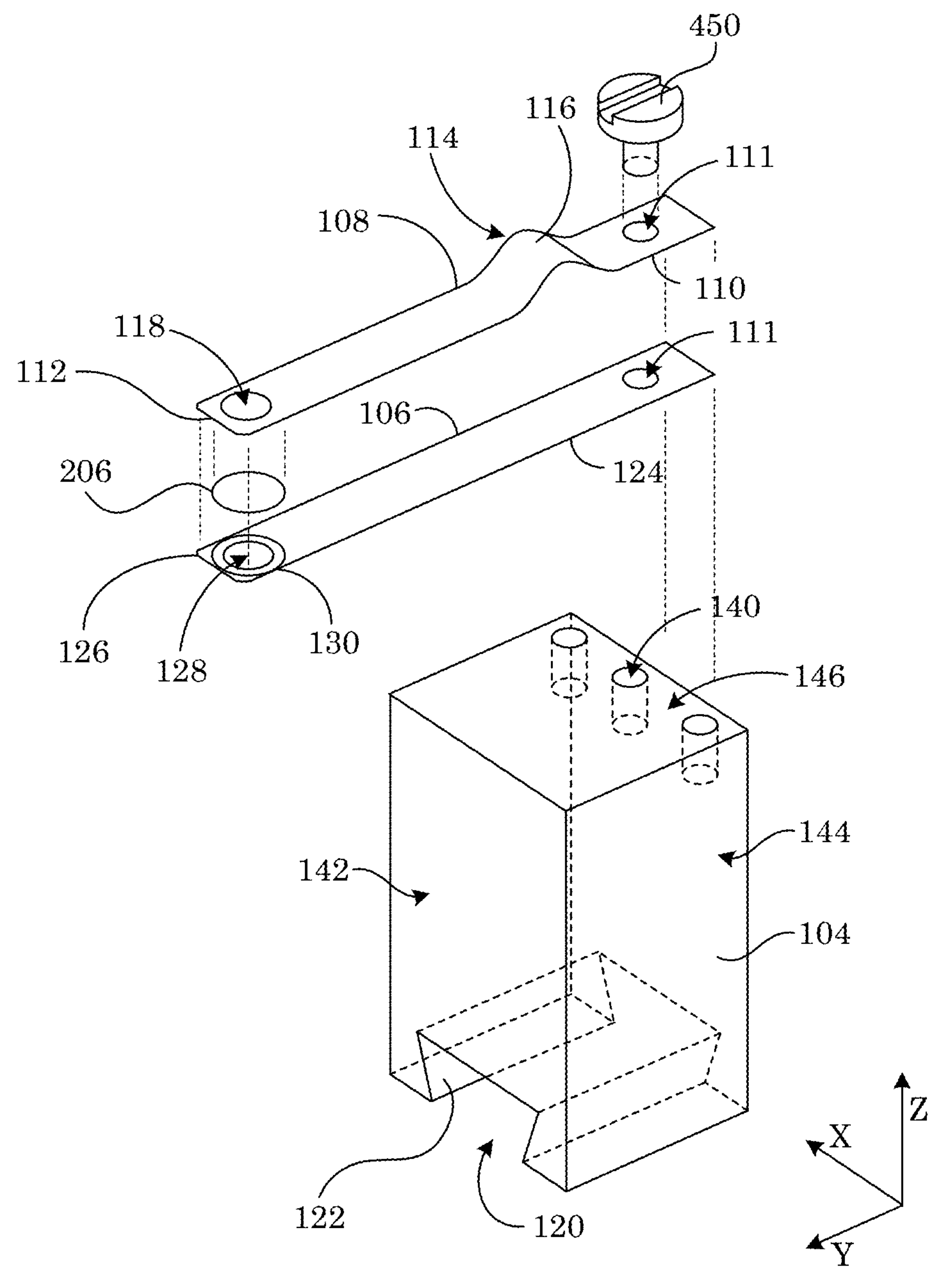
FIG. 20 shows an exploded view of the sample holder shown in FIG. 19.
Figure 21:
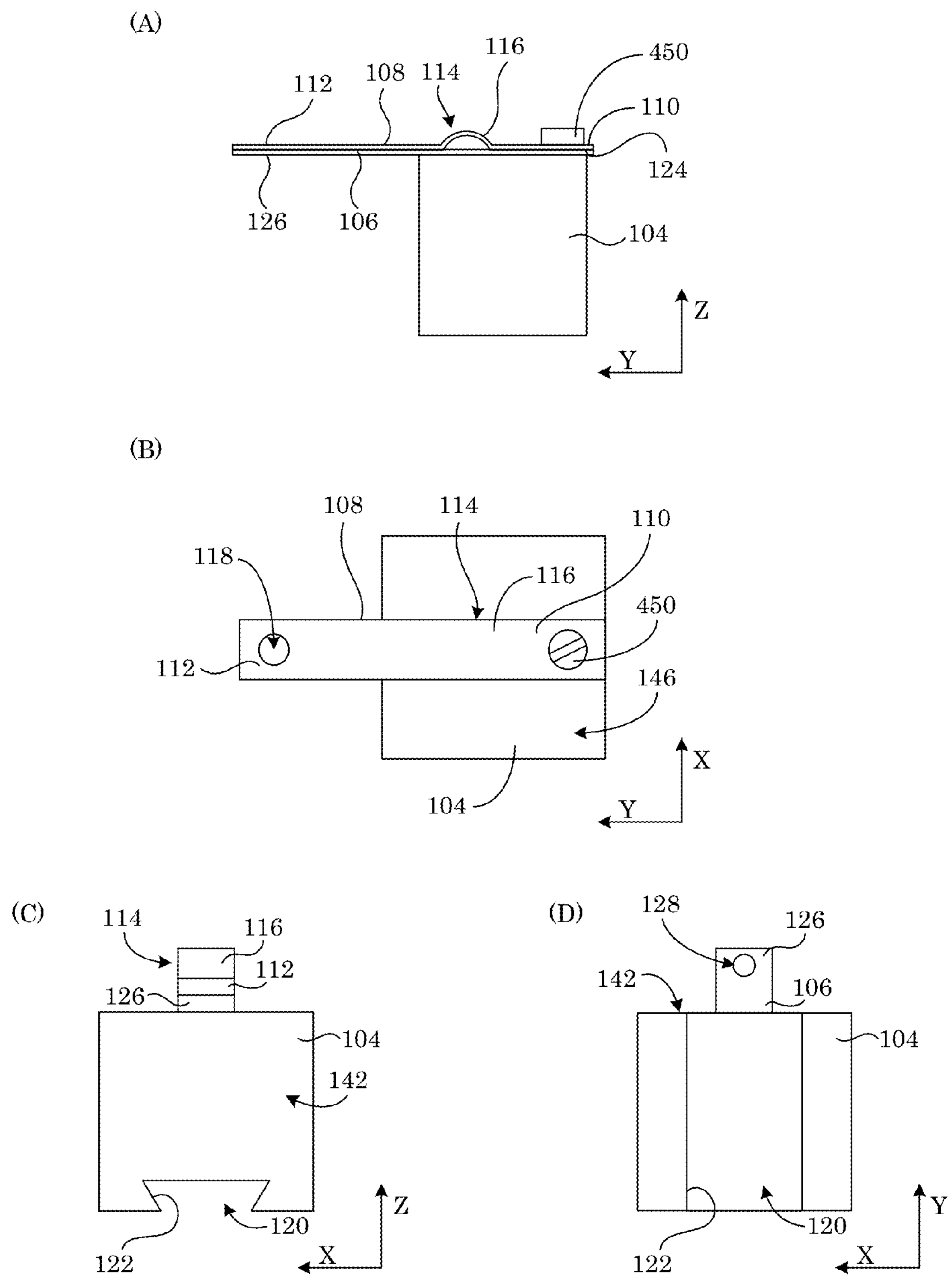
FIG. 21 shows several views of the sample holder shown in FIG. 19.
Figure 22:
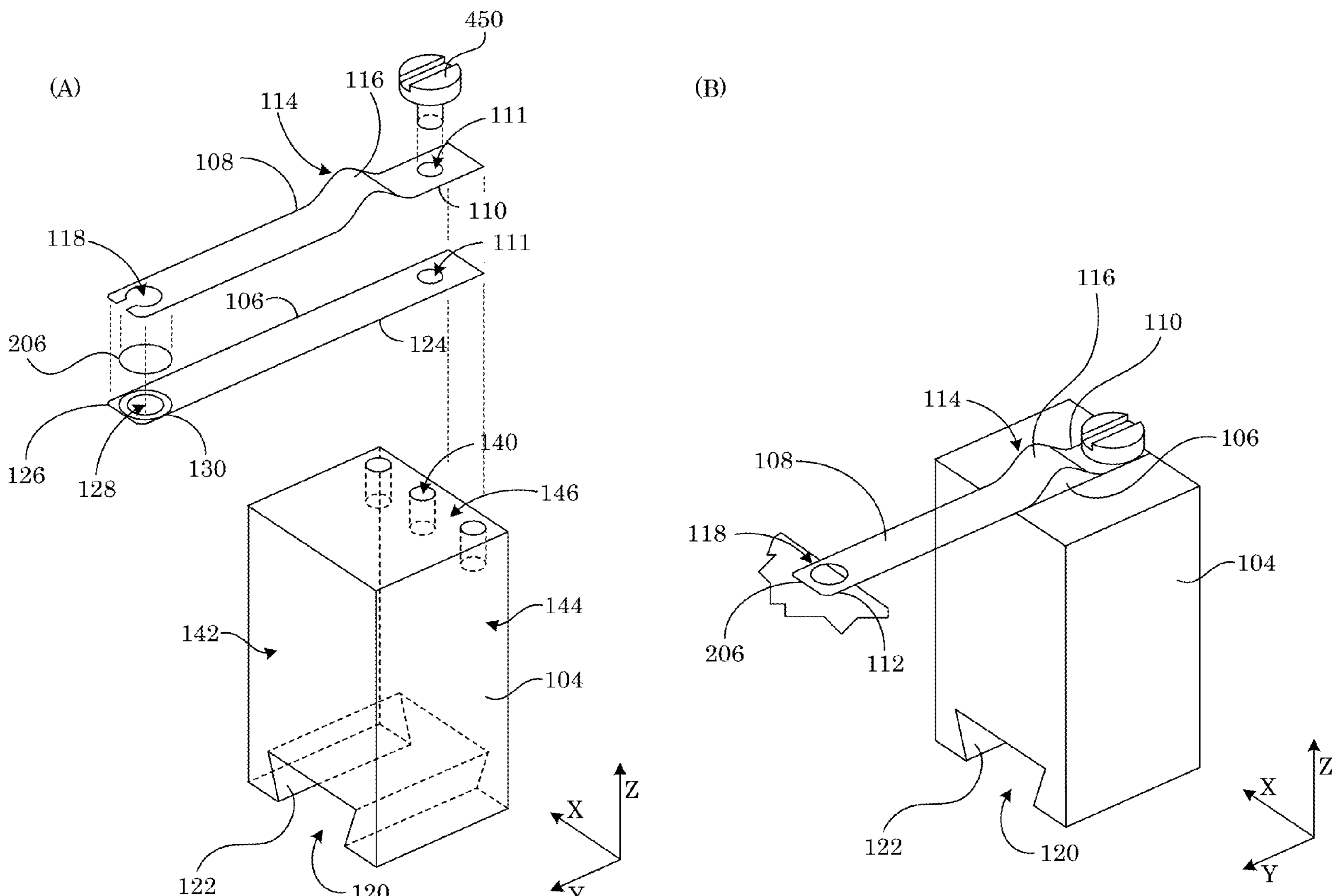
FIG. 22 shows views of sample holders.

In an embodiment, sample 206 is interposed totally between first free end 126 and second free end 112 as shown in FIG. 20. In some embodiments, sample 206 is interposed partially between first free end 126 and second free end 112 as shown in panel B of FIG. 22. First free end 126 or second free 112 can have various shapes independently, e.g., rectangular, rounded, and the like. Further, first eyelet 128 at free end 126 or second eyelet 118 at second free 112 can have various independent configurations, e.g., closed (as in FIG. 20) or open (as in second eyelet 118 shown in panel A of FIG. 22).

Figure 25:
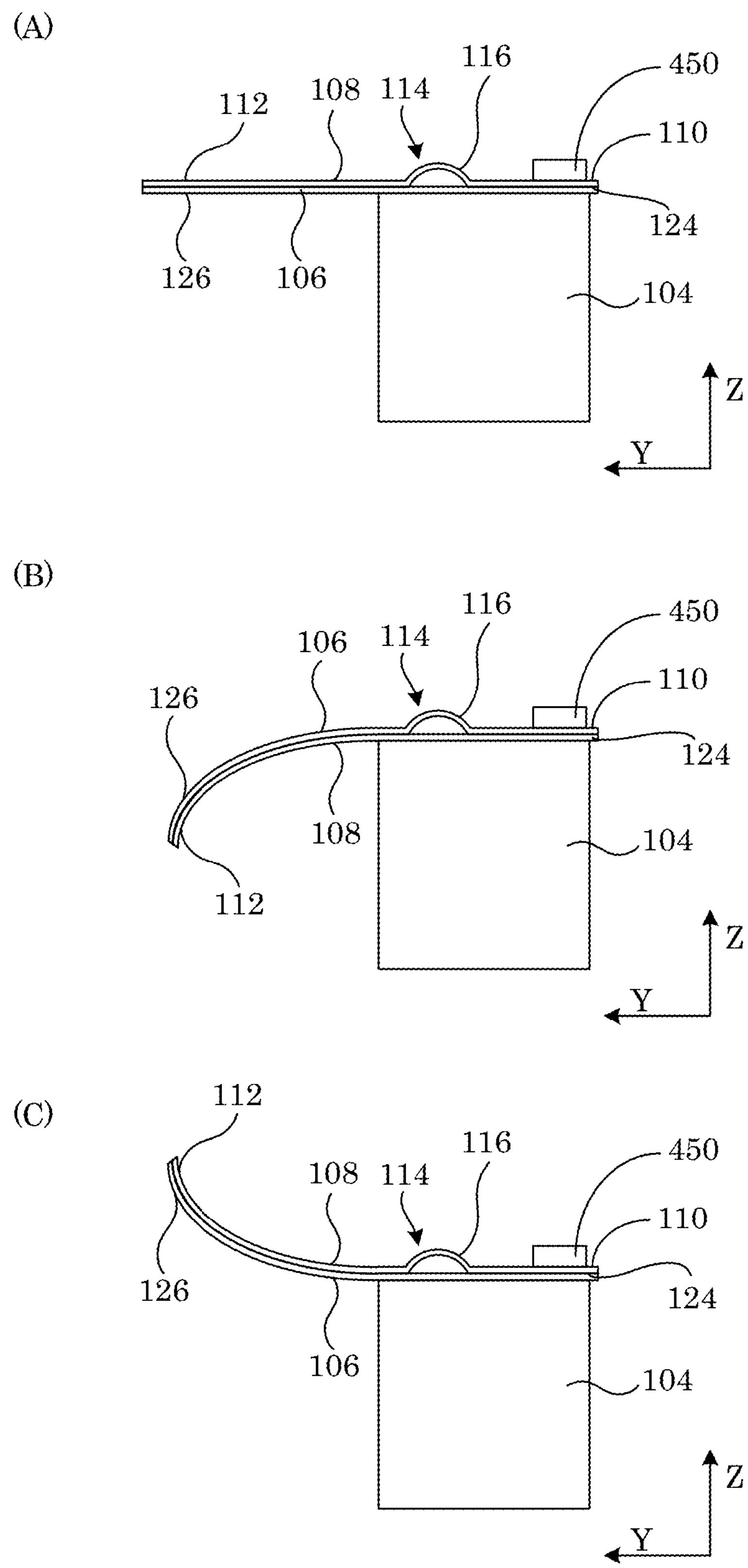
FIG. 25 shows cantilever arms of a sample holder in a relaxed position, first flexed position, and second flexed position.

Advantageously, as shown in panels B and C of FIG. 25, first free end 126 and second free end 112 of cantilever arms (106 and 108, respectively) are flexible relative to mount ends (110, 124) so that cantilever arms (106, 108) flex to not damage components in a scope if cantilever arms (106, 108) contact components in the scope such as a pole piece in an electron microscope or optics.

Figure 23:
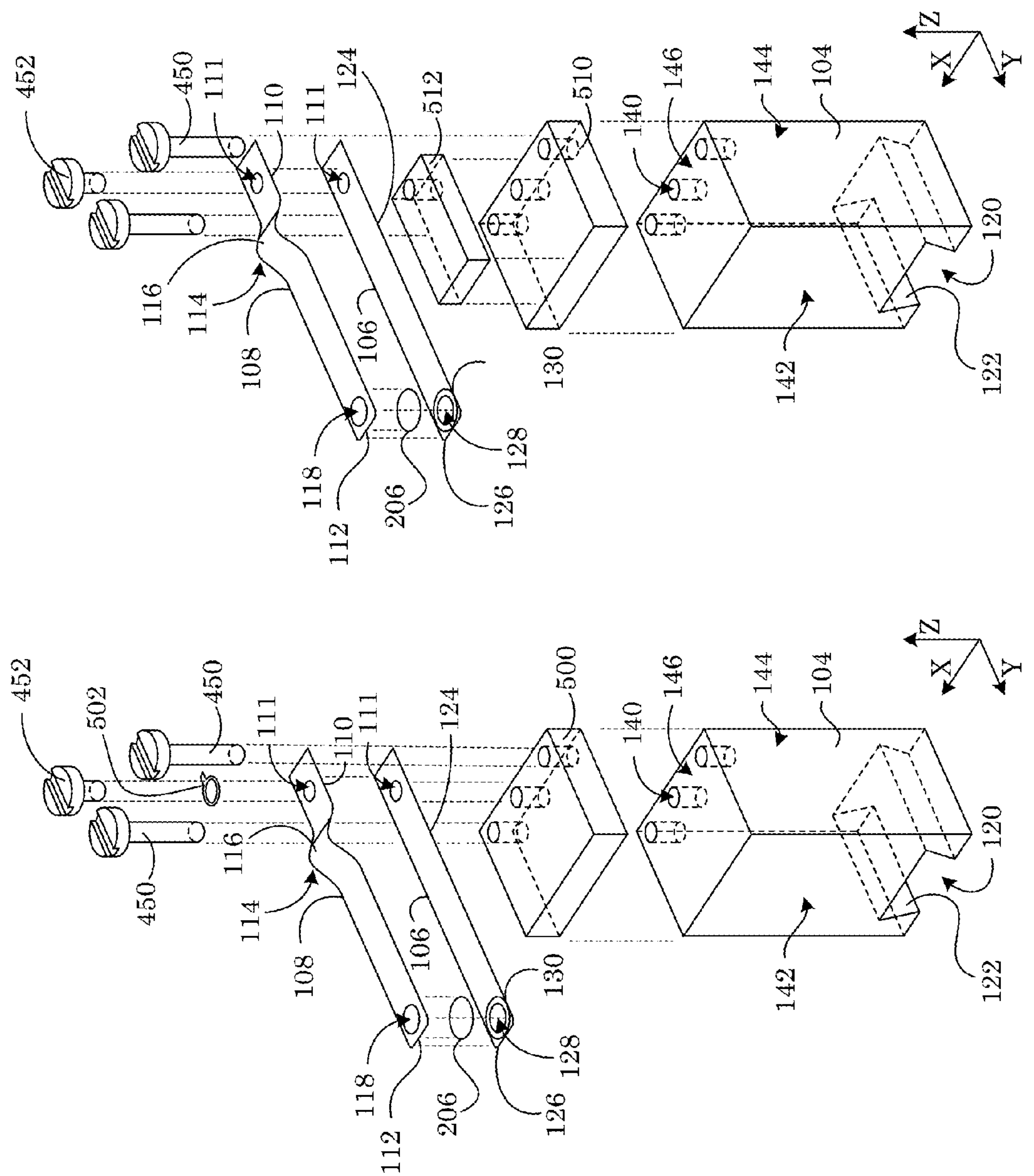
FIG. 23 shows views of exemplary sample holders.

In an embodiment, sample holder 102 provides an electrical potential to sample 206 via cantilever arm (106 or 108) as shown in panel A of FIG. 23. Here, spacer 500 is electrically nonconductive and is interposed between basal member 104 and cantilever arms (108, 106) to electrically insulate basal member 104 from cantilever arms (108, 106). Ring electrode 502 is disposed on cantilever arms (108, 106) in electrical communication therewith to provide the electrical potential thereto and attached with fastener 452 (e.g., a screw). An electrical conductor such as a wire can be connected to ring electrode 502 to supply the electrical potential.

In an embodiment, sample holder 102 heats or cools sample 206 or maintains a temperature of sample 206 via cantilever arm (106 or 108) as shown in panel B of FIG. 23. Here, spacer 510 is thermally insulating and is interposed between basal member 104 and cantilever arms (108, 106) to thermally insulate basal member 104 from cantilever arms (108, 106). Thermal member 512 is interposed between cantilever arms (108, 106) and spacer 510 to be in thermal communication with cantilever arms (108, 106) to provide temperature control of sample 206. Thermal member 512 and spacer 512 are attached to basal member 104 with fastener 452 (e.g., a screw). Heating or cooling sample 206 can be accomplished by thermal conduction through cantilever arms (106 and 108) to sample 206. Exemplary thermal members 512 include single or multi-stage thermoelectric modules, electrical resistance based heating modules, liquid nitrogen-based cold fingers, and the like.

Figure 26:
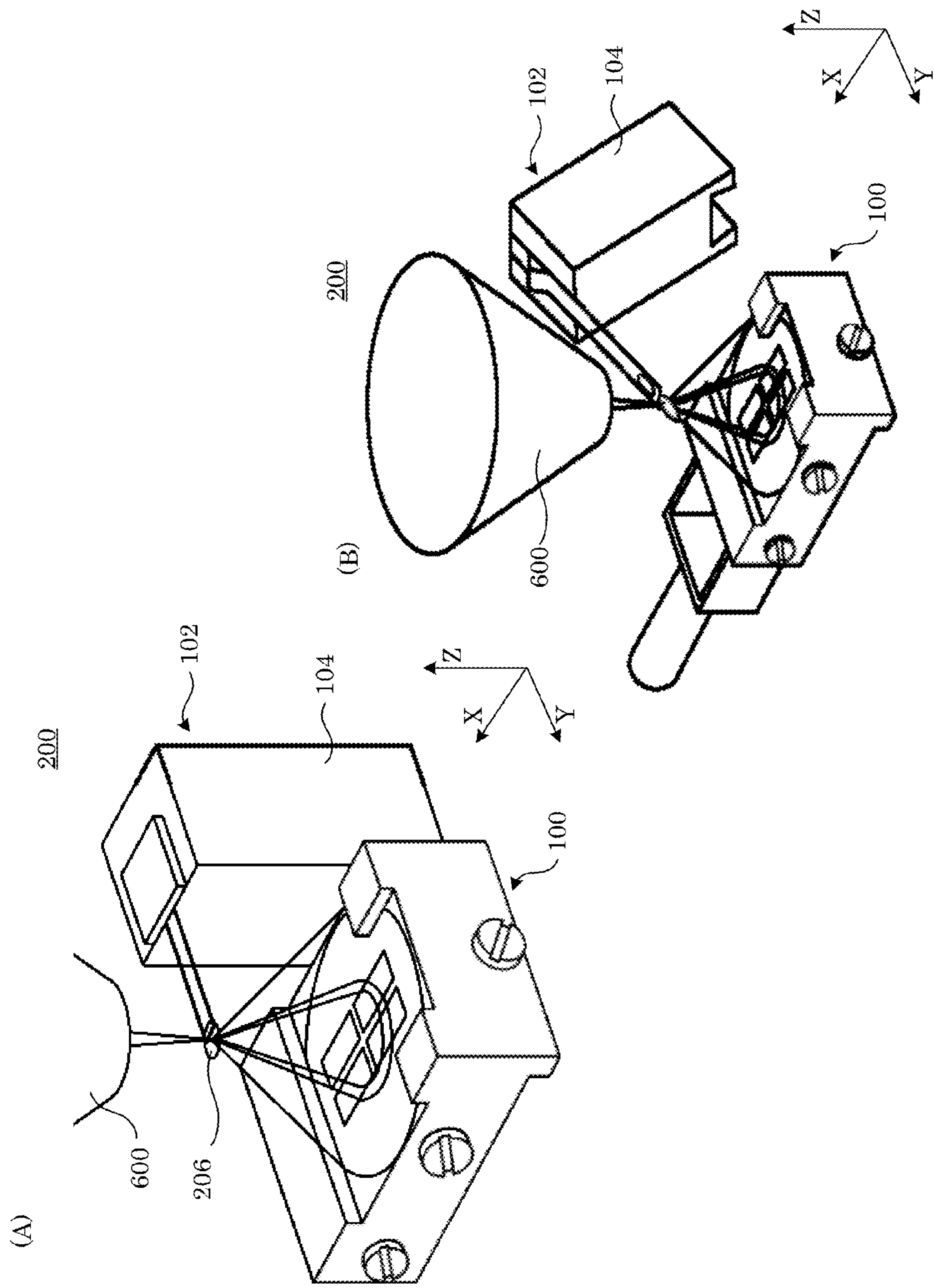
FIG. 26 shows perspective views of scope systems.
Figure 27:
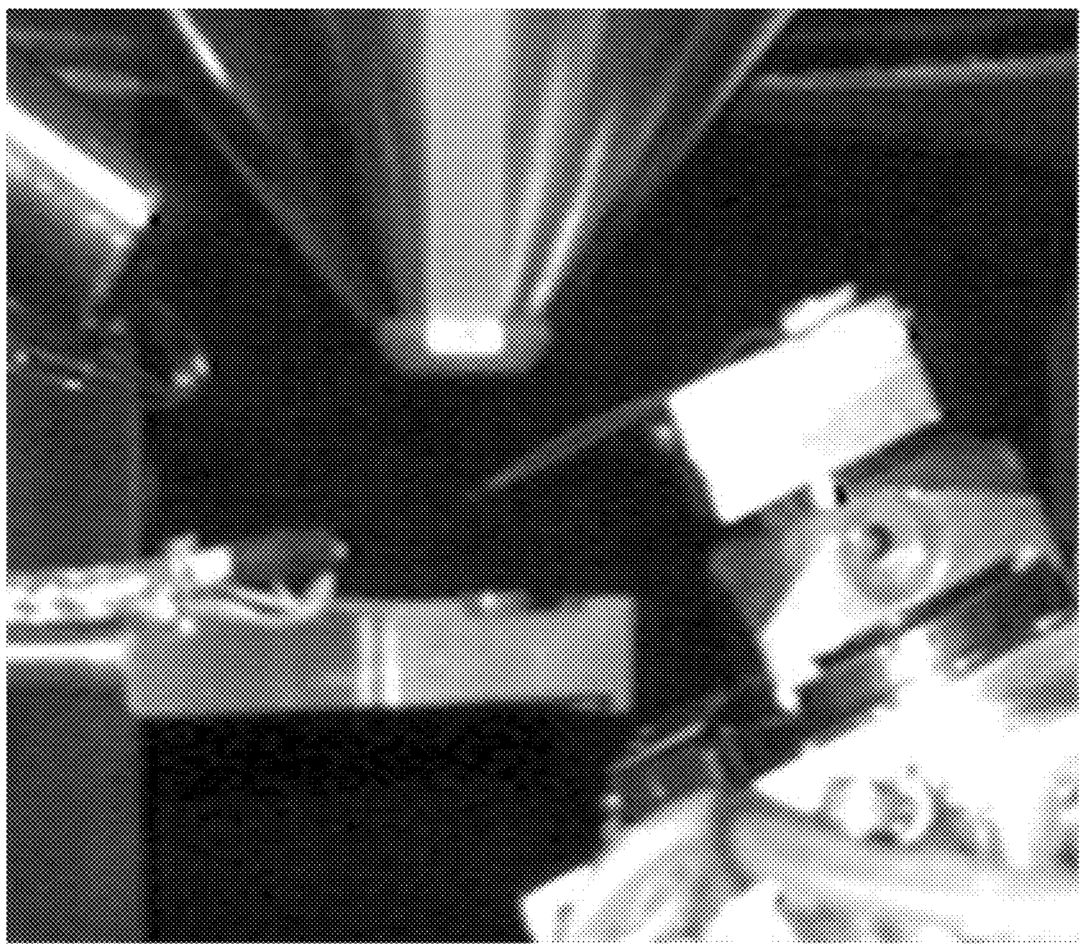
FIG. 27 shows a scope system.

In an embodiment, sample holder 102 and detector mask 100 are combined in scope system 200 as shown in FIG. 26. Here, the scope can be an electron microscope with pole piece 600 from which source particles 204 are communicated to sample 206 disposed on sample holder 102. Sample holder 102 can be disposed at an arbitrary angle relative to pole piece 600 and detector mask 100. As shown in panel A of FIG. 26, sample 206 can be orthogonal to a centerline of source particles from pole piece 600. As shown in panel B of FIG. 26 and in the photograph in FIG. 27, sample 206 can be canted (i.e., position at an oblique angle) relative to a centerline of source particles from pole piece 600.

Figure 28:
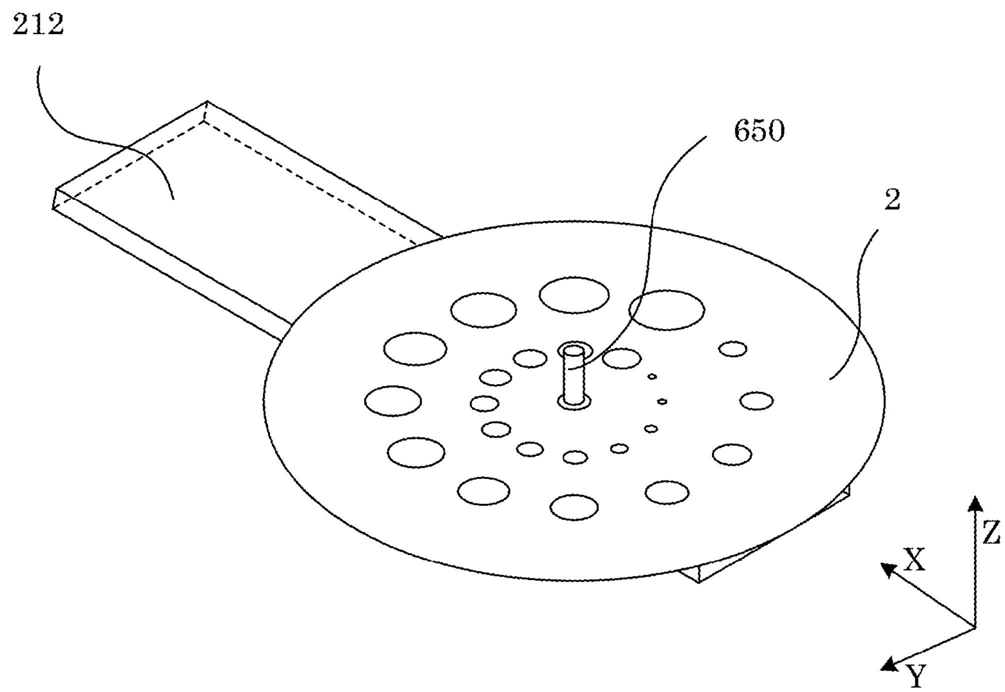
FIG. 28 shows a perspective view (panel A) and an exploded view (panel B) of a detector mask disposed on a particle detector.
Figure 28:
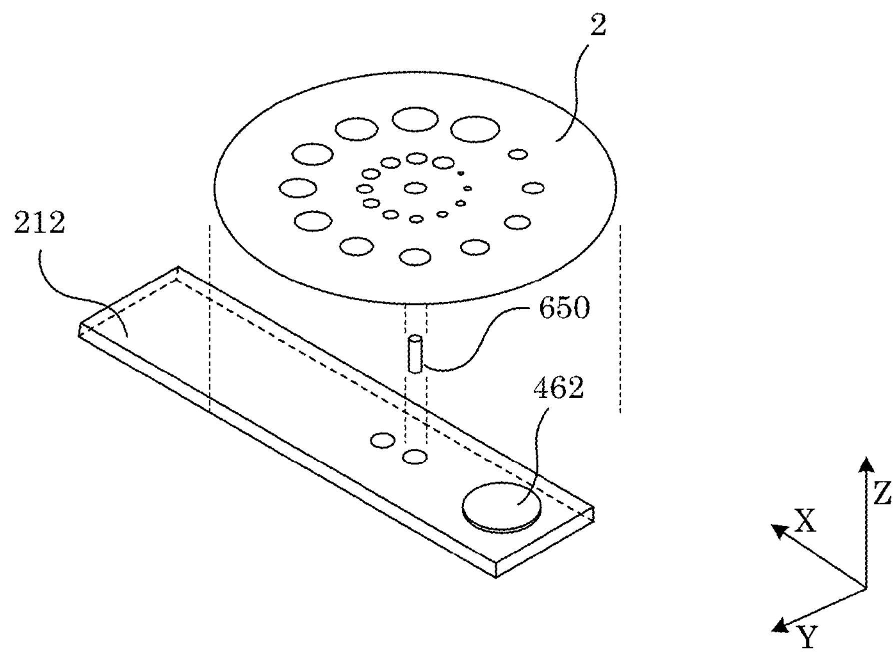

Detector mask 100 can be configured in various formats in relation to particle detector 212. In an embodiment, detector mask 100 includes plates disposed on support 400, which is disposed on particle detector 212 as shown in FIG. 17. According to an embodiment, with reference to panel A (perspective view) and panel B (exploded view) of FIG. 28, detector mask 100 includes plate 2 disposed on particle detector 212 as shown in FIG. 17, wherein plate 2 is round with transmission orifices distributed azimuthally about the center of rotation of plate 2. Here, plate 2 is attached to detector 212 with spindle 650 that provides rotary motion to plate 2 such that a particular transmission orifice among the plurality of transmission orifices is selected to cover active area 462 of detector 212.

Figure 29:
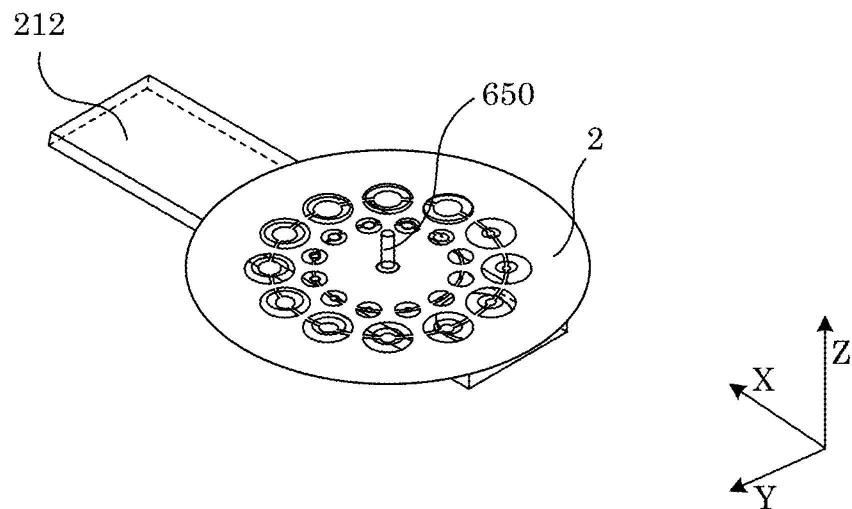
FIG. 29 shows a perspective view (panel A) and an exploded view (panel B) of a detector mask disposed on a particle detector.
Figure 29:
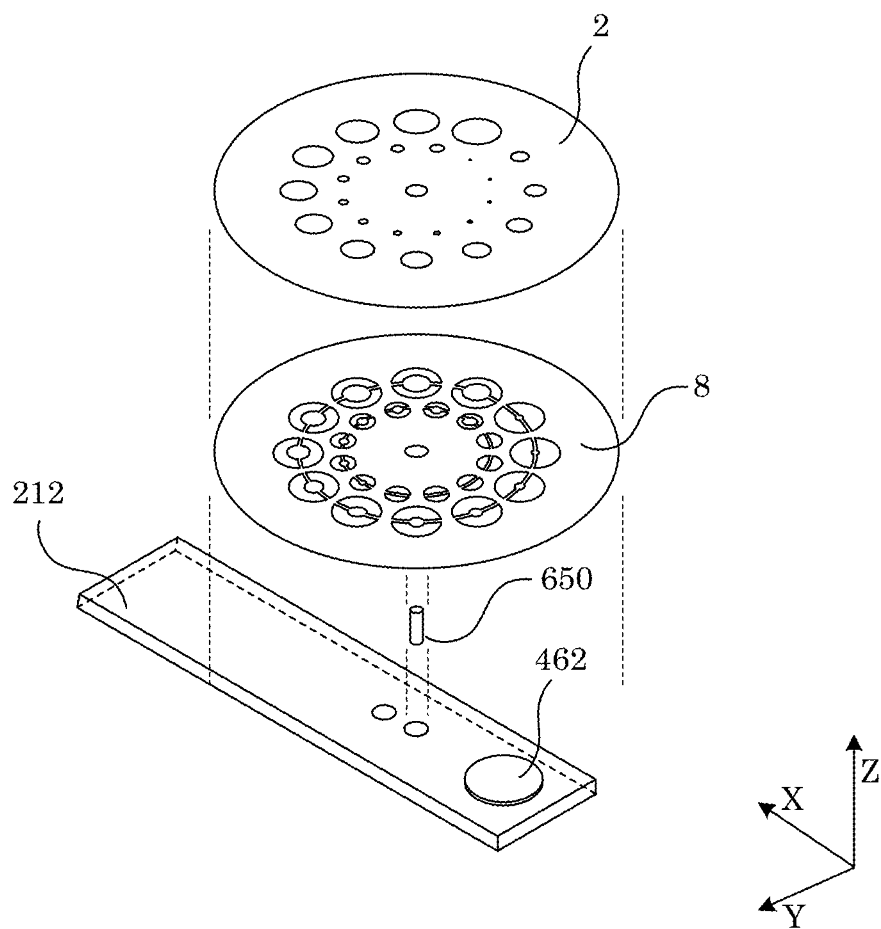

A plurality of plates can be included in detector mask 100 as shown in FIG. 29 in which first plate first plate 2 rotates independently of second plate 8 such that any permutation of first transmission orifices of first plate 2 and second transmission orifices of second plate 8 can be selected to form a desired mask transmission profile for communication of probe particles to active area 462 of particle detector 212.

In sample holder 102, basal member 104 offsets sample 206 from a positioning stage in a scope such that sample 206 can be placed between an electron pole piece of the scope and particle detector 212, wherein sample 206 can be tilted to different orientations relative to source particles such as an incident electron beam or other probe. Basal member 104 includes a non-magnetic, rigid, electrically conductive, metallic block (e.g., brass, bronze, aluminum, copper, and the like) with appropriate mating connection (e.g., a female dovetail) from which sample holder 102 connects, e.g., to a microscope sample positioning stage. Several threaded holes for mounting different articles are included at the top surface of basal member 104.

The articles and processes herein are illustrated further by the following Examples, which are non-limiting.

EXAMPLES

Example 1

It is contemplated that scope system 200 can include an off-the-shelf, retractable, solid-state scanning transmission electron microscopy (STEM) detector to image sample 206 in practically any STEM mode. Here, sample holder 102 and detector mask 100 provide a large camera length (CL) range and different ways to control and refine collection angles of particle detector 212 (and hence image contrast) in a microscope with no post-sample lenses. Images were recorded with and without detector mask 100 at different CLs. Unexpectedly advantageous contrast changes were acquired. Other transmission detectors and SEMs can be used with scope system 200.

In Example 1, SEM micrographs were generated using a Zeiss LEO 1525 Field Emission SEM equipped with a Robinson backscattered electron detector, and a KE Developments retractable bright- and dark-field SEM STEM detector (commercially available from Deben UK Ltd.). In addition to coarse insertion/retraction control, the STEM detector has an xyz-positioning stage that can be used to align the particle detector with the optic axis. The ±5 mm vertical range of the STEM detector allows the detector-to-pole piece distance to be adjusted from approximately 10 to 20 mm.

FIG. 17 shows the end of the transmission detector that is positioned below the sample. In the detector a U-shaped channel attached to the end of a cylindrical support arm holds two rectangular detector plates in the detector housing. The upper detector plate has four 2.75 mm×5.4 mm rectangular diodes located ~1 mm below the top surface of the u-shaped channel. The four diodes are symmetrically arranged around a ~100 μm diameter hole that passes through the upper plate, and are typically used to generate dark-field images. Spacing between the diodes is approximately 600 μm. The 100 μm diameter through-hole allows electrons to pass to a lower detector plate, where a fifth diode is located and used as a bright-field detector.

The support of the detector mask rests directly on top of the transmission detector U-channel as shown in FIG. 26. Plates with transmission orifices of diverse transmission profiles can be employed, and transmission orifices are not limited to being centered over the through-hole in the upper detector plate. For example, FIG. 18 shows several transmission orifices fabricated in different plates. The central plate shown in panel B of FIG. 18 shows one example of how different transmission orifices can be located over each of the detector diodes. For example, multiple transmission orifices for BF imaging can be positioned over the top right diode in FIG. 18, and transmission orifices of other geometries can be placed over the other diodes. This way, a single mask enables at least five different imaging modes. A modular approach can also be implemented as shown in FIG. 18. Here, different transmission orifices can be stacked in the support of the detector mask to collect electrons scattered through different angular ranges. By stacking two plates with different transmission orifices, a variable-annulus mask transmission profile is provided. For example, in the detector mask, a plate with a 3.1 mm outer diameter stacked on another plate having a 3 mm inner diameter effectively creates a detector mask with a 0.05 mm-wide annulus for the mask transmission profile. Stacking plates can occur over individual diodes to allow ADF imaging at very small or narrow detector acceptance angles. A variable-annulus transmission profile is produced in this manner, and thin annular detection modes are accomplished, which improves image resolution in imaging. To switch between transmission orifices and imaging modes, the transmission detector xyz-translation stage is used to align the desired transmission orifice and detector diode with the optic axis. Neighboring diodes can be shut off or masked so electrons scattered through angles sufficiently large to pass through unused off-axis transmission orifices can be excluded from the image formation process.

Plates for detector masks can be fabricated in several ways. One way is to poke a hole through or scratch an annular opening in a piece of aluminum foil that is sufficiently thick to prohibit electrons from reaching the transmission detector. The foil can then be folded over the STEM detector. Focused ion beam milling or photoetching techniques can also be used to fabricate geometrically complex transmission orifices or a set of masks with incrementally varying transmission orifices.

To extend the detector collection angle range attainable with the detector mask and to provide sample positioning and orientation for conventional transmission electron imaging techniques, sample holder, e.g., as shown in panel A of FIG. 26, is included in the scope system. Samples, which are not limited to 3 mm diameter support grids, are held between two thin pieces of metal attached to the top of the basal member as cantilever arms. The basal member includes a female dovetail in the bottom of the basal member to attach the sample holder to an SEM sample positioning stage. This configuration allows the sample to be positioned at nearly any location or orientation in the vacant space between the transmission detector and the pole piece. It also allows the sample to be positioned very close to the detector mask to provide large detector collection angles. Extraneous vibration associated with the cantilever arm (beyond vibration already inherent to the microscope and its environment) is not noticeable in images displayed on the monitor or in digitally-recorded images. The sample holder provides a measure of instrument protection since the cantilever arms flex if they contact the pole piece, the transmission detector, or the detector mask. Moreover, self-supporting samples or sample support grids can be clamped at their edges to minimize or eliminate shadowing effects due to the sample holder.

Figure 30:
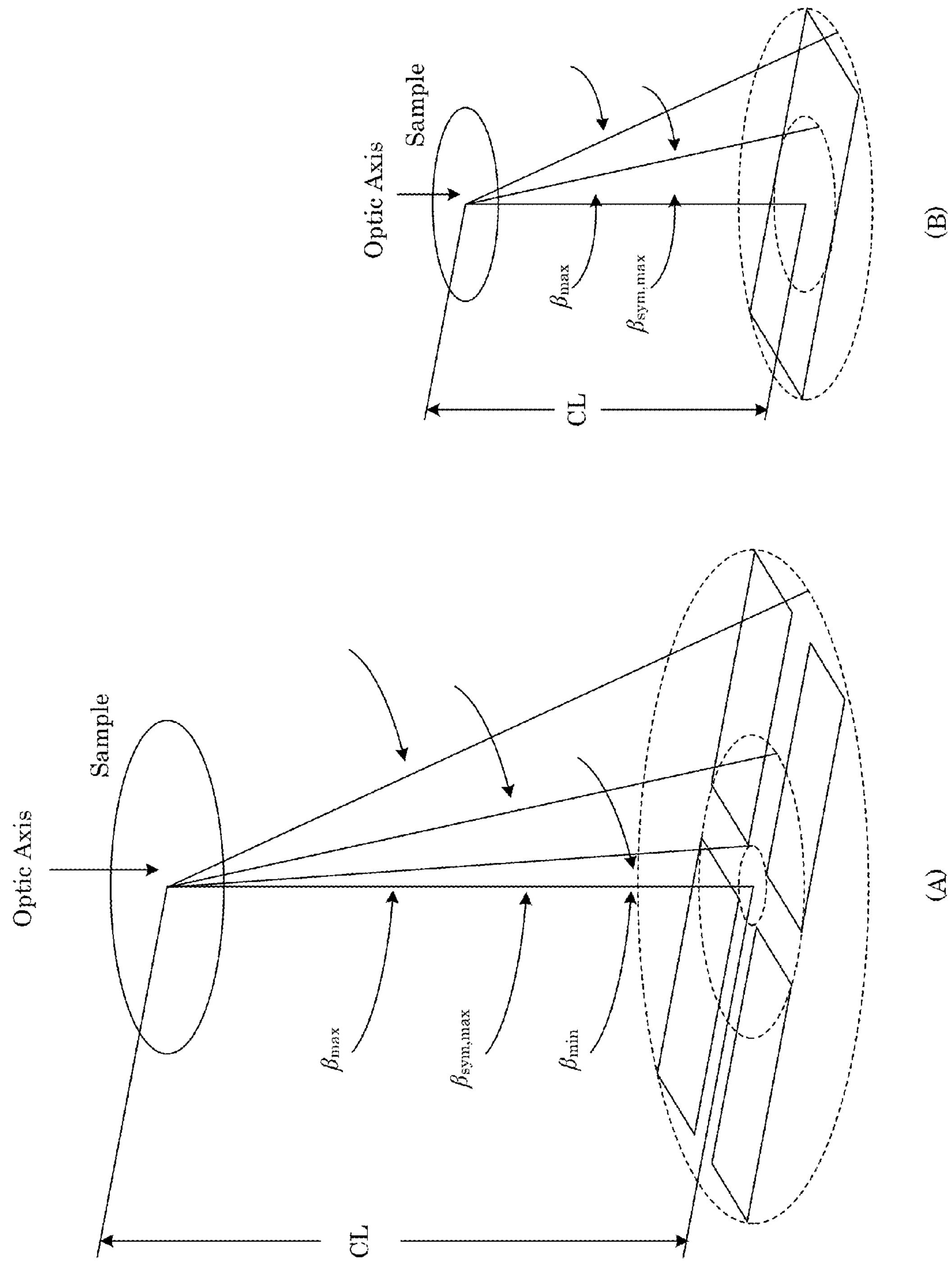
FIG. 30 shows a detector according to Example 1.

The transmission detector provides BF and DF imaging. Some conventional electron microscopes have detectors with collection angle control limited in part by the small CL range (~3-5 mm) allowed by a carousel-style holder. The sample holder herein increases the range of CL and acceptance angle for a particle detector such as the transmission detector used in Example 1. For example, when the lower detector plate is used for BF imaging, the acceptance half-angle collection range is from 10 milliradians (mrad) to 20 mrad with the carousel-style holder, but this range increases with the sample holder in an absence of the carousel-style holder. Several collection half-angles for the rectangular diodes on the upper detector plate are shown in panel A of FIG. 30 in which the upper detector plate with four diodes is shown with respect to camera length (CL) and detector collection half-angles, β. Panel B shows similar information for a single diode. With the sample holder herein, the range of minimum collection half-angles, $\beta_{min}$, for all four diodes on the upper detector plate is approximately 20-300 mrad, and the range of maximum collection half-angles, $\beta_{max}$, is approximately 365-1400 mrad. Another collection half-angle, $\beta_{sym,max}$, also is shown in FIG. 30. Collection angle $\beta_{sym,max}$ is the collection angle that corresponds to a largest radius at which the effective area of the detector is radially symmetric or approximated as radially symmetric. Collection angle $\beta_{sym,max}$ can be from 150 mrad to 1250 mrad when the four upper plate diodes are used and centered on the optic axis as shown in FIG. 30 and is from 0 mrad to 900 mrad when a single diode is centered on the optic axis as shown in FIG. 30.

The sample holder and the positioning stage integral to the STEM detector provides BF and DF imaging with any the four upper detector plate diodes, and the equivalent of displaced-transmission orifice DF imaging using the lower detector plate. For example, displaced-transmission orifice DF images can be obtained by using the transmission detector xyz-positioning stage to center the 100 μm through-hole at a desired location off the optic axis. When a single diode is used, the inner collection half-angles can be small for ADF and ABF imaging. Advantageously, the 4-diode upper detector plate provides BF and DF imaging such that the lower detector plate can be removed. As a result, other hardware can be placed below the transmission detector. In this manner, electron energy loss spectroscopy (EELS) or simultaneous transmission imaging in a conventional SEM can be performed.

Using the Sample Holder Without the Detector Mask.

Figure 31:
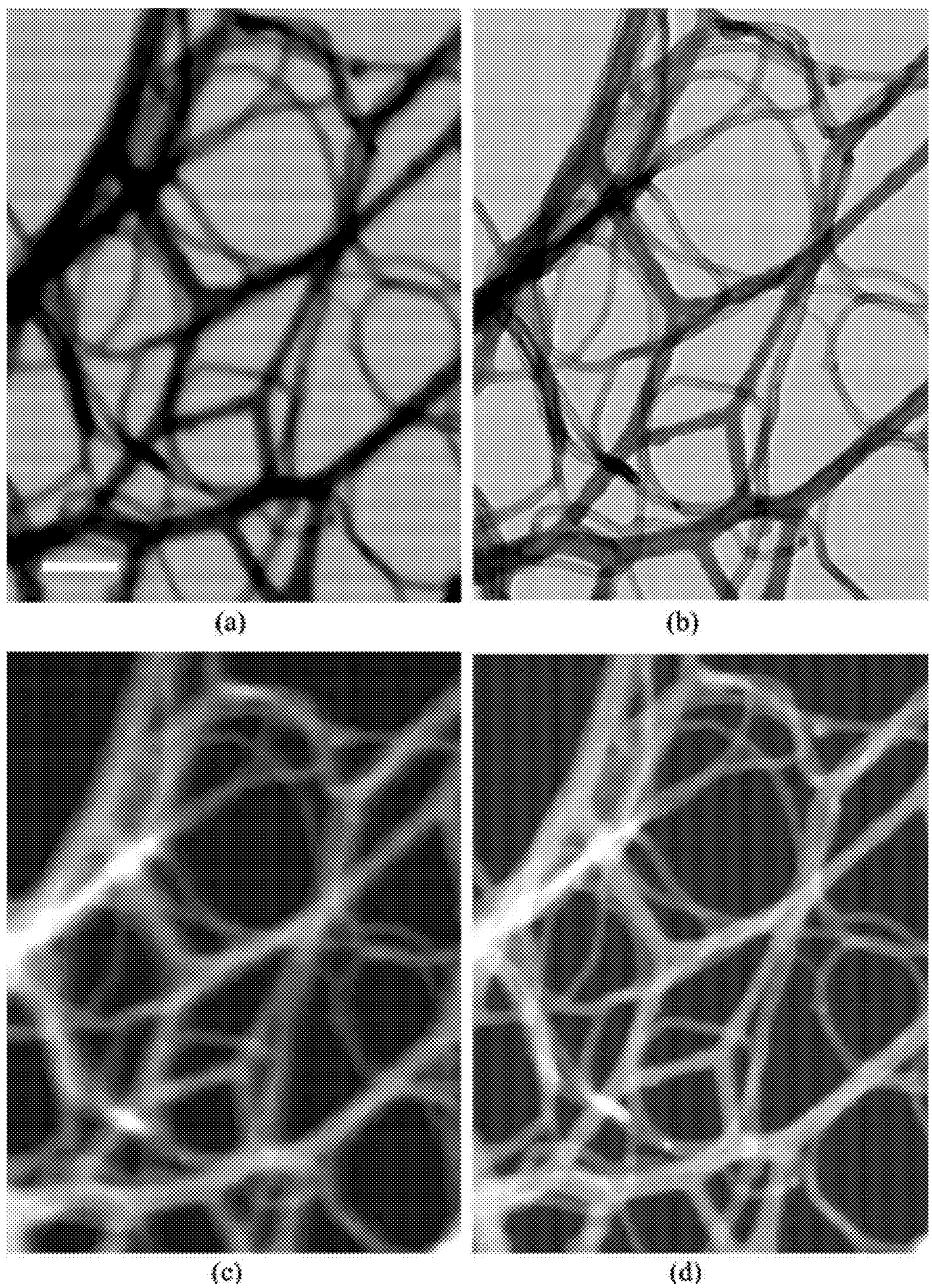
FIG. 31 shows micrographs of multi-wall carbon nanotubes according to Example 1.

With the ~1-20 mm CL range enabled by the sample holder, a wider range of acceptance angles at the detector is available and improvements in imaging occur. FIG. 31 shows several images of multi-wall carbon nanotubes (MWCNTs) on a lacey carbon substrate recorded at short and long CLs in an absence of the detector mask. Here, STEM-in-SEM images of MWCNTs show the effect of changing CL when the transmission detector is used without the detector mask, wherein BF images were recorded at 5.1 mm CL (panel A) and at 18 mm CL (panel B), and DF images were recorded at 3.1 mm CL (panel C) and at 18 mm CL (panel D). Primary electron energy was 30 keV with a 30 μm condenser aperture. The scale bar in panel A is 100 nm long. Again, panel A shows a BF image obtained at CL=5.1 mm (β≈12.5 mrad), which is close to the maximum CL available with the carousel-style sample holder. MWCNT edges are not easy to discern, and a well-focused, sharp image is not easy to achieve. However, when the CL=18 mm (β≈3 mrad) as shown in panel B, image features are sharper. MWCNTs can be distinguished from the lacey carbon, and inner and outer tube edges are discernable in most tubes. Panels C and D show DF images recorded with the entire 4-diode array at camera lengths of 4 mm ($100<\beta<1000$ mrad) and 18 mm ($25<\beta<350$ mrad), respectively. No tube walls are readily apparent in panel C, and tubes are difficult to discern form the lacey carbon substrate. In panel D, inner and outer tube edges (not individual tube walls) are discernable as thin white lines in some tubes, but MWCNTs are not easily distinguished from the lacey carbon substrate.

Figure 32:
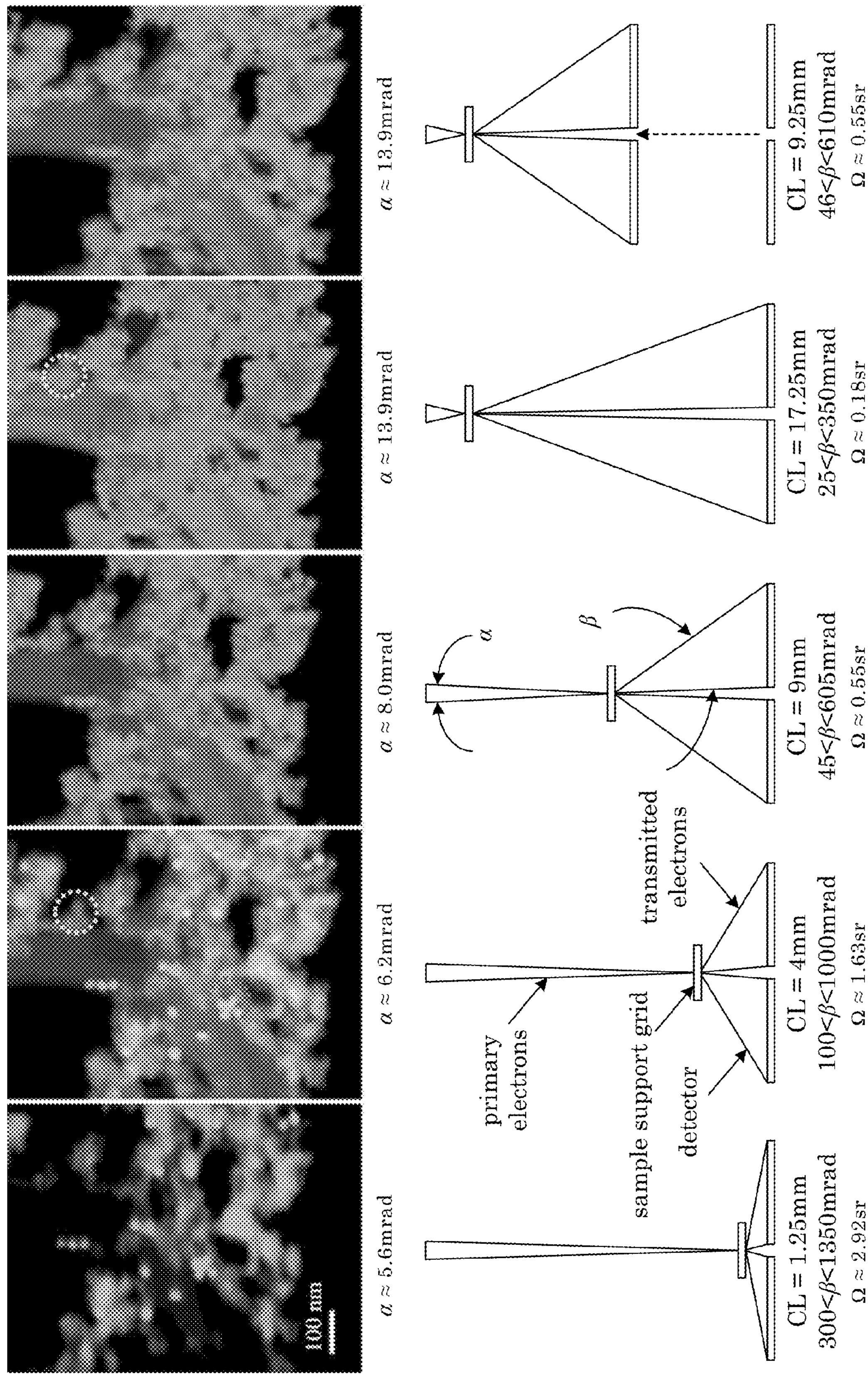
FIG. 32 shows dark-field micrographs of 30 nm diameter Au and $TiO_2$ particles on a lacey carbon substrate recorded at different camera lengths (upper panels) and also shows in lower panels the camera length (CL) at which the micrographs were recorded.

Mass-thickness contrast can be observed in DF images using all four upper plate diodes without the detector mask. FIG. 32 shows several micrographs of 30 nm diameter Au particles and 30 nm diameter $TiO_2$ particles on a lacey carbon substrate. Primary electron energy for these images was 30 keV, and a 30 μm diameter condenser transmission orifice was used. The same detector gain settings were used for all five images. From left to right, the micrographs were recorded at CLs of 1.25 mm, 4 mm (typical of the carousel style holder), 9 mm, 17.25 mm, and 9.25 mm. Other imaging conditions (i.e., beam convergence half-angle, a, detector collection half-angle, β, and effective detector solid angle Ω) are shown in the accompanying lower panels in FIG. 32. When imaged at short CLs (e.g., 4 mm), individual Au particles (circled in red) exhibited stronger contrast relative to the background black level than individual $TiO_2$ particles (circled in green) and the carbon substrate. Unexpected results are observed at longer CLs. For example, the Au particles and the $TiO_2$ agglomerates both exhibited a change from bright intensity at 4 mm CL to less bright at 9 mm and 17.25 mm CLs, whereas the carbon substrate became increasingly brighter with increasing CL. Note that in the image recorded at 17.25 mm CL, the Au particles are much darker than the $TiO_2$ and most of the lacey carbon. In particular, at the longest CL all the Au particles exhibit a dark central region surrounded by a brighter ring. Thicker regions of the $TiO_2$ agglomerates also exhibit weaker contrast with respect to the background black level at 17.25 mm than at 4 mm.

The brightness changes exhibited with CL changes in FIG. 32 are based on mass-thickness scattering effects. First, there is the mass or atomic-number effect associated with Rutherford scattering: 30 nm diameter Au particles will likely scatter more electrons through a larger angular range than 30 nm diameter $TiO_2$ particles, and the $TiO_2$ particles will likely scatter more electrons through a larger angular range than the lacey carbon substrate. Second, there is the material thickness effect, as exhibited by the fact that as the CL is increased, brightness reduction begins at the projected particle centers or the thickest regions of the agglomerates. Primary electrons with initial trajectories through particle centers (i.e., thicker regions) are likely to scatter more often as they pass through a particle than primary electrons with incident trajectories through particle edges (i.e., thinner regions). Scattering more often (i.e., the thickness effect) and through larger angles per scattering event (i.e., the mass or atomic-number effect) means that for homogeneous samples of constant thickness, the forward-scattered electron angular distribution will likely be wider for materials of greater atomic number. Therefore, if the CL is increased but everything else is held constant, a larger effective detector area will be required to collect the same number of electrons necessary to provide the same image contrast as that observed at shorter CLs. In other words, electrons scattered through angles larger than the detector is able to collect cannot contribute to the image. At short CLs, the vast majority of electrons forward-scattered by the Au and $TiO_2$ can be collected and the image may be bright where those materials exist. As the CL is increased, a reduction in brightness will occur for the Au before the $TiO_2$ since 30 nm Au particles will tend to scatter electrons over a larger angular range than 30 nm $TiO_2$ particles.

The primary electron beam convergence half-angle, α, can affect image contrast. In the first four images of FIG. 32, the detector was held at a constant position as the sample was moved closer to the pole piece. Maintaining focus at the sample as it is moved closer to the pole piece included increasing the beam convergence angle when the same beam condenser transmission orifice was used. α varied from 5.6 mrad to 13.9 mrad as shown in the FIG. 32. The convergence angle was not a strong contributor to the brightness changes. Without changing focus conditions at the sample, the detector was moved closer to the pole piece so that the new CL was 9.25 mm as shown in the right-most image of FIG. 32. Notice that the various brightness levels exhibited in the rightmost image are similar to those of the third image which was recorded with nearly identical acceptance angles. The difference between the two imaging conditions was beam convergence angle. Therefore, the beam convergence angle plays a minimal role in the observed image contrast changes under these conditions.

Figure 33:
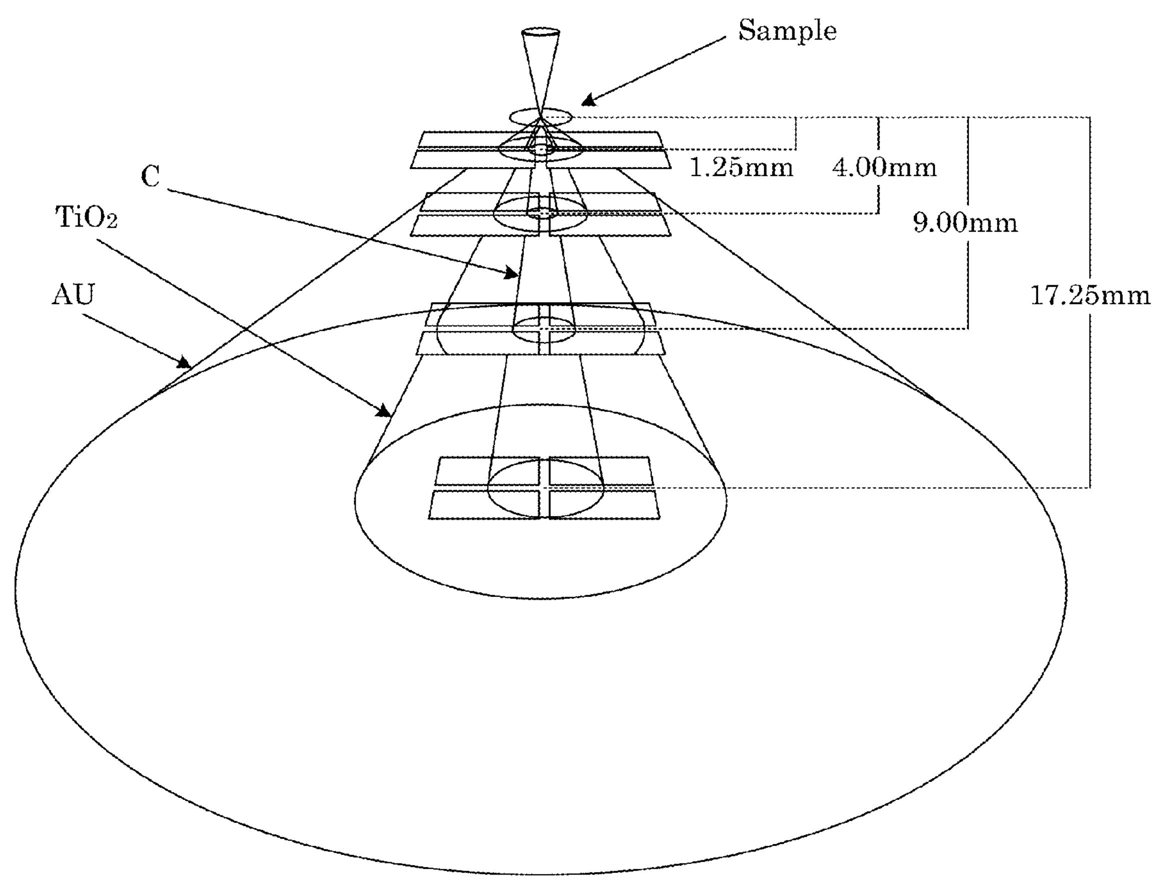
FIG. 33 shows a four-diode upper plate detector with a relationship between electron scattering angles of different materials and effective detector area at different CLs, wherein cones for forward-scattered electron distributions of the materials shown in FIG. 32 are colored dark gray (carbon), light gray ($TiO_2$) and gold (Au)

FIG. 33 shows, at different CLs in an absence of the detector mask, the fraction of scattered electrons hitting the detector can be different for different materials. The CL increases from short to long, and the fraction of detected electrons that are scattered from different materials in the sample pass through maximum values at different camera lengths and decrease because of the finite detector geometry. Those maxima reflect a combination of scattering angle, detector geometry, and effective detector solid angle. For example, assume that the electrons scattered from different materials can be represented by cones as shown in FIG. 33. When the CL is 17.25 mm, a large fraction of the electrons scattered by the carbon can be collected, but only a small fraction of the electrons scattered by the Au can be collected. Hence, the carbon substrate can exhibit the brightest regions in an image while the Au may be darker. At the 4 mm CL, a much larger fraction of electrons forward-scattered by the Au and $TiO_2$ can be collected, but the carbon signal will be much weaker because of the 600 μm gap between detector elements. Image contrast can be biased from low-Z materials to high-Z materials regardless of the 600 μm gap simply by taking advantage of the large CL range that the sample holder enables. Although unexpected brightness or contrast changes can occur, qualitative image interpretation may still be straightforward in many cases by simply changing the CL and observing how the contrast changes.

Imaging with a Collection Angle-Defining Detector Mask.

With the detector mask in place and the extended CL range enabled by the sample holder, full control over transmission detector collection angles is possible within the detector geometry and transmission mask profile limits. Calculating detector collection half-angles, effective detector areas, and effective solid angles created by the detector mask is more complex than calculating those parameters when the mask detector is absent because the plates have finite thickness, and the detector diodes are positioned approximately 1 mm below the top of the U-channel. As shown in panel A of FIG. 34, the detector area exposed to scattered electrons may not lie directly beneath transmission orifice but may be radially offset outward, depending on the collection angles established by H and the transmission profile.

Figure 34:
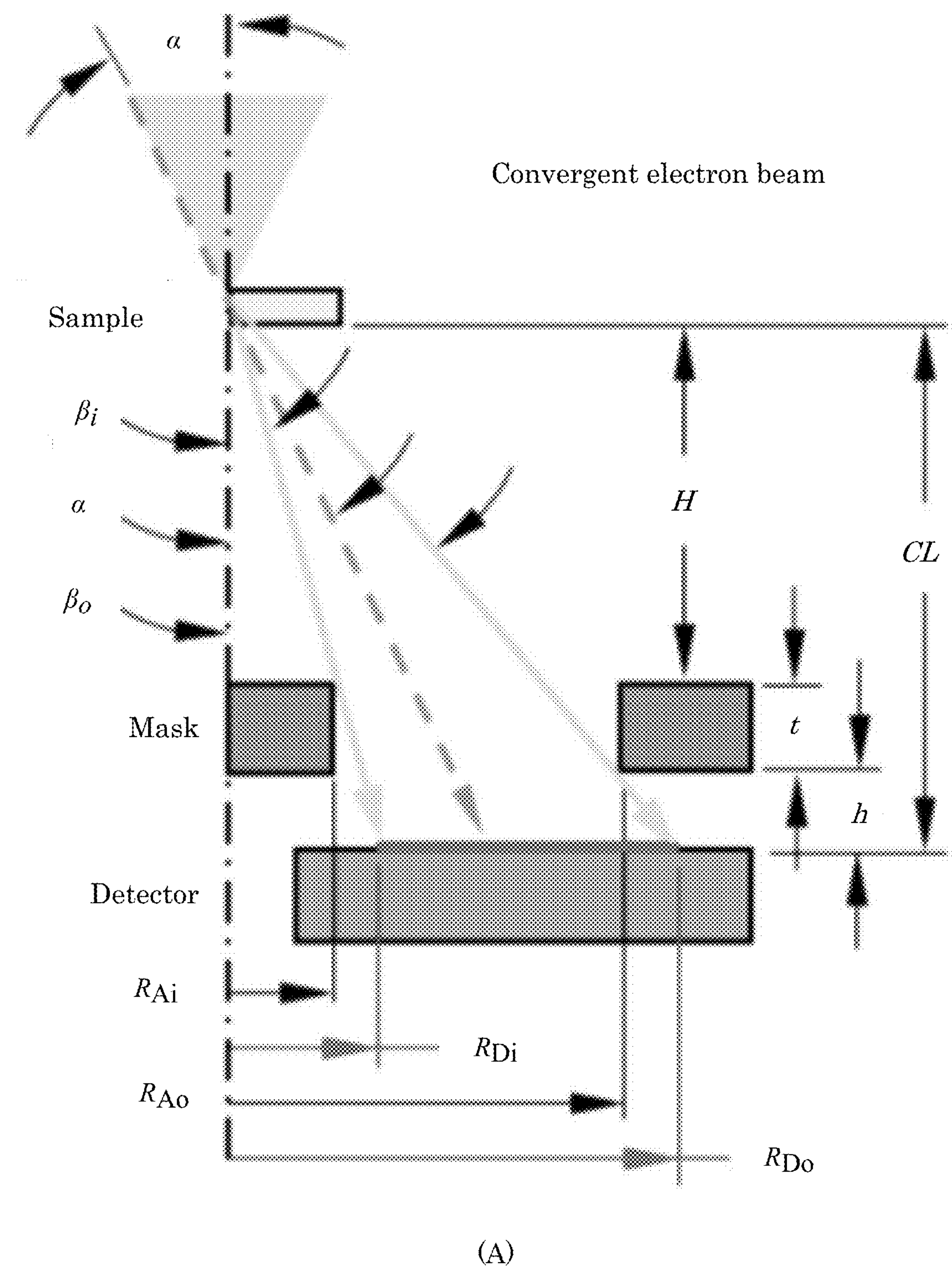
FIG. 34 shows a relationship between geometry of plates of a detector mask, sample-to-detector distance, and effective detector geometry according to Example 1, wherein panel A shows parameters to calculate effective collection angles and detector range, and panel B shows a 4-diode upper detector plate with radially asymmetric rectangular diode geometry and two effective detector areas created by plates of the detector mask with annular transmission profiles; red areas are exposed to transmitted electrons and contribute to the detector signal; gray areas are non-detecting regions, and white areas are masked diode regions.

Panel B of FIG. 34 shows two slightly different effective detector geometries when transmission orifices of plates of the detector mask have annular transmission profiles centered over the four-diode upper detector plate. The top panel shows a configuration with effective detector radii $R_{Di}$=1 mm and $R_{Do}$=2 mm, the bottom panel shows a configuration with effective detector radii $R_{Di}$=2 mm and $R_{Do}$=4 mm. The red areas represent diode regions exposed to electrons that contribute to the detector signal, gray areas represent non-detecting regions exposed to electrons, and white areas represent masked detector regions. Note that as the effective detector radii increase beyond ≈3 mm, effective detector areas shown in red become increasingly radially asymmetric.

As shown in panel A of FIG. 34, parameters to calculate effective detector collection half-angles, detector areas, and solid angles based on a single plate in a detector mask are the inner and outer transmission orifice radii, $R_{Ai}$ and $R_{Ao}$, the sample-to-plate distance, H, the plate thickness, t, the distance between the bottom of the plate and the top of the transmission detector diodes, h, and the detector diode geometry and layout as shown in panel B, wherein CL=H+t+h. Inner and outer collection half-angles, $\beta_i$ and $\beta_o$, can be calculated as $$\beta_i=\tan^{-1}(R_{Ai}/H);\ \beta_o=\tan^{-1}(R_{Ao}/(h+t)). \quad (1)$$

Figure 35:
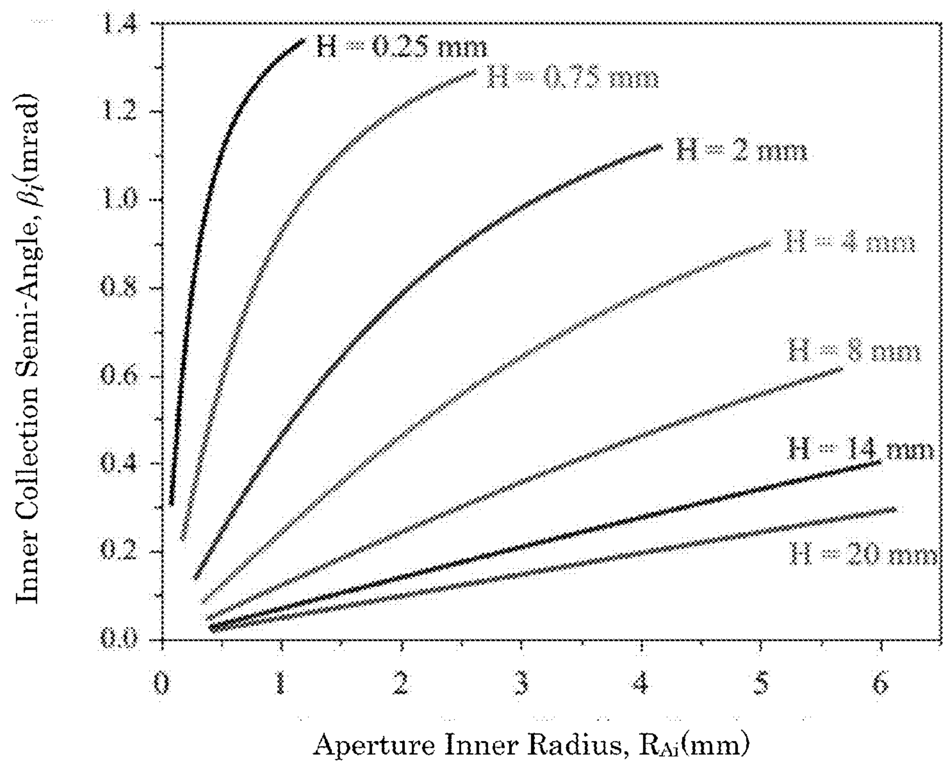
FIG. 35 shows effective detector parameters when the detector mask and the sample holder are used with a four-diode detector plate, wherein panel A shows a relationship between inner collection half-angle, $\beta_i$, aperture inner radius, $R_{Ai}$, and sample-to-detector mask distance, H, and panel B shows a relationship between effective detector radii and effective detector area.
Figure 35:
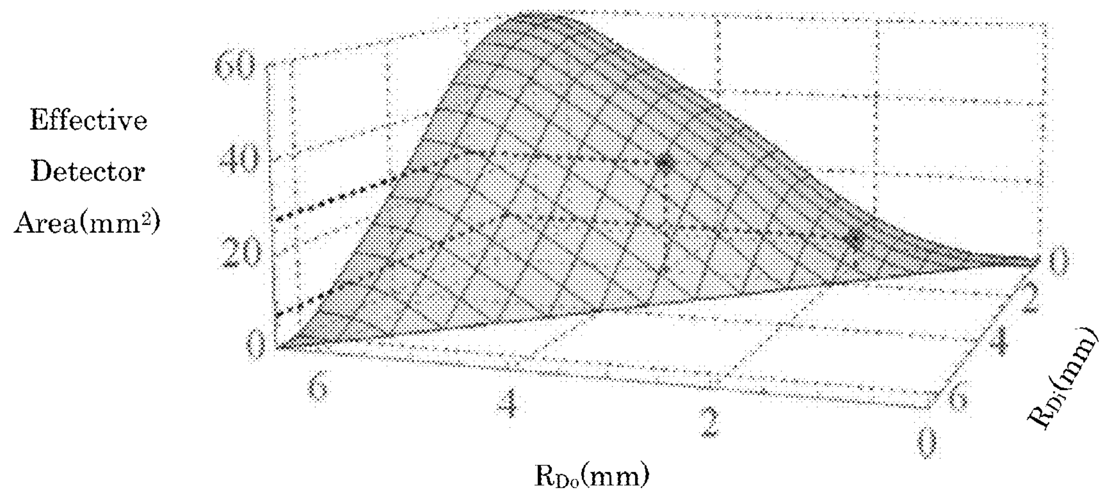

FIG. 35 shows the inner collection half-angle, $\beta_i$, as a function of inner annulus radius, $R_{Ai}$, for several sample-to-plate distances, H, and a plate thickness t=0.1 mm. Both ends of each curve are truncated due to detector diode geometry. Effective inner and outer detector radii, $R_{Di}$ and $R_{Do}$, can be determined from similar triangles in panel A of FIG. 34 as follows:

$$R_{Di}=\frac{(H+t+h)}{H}R_{Ai};\ R_{Do}=\frac{(H+t+h)}{(H+t)}R_{Ao}. \quad (2)$$

These effective radii can be used to calculate approximate values for effective detector areas and solid angles. However, accurate effective detector area and solid angle calculations account for the inactive support areas between diodes, the radially asymmetric rectangular diode geometry, and any mask structure blocking electron flux to the detector. Panel B of FIG. 35 provides a relationship between the effective detector radii ($R_{Di}$ and $R_{Do}$) and the effective detector area for the four-diode upper detector plate with those non-detecting regions taken into account.

To calculate detector parameters, we consider a mask with an annular transmission profile centered over the four-diode detector plate as shown in the top schematic of panel B of FIG. 34. For this detector and transmission orifice configuration h≈1 mm and t=0.1 mm. With a measured sample-to-plate distance H=3.9 mm, and an annular transmission profile with dimensions $R_{Ai}$=0.78 mm and $R_{Ao}$=1.6 mm, the effective detector radii $R_{Di}$ and $R_{Do}$ are 1 mm and 2 mm. The effective inner collection half-angle, $\beta_i$, is 200 mrad, and the effective outer collection half-angle, $\beta_o$, is 380 mrad. The effective detector area is 7 $mm^2$ (corresponding to one of the red dots on the surface plot in panel B of FIG. 35), and the inactive gray area shown in the upper panel of panel B of FIG. 34 is 2.42 $mm^2$.

The effective detector solid angle can be determined using different methods. One method is to approximate it by calculating a nominal active detector area and an inactive area fraction, F. For a mask with an annular detector, the solid angle can then be approximated as $$\Omega=2\pi(1-F)\left(\frac{R_{Do}^2+d^2-d\sqrt{R_{Do}^2+d^2}}{R_{Do}^2-d^2}-\frac{R_{Di}^2+d^2-d\sqrt{R_{Di}^2+d^2}}{R_{di}^2-d^2}\right). \quad (4)$$

Here, Ω is the effective detector solid angle, $R_{Do}$ (2 mm) and $R_{Di}$ (1 mm) are the effective outer and inner detector radii, and d is the sample-to-detector distance (d=CL=H+t+h=5 mm, as shown in FIG. 34). In this example, F=0.257 (2.42 $mm^2$/9.43 $mm^2$), giving a solid angle of 0.243 sr. An alternative way to determine the effective solid angle is to create a 3D solid model and project the effective detector area to an appropriate hemispherical surface. Applying the solid modeling method to the above example provides a solid angle of 0.242 sr. For larger effective detector radii (i.e., $R_{Di}$=2 mm and $R_{Do}$=4 mm as shown in the bottom schematic of panel B of FIG. 34) and the same sample-to-detector distance d=5 mm, the inner and outer collection half-angles are 380 and 675 mrad, the effective detector area is 27.3 $mm^2$, a 3D solid model provides a solid angle of 0.687 sr, and the online calculator provides a solid angle of 0.671 sr (F=10.4 $mm^2$/37.7 $mm^2$=0.276).

As mentioned previously, although the entire 4-diode array on the upper plate is used for DF imaging, the transmission detector xyz-positioning stage allows any of the four diodes to be employed individually as either a BF or DF detector. With a single diode, all BF and DF imaging modes that are possible with all four diodes, plus ABF and marginal BF imaging modes can be performed. Furthermore, information from materials and samples that do not scatter electrons multiple times or over large angular ranges (i.e., low-Z materials, sufficiently thin samples, or samples in the correct orientation for Bragg diffraction or channeling) can be collected. Moreover, employing transmission orifices smaller (or larger) than the 100 μm transmission orifice in the upper detector plate is straightforward. For example, a plate in the detector mask with a 10 μm diameter transmission orifice combined with the 20 mm of CL that the sample holder allows provides BF collection half-angles from 0.25 mrad to 5 mrad. These smaller transmission orifices can enhance image contrast.

Figure 36:
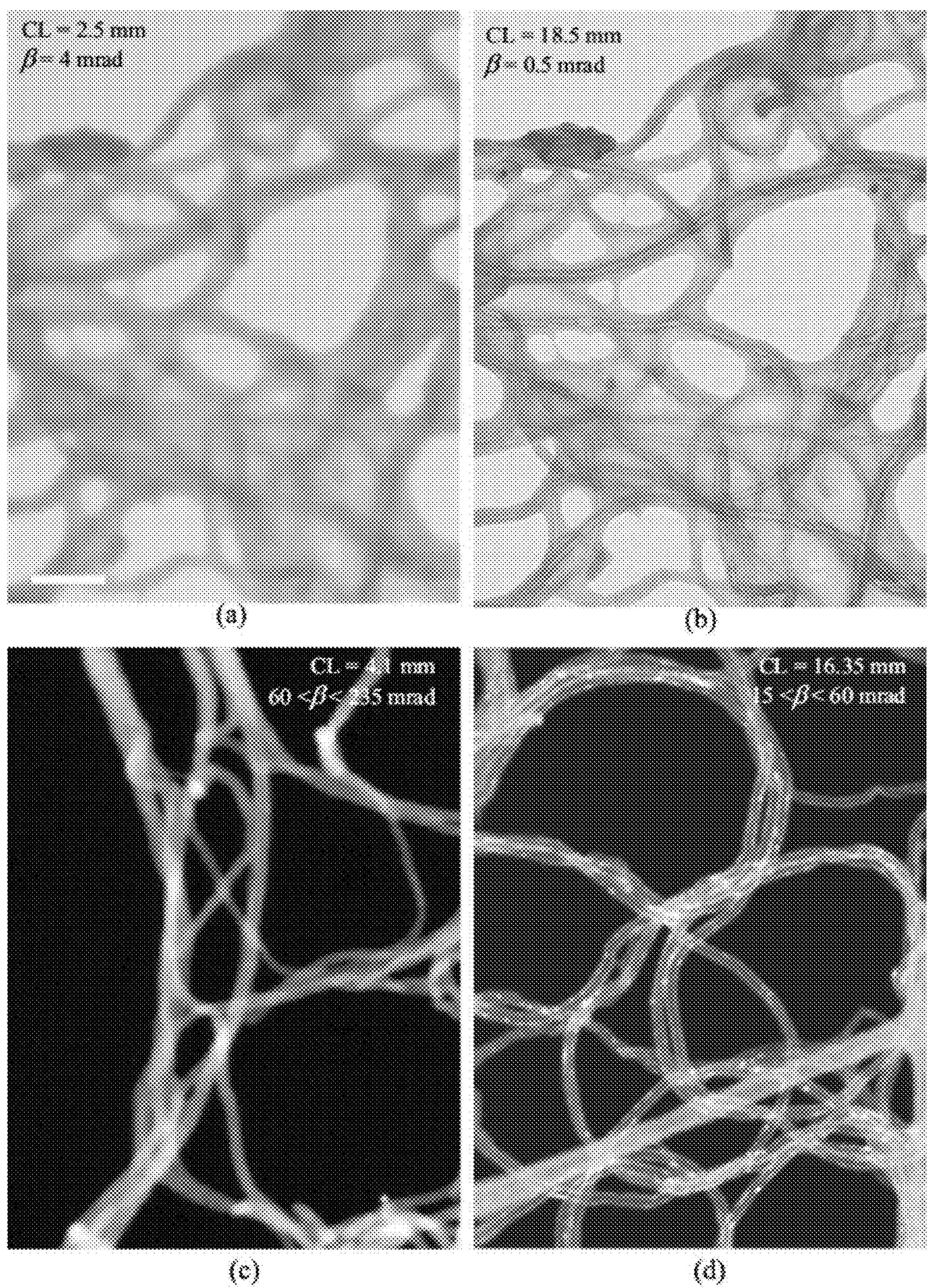
FIG. 36 shows MWCNT images recorded using 30 keV primary electrons and a 30 μm condenser aperture for BF images of MWCNTs in residual organic dispersant using a 20 μm diameter transmission orifice centered over a single detector plate diode recorded at CLs of 2.5 mm (panel A, ($\beta \approx 4$ mrad) and 18.5 mm (panel B, $\beta \approx 0.5$ mrad), and ADF images of MWCNTs dispersed in chloroform with annular transmission profile centered over a single diode recorded at CLs of 4.1 mm (panel C, $60<\beta<235$ mrad), and 16.35 mm (panel D, $15<\beta<60$ mrad); the scale bar in panel A applies to all four panels.

BF and ADF images of MWCNTs dispersed in N-methyl-2-pyrrolidone and drop-cast on a lacey carbon substrate were recorded at different CLs using one of the four upper plate diodes and are shown in FIG. 36. The BF images were recorded using a 20 μm diameter transmission orifice, and the DF images were recorded using an annular transmission profile with $R_{Ai}$=0.25 mm and $R_{Ao}$=1.0 mm, and collection half-angles and CLs are indicated in the images. As was shown in FIG. 31, BF images can benefit from the long CL. However, when an appropriate transmission orifice is used, MWCNTs within residual organic dispersant and irregularities along the lengths of the tubes are much easier to discern as panel B of FIG. 36 shows when compared to panel A of FIG. 36. Moreover, inner and outer tube diameter measurements are feasible because of the contrast improvements elicited with the transmission orifice and long CL.

Panel C and D of FIG. 36 show ADF images of MWCNTs dispersed in chloroform and drop-cast on a lacey carbon substrate. Much like the BF images, individual MWCNTs are much easier to resolve when imaged at a longer CL (smaller collection angle) compared to a short CL (larger collection angle). However, the effects of combining a long CL with a small annular transmission orifice to reduce the detector collection angle are especially apparent when panel D is compared with panel D of FIG. 31. In panel D of FIG. 36, MWCNTs and the lacey carbon substrate can be differentiated, inner and outer edges are discernible in nearly every tube, and bright edges/spots are visible along the tube walls when the annular transmission profile is used to collect electrons forward-scattered only through small angles. Both mass-thickness and diffraction effects may be contributing to the bright edges/spots, but the detector mask allows one of the most basic commercially-available transmission detectors to elicit prominent, potentially meaningful contrast that cannot otherwise be obtained with current commercially available transmission detectors used in STEM-in-SEM imaging.

ADF Images Recorded Using Different Sized Transmission Orifices.

Figure 37:
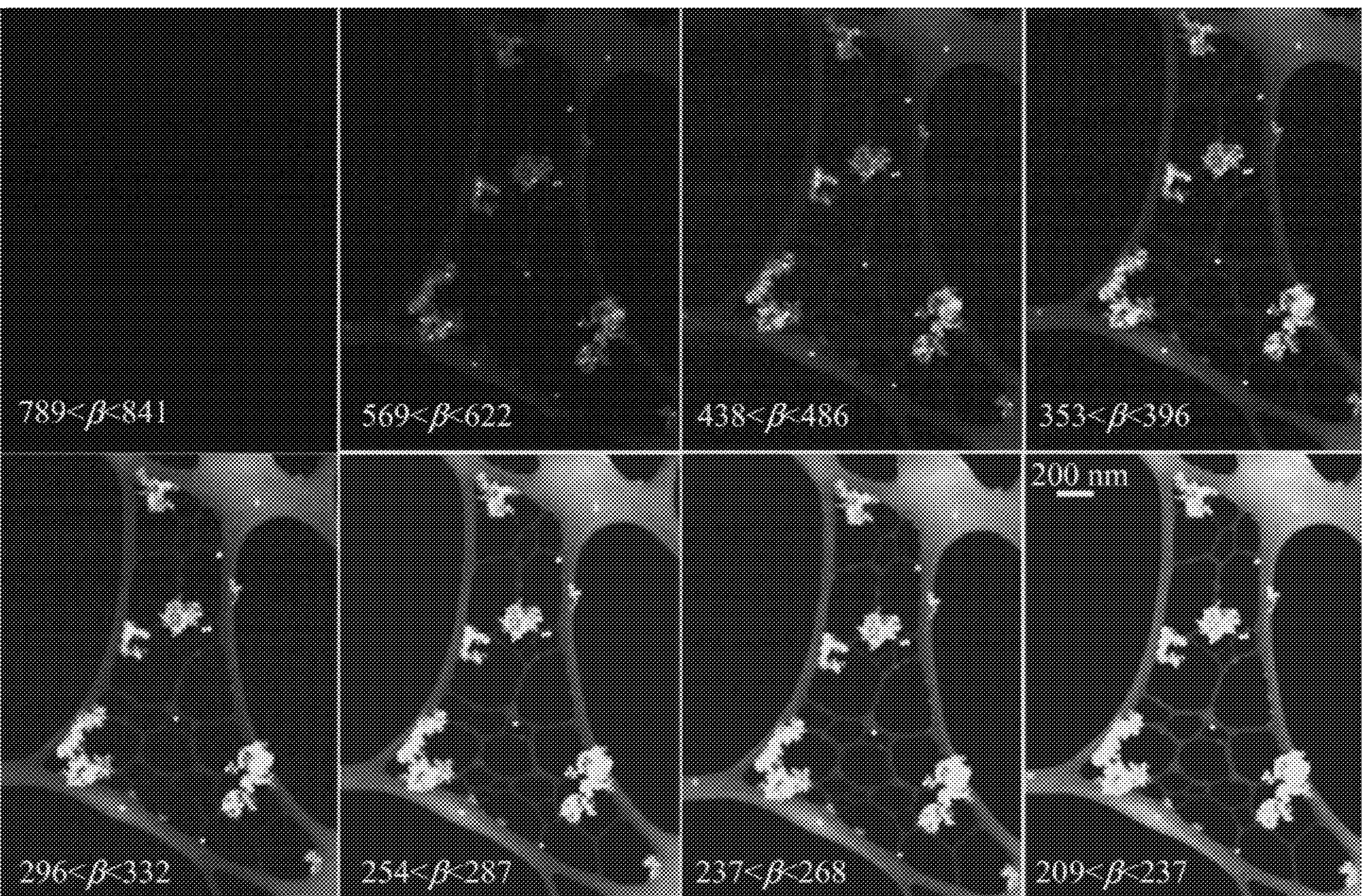
FIG. 37 shows an ADF image series showing Au and $TiO_2$ particles and agglomerates on a lacey carbon substrate recorded over a large CL range (4.6<CL<17.6 mm), wherein annular transmission orifice dimensions were $R_{Ai}$=3.5 mm and $R_{Ao}$=4 mm, and detector collection angles are inset in each image and units for β are mrad.
Figure 38:
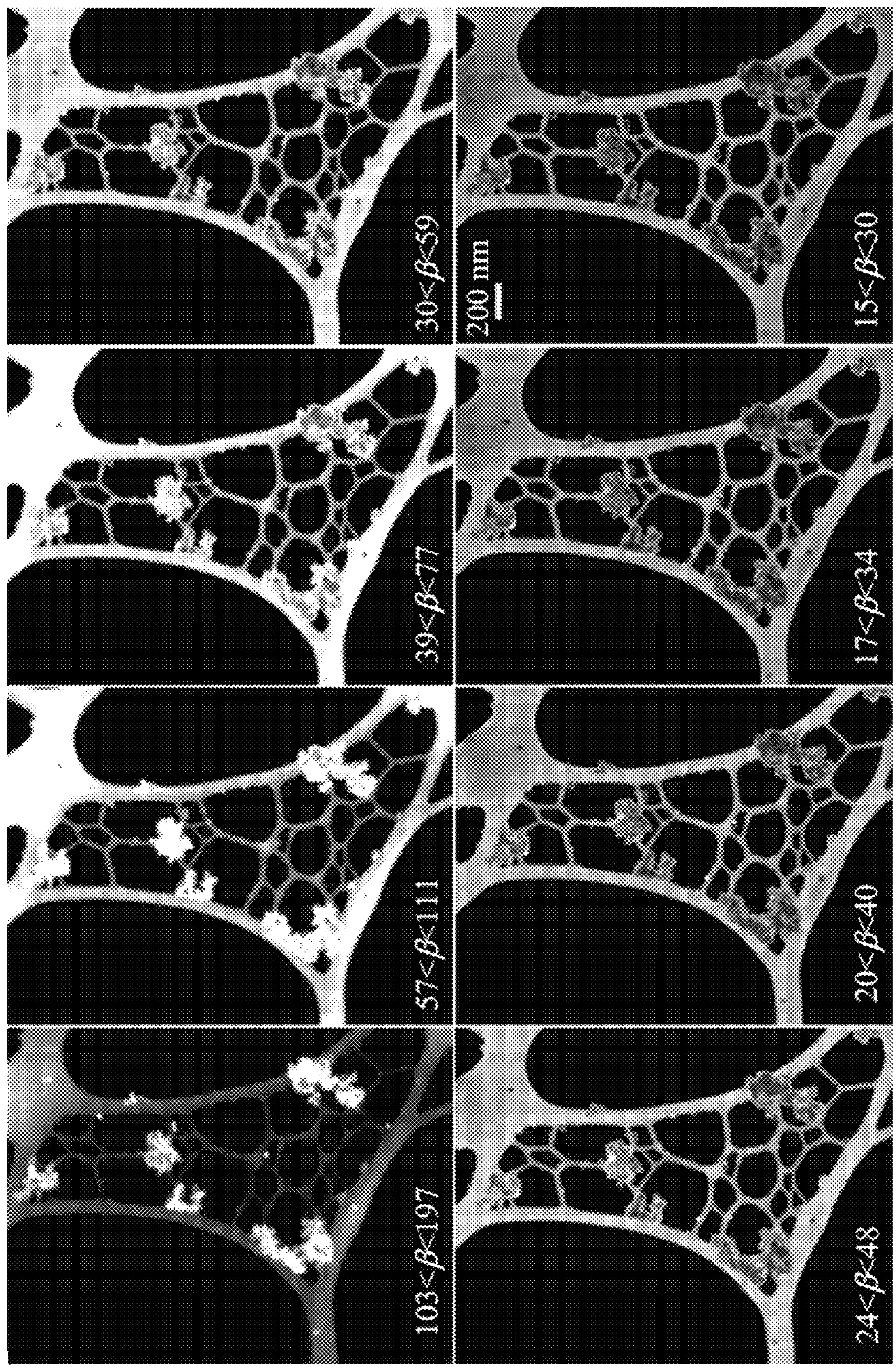
FIG. 38 shows an ADF image series showing Au and $TiO_2$ particles and agglomerates on a lacey carbon substrate recorded over a large CL range (3.5<CL<17.5 mm), wherein annular transmission orifice dimensions were $R_{Ai}$=0.25 mm and $R_{Ao}$=0.5 mm; collection half-angles are inset in each panel, and units for β are mrad.

To demonstrate the range and control over detector collection angles when the sample holder and the detector mask are used simultaneously, two image series were systematically collected using two different annular transmission profiles and are shown in FIG. 37 and FIG. 38. The sample for these images comprises 30 nm diameter Au and $TiO_2$ particles that were dispersed in ethanol and drop-cast on a lacey carbon substrate. Primary electron energy for both image sequences was 20 keV, and a 30 μm diameter condenser transmission orifice was used. FIG. 37 shows images formed using stacked plates in the detector mask, one with $R_{Ai}$=3.5 mm and another with $R_{Ao}$=4 mm, both centered on the 100 μm through-hole in the upper detector plate. FIG. 38 shows images formed with a much smaller, single plate (with transmission orifice having $R_{Ai}$=0.25 mm, $R_{Ao}$=0.5 mm) centered over one of the four diodes on the upper detector plate. Images in both series were recorded at 2 mm CL increments over similar CL ranges, and transmission detector gain settings were adjusted so that images were slightly undersaturated at the sample height where the strongest contrast between the sample and the background intensity was observed. Gain settings were not changed as the images were recorded from short to long CL. Note that although the first image of the series in FIG. 37 does not show contrast, the detector settings could have been increased to show sample contrast. In the subsequent images, contrast differences between Au and $TiO_2$ at larger collection angles could also have been enhanced by increasing the outer transmission orifice radius, and much smaller CL step sizes could have been used so that collection angle differences between images were smaller.

According to one criterion, a minimum inner collection half-angle to classify an ADF image as primarily incoherent (and therefore able to be interpreted in terms of atomic-number contrast) is $\beta_i=1.22\lambda/\Delta R$, where ΔR is the distance between neighboring atomic columns along which electrons propagate through the sample, and λ is the primary electron wavelength. For 20 keV primary electrons and ΔR=2 Å, $\beta_i \geq \sim 50$ mrad would justify incoherent imaging conditions according to this criterion. The smallest collection half-angle of the images in FIG. 37 is 209 mrad, and the ADF images meet this criterion. However, a more stringent criterion can include a larger inner collection half-angle. To avoid intra-column coherent scattering effects, the inner collection half-angle can be greater than $\beta_i=2\ \sin^{-1}[b(\lambda/z)^{1/2}]$, where b=0.61, λ is the primary electron wavelength, and z is the spacing between atoms aligned in columns parallel to the electron propagation direction. For 20 keV electrons and z=2 Å, the minimum inner collection angle should be greater than 250 mrad. Although this criterion suggests that the last two images of FIG. 37 can be classified as other than incoherent, it is reasonable to conclude that incoherent imaging conditions can be obtained with the retractable transmission detector through the use of an appropriate combination of plates with a selected transmission orifice and camera length. Depending on which criterion is used, the transmission images in FIG. 37 can be interpreted in terms of atomic-number contrast. Because of the unexpected contrast observed, complementary imaging techniques can be employed to assist with rigorous material identification.

Inner collection half-angles used to form the images of FIG. 38 are smaller than those required for definitive interpretation as Z-contrast images. A range of inner collection half-angles for the image sequence is $15 \leq \beta_i 23$ 103 mrad, and the first two images of the series meet the less stringent collection angle requirements for incoherent imaging. None of the images can be interpreted as incoherent according to the more stringent criterion described above. The image sequence of FIG. 38 also exhibits contrast changes that may make image interpretation more challenging depending on the imaging conditions. For example, in addition to the almost immediate contrast reduction exhibited by the Au and $TiO_2$ as the CL is increased, notice that the lacey carbon substrate exhibits a transition from weak contrast to strong contrast, and back to weak again. As mentioned previously, the brightness exhibited by each of the materials should pass through some maximum value as the CL is increased, and then become less bright, assuming a sufficiently long CL can be obtained. Some images also show that as the collection angles become smaller several distinct bright spots persist even though contrast from the rest of the sample becomes weaker.

Figure 39:
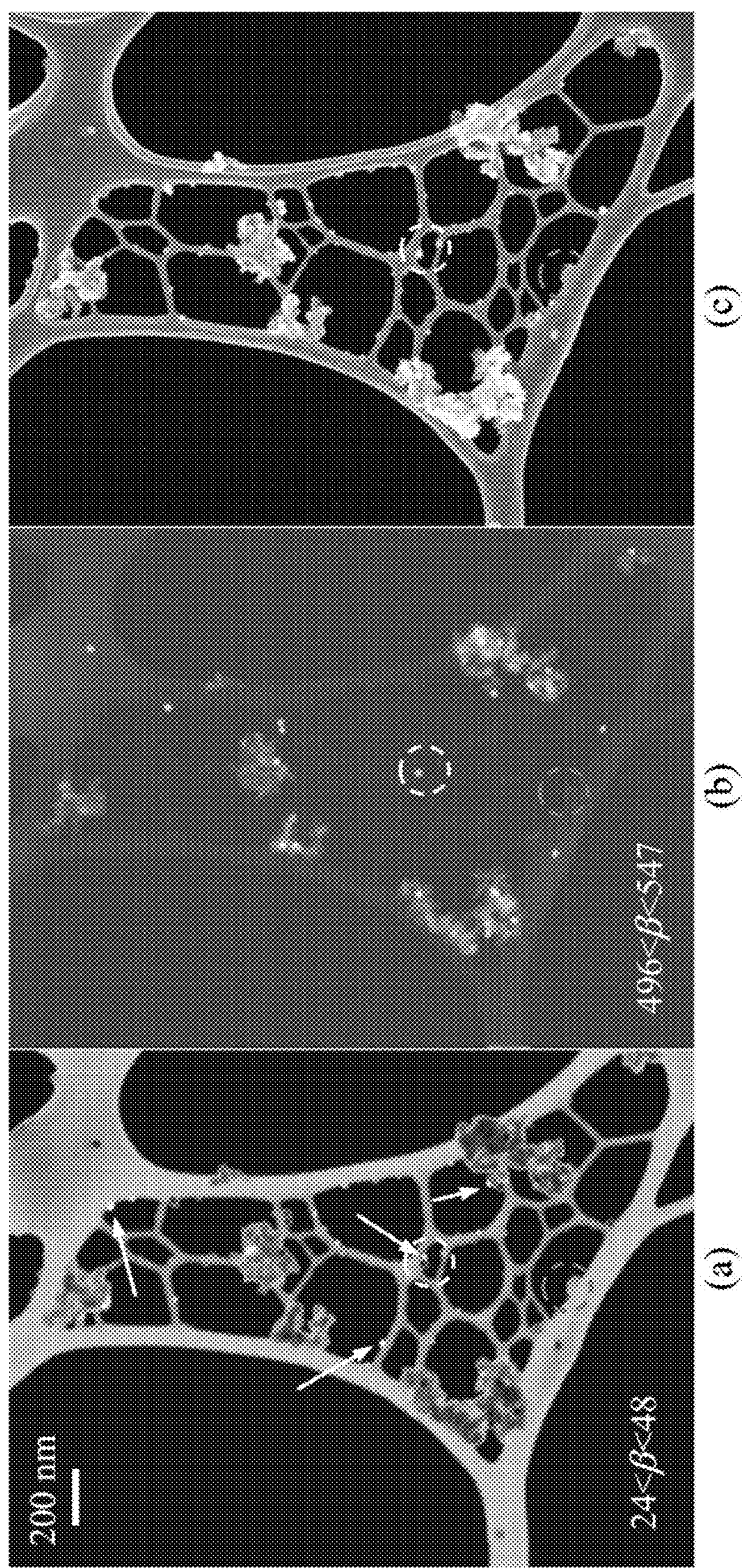
FIG. 39 shows images of Au and $TiO_2$ nanoparticles on a lacey carbon substrate, wherein panel A shows low angle ADF transmission electron images; panel B shows high angle ADF transmission electron images, and panel C shows a secondary electron image recorded with an in-lens detector at 11.8 mm working distance; ADF detector collection half-angles are inset in the images, and units for β are in mrad.

To address the persistent bright spots and material identification more thoroughly, FIG. 39 shows two images from FIG. 37 and FIG. 38 and a secondary electron image recorded with an in-lens detector. Panel A of FIG. 39 shows an ADF image ($\beta_i \approx 24$ mrad) formed with the smaller annular transmission profile located over a single diode on the upper detector plate; panel B shows an ADF image ($\beta_i \approx 496$ mrad) formed with the larger annular transmission profile, and panel C is a secondary electron image recorded simultaneously with panel B showing several large agglomerates, isolated nanop articles, and some smaller particle-like structures distributed along the edges of the lacey carbon. A distinct contrast difference exists between panels A and B, particularly the weak contrast exhibited by the large agglomerates and some of the isolated particles in panel A that represent an exaggerated example of the contrast weakening artifact exhibited in FIG. 32.

Materials comprising the agglomerates and the isolated particles can be tentatively identified based on the contrast in the HAADF image of panel B in FIG. 39. Discrete Au particles can be recognized as the spots exhibiting the strongest contrast relative to the black background. One such Au particle is located within the yellow dashed circle of panel B in FIG. 39. Since only Au, $TiO_2$, and C are present in this sample, the remaining spots exhibiting weaker contrast in panel B in FIG. 39 (see the region circled in red) can be tentatively identified as $TiO_2$ particles or agglomerates. Material assignment within the large agglomerates based only on panel B in FIG. 39 is not straightforward since thickness effects can influence image contrast. Some of the large agglomerates exhibit regions with contrast levels similar to those associated with isolated Au particles. Because agglomerate thickness is not known, definitive assignments cannot be made since a stack of $TiO_2$ particles can presumably elicit contrast similar to what a single Au particle can exhibit.

Figure 40:
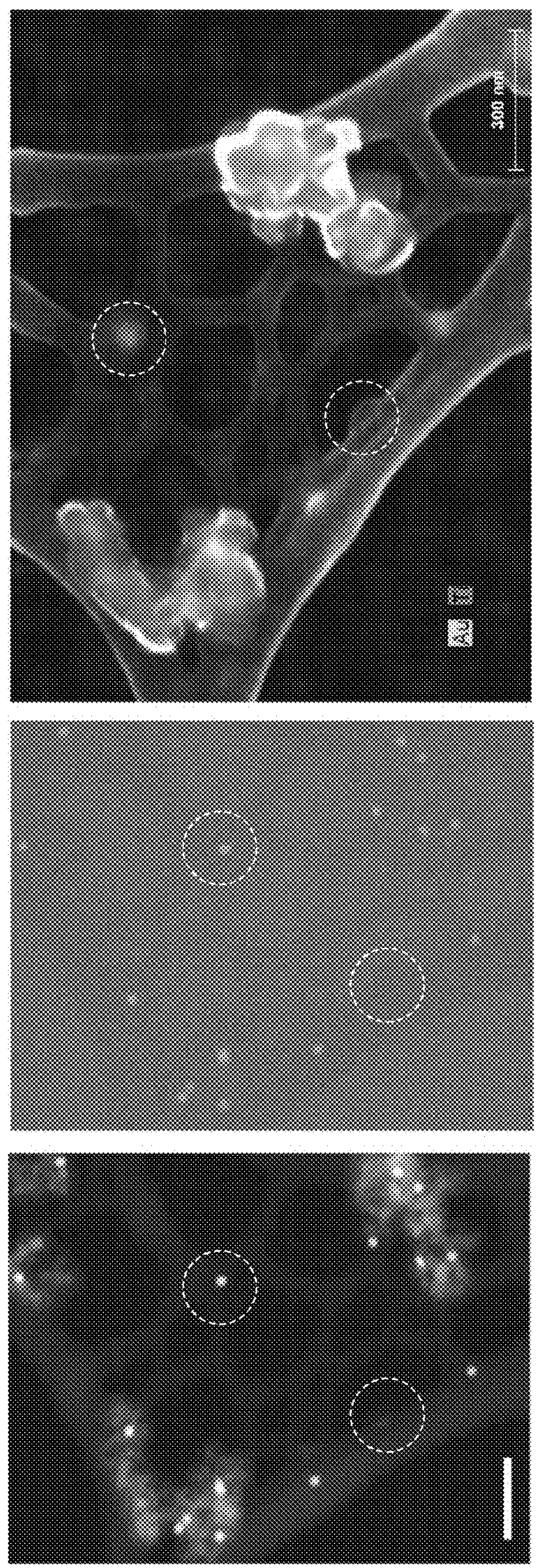
FIG. 40 shows higher magnification images of the sample shown in FIG. 38 and FIG. 39 using different detectors and slightly different imaging conditions, wherein panel A shows an ADF (βi=410 mrad) transmission electron image recorded simultaneously with panel B a backscattered electron image using a Robinson backscatter detector, and panel C shows an X-ray map overlaid on a secondary electron image showing the location of Au and Ti on the lacey carbon substrate.

Discrimination between the Au and $TiO_2$ particles in the agglomerates is provided in images shown in FIG. 40, which shows magnified regions of the images shown in FIG. 39 recorded with different detectors. Panel A of FIG. 40 shows an ADF transmission image with gain settings slightly different from those used in FIG. 37 and FIG. 39, and Panel A of FIG. 40 shows a simultaneously-recorded backscattered electron image. The same transmission profiles were used for the image in panel A of FIG. 40 as were used in panel B of FIG. 39, and the sample was positioned midway between the transmission and backscattered electron detectors (i.e., approximately 8 mm from either detector). Panel C of FIG. 40 shows an X-ray map overlaid on a secondary electron image. For reference, the yellow and red dashed circles are located in the same sample regions in FIG. 39 and FIG. 40.

The transmission and backscattered electron images of Panels A and B of FIG. 40 both show that spots (i.e., individual nanoparticles) exhibiting strong contrast with respect to the background levels occur in similar locations. The bright spots in the backscattered image of Panel B of FIG. 40 are Au particles. Since the transmission image was recorded simultaneously with the backscattered electron image, the bright spots in the transmission image are the Au particles. The transmission image shows where the Au particles reside even when they are buried within the agglomerates of $TiO_2$ particles. The X-ray map in panel C of FIG. 40 supports the material identification, wherein the green regions correspond to sample locations emitting Au Lα X-rays, and the red regions correspond to sample locations emitting Ti Kα X-rays. Au particles are immediately apparent in the X-ray map, and the particle locations match with those observed in the transmission and backscattered electron images. By process of elimination, the remaining particles should be $TiO_2$.

Material assignment to the persistent bright spots, some of which are indicated by the white arrows in panel A of FIG. 39, is not immediately clear. The particles are either $TiO_2$ or carbon. Since the collection angles are very small, the bright spots can be due to Bragg diffraction.

Example 2

Here, we demonstrate an economical way to obtain comprehensive acceptance angle control using a commercially available STEM detector with little built-in angular selectivity. A detector mask and sample holder in combination provide conventional STEM imaging modes in any SEM that includes a transmission electron detector, but is not limited to STEM-in-SEM and could be used in other microscopes and devices that select electrons or other particles (e.g., ions) scattered through different angles.

Several sample types were imaged with the detector mask. The samples included bundled single-wall carbon nanotubes (SWCNT) with catalyst particles, multi-wall carbon nanotubes (MWCNT) without catalyst particles, Au and $TiO_2$ nanoparticles, and exfoliated 2-dimensional zeolites. Mild sonication was used to disperse the carbon nanotubes and nanoparticles in different solvents (SWCNTs in chloroform, MWCNTs in n-methylpyrrolidone, and Au and $TiO_2$ particles in ethanol.) A small amount of each dispersion was drop-cast onto lacey carbon support grids and allowed to dry in air. Zeolites were deposited on an ultrathin carbon/lacey carbon substrate.

A Zeiss LEO 1525 SEM equipped with a Schottky field emission electron gun was used to image the samples at 30 kV with a 30 μm condenser transmission orifice, resulting in a spot size of 4-5 nm and a probe current ~165 pA. Detectors used here included a KE-Developments STEM detector, an Everhart-Thornley secondary electron detector, and an ETP Semra Series 8.6 Robinson backscattered electron (BSE) detector.

The new STEM detector comprises two plates (see panel A of FIG. 41); an upper detector plate for DF imaging with four rectangular diodes surrounding a 100 μm diameter through-hole and a lower detector plate with a diode for BF imaging positioned under the through-hole. The angular selectivity built into this detector is minimal, and acceptance angle adjustments must be obtained through changes in CL, defined here as the distance between the sample and the detector diode. The STEM detector also has an xyz-positioning stage to align the diodes with the optic axis. This detector positioning feature can also be used to elicit unconventional and potentially useful image contrast.

One step towards comprehensive acceptance angle control involves moving the detector to an appropriate distance from the pole piece. For example, when the transmitted electron detector is at its lowest position as shown in panel B of FIG. 41, the distance between the top of the detector and the bottom of the pole piece is ~20 mm, thereby maximizing the available CL and space for positioning the sample. When the transmitted electron detector is set at its highest position, the distance between the detector and pole piece is ~10 mm.

Figure 41:
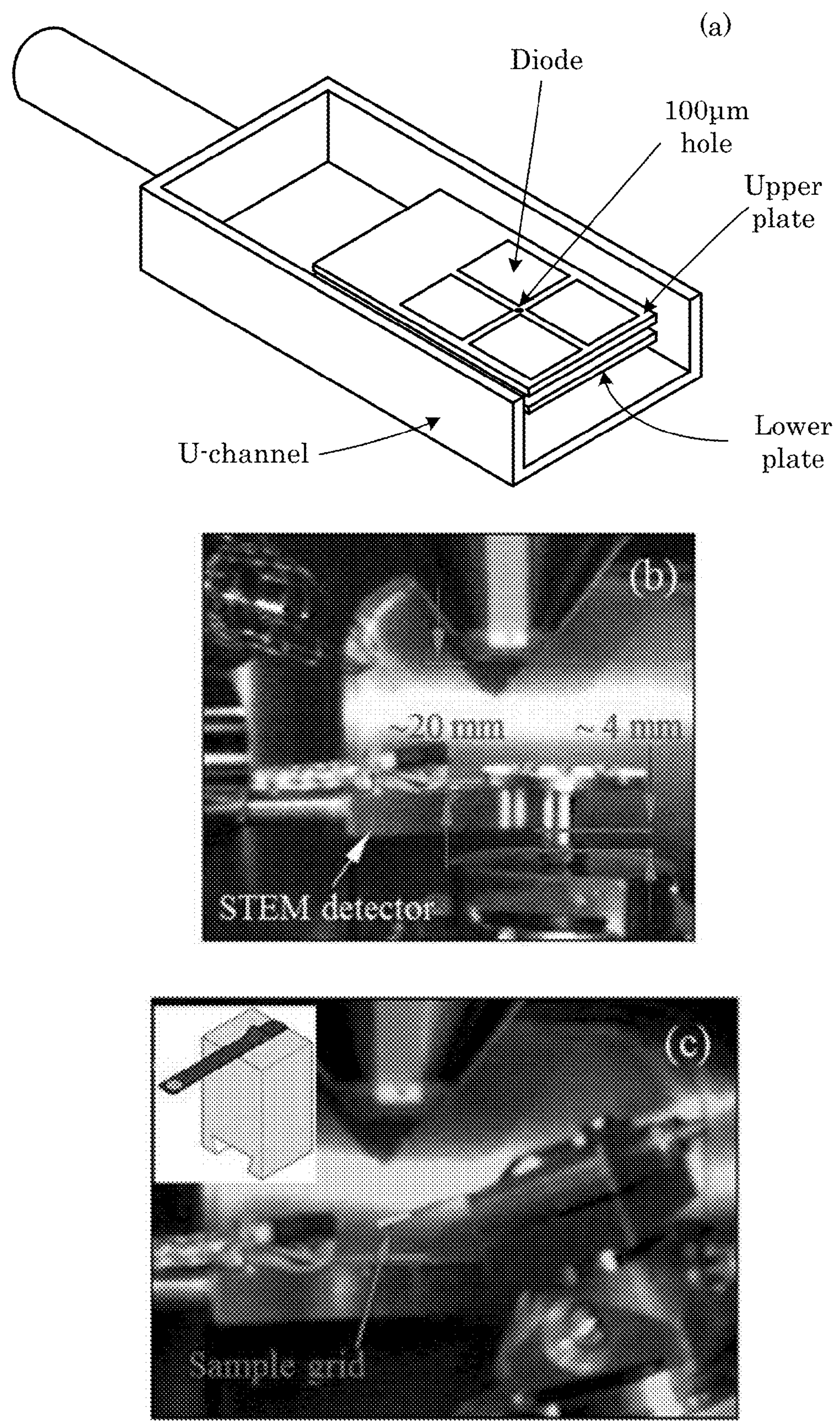
FIG. 41 shows a STEM detector according to Example 2 including a diode geometry and layout in panel A; panel B shows an interior view of the SEM chamber showing the detector at its lowest position with a carousel style holder, and panel C shows an interior view of the SEM chamber showing a sample holder for positioning a sample at arbitrary orientation in which the inset shows the sample holder.

A sample holder shown in panel C of FIG. 41 is used to hold a sample and position the sample relative to the pole piece and detector. In addition to allowing precise sample positioning, the cantilever arm of the sample handle can be very thin and provide the sample to be located almost anywhere in the vacant space between the STEM detector and pole piece. Thin flexible cantilever arms also provide an improved measure of instrument protection; damage to the pole piece or other detectors is unlikely since the cantilever arm deflect if contact occurs. With the sample holder, samples are not limited to 3 mm foils/substrates; the cantilever arms engage the edge of a self-supporting sample of arbitrary shape. Engaging the sample in this manner minimizes sample holder shadowing effects.

Acceptance angle ranges of the detector are improved by switching from a carousel-style holder to the sample holder described herein and using the 20 mm of CL available when the detector is at its lowest position. The acceptance half-angle range available for BF imaging with the existing 100 μm through-hole and the carousel-style holder is $\sim 10<\beta<25$ mrad. Substitution of the sample holder herein provides a BF range of $\sim 2.5<\beta<50$ mrad. For DF imaging with the carousel-style holder, the acceptance half-angle range is $\sim 85<\beta<1270$ mrad. Using the sample holder herein holder expands that range to $\sim 20<\beta<1420$ mrad. The minimum inner acceptance half-angle ($\beta_i \approx 20$ mrad) is due to a small gap between the diodes and the 100 μm through-hole. However, when a single diode is used, β can be much smaller than 20 mrad, thereby enabling marginal and annular BF imaging.

The detector mask includes a support frame and a plate with transmission orifice (e.g., as shown in FIG. 14) that can be accommodated by most commercially available STEM detectors. The sample holder shown in panel B of FIG. 26 provides positioning the sample at an arbitrary orientation with respect to the plates of the detector mask and detector.

Figure 42:
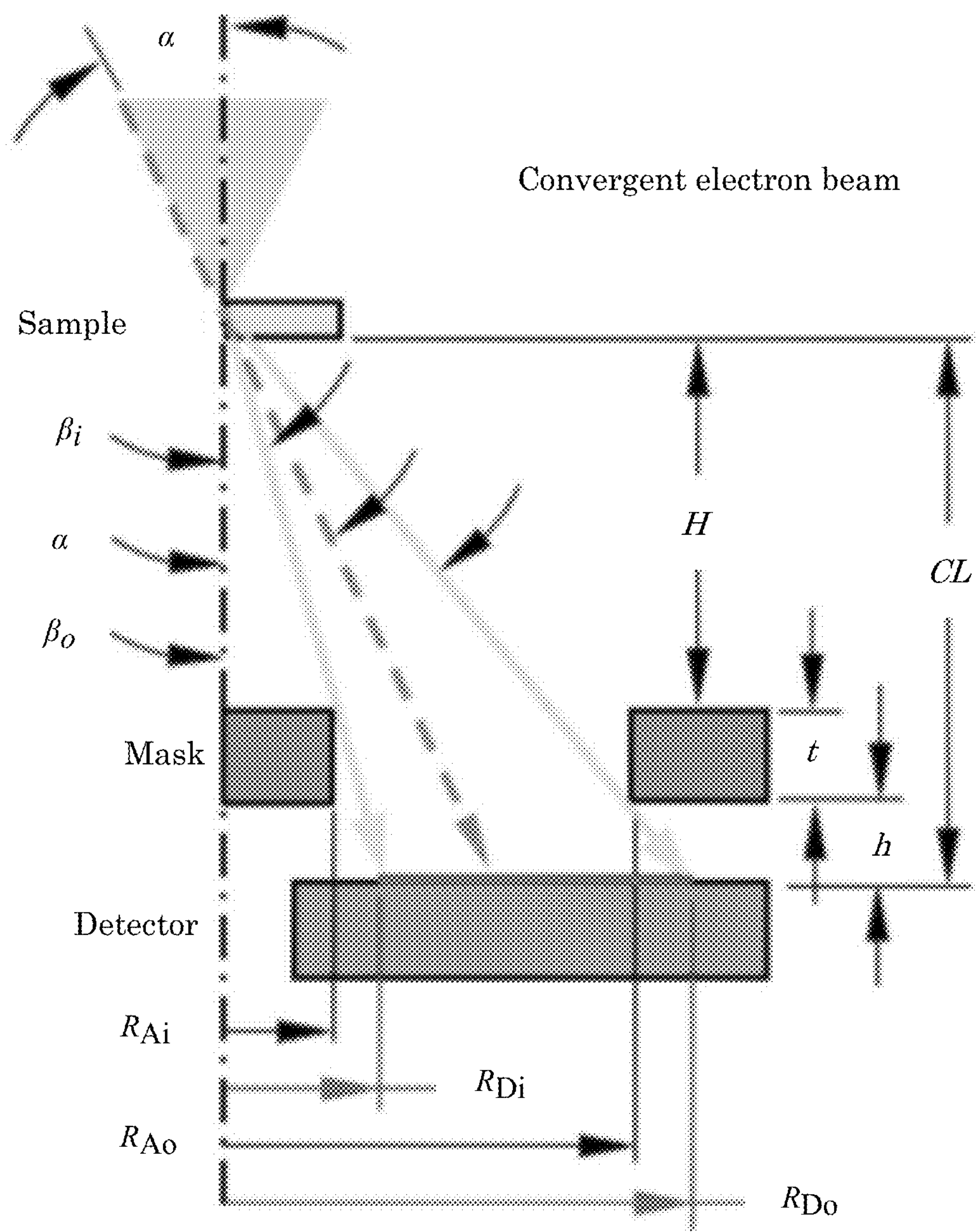
FIG. 42 shows parameters and electron trajectories for providing signal collection modes, wherein working distance WD is a distance between a sample and a pole piece (not shown); panel B shows two plates stacked in the detector mask to obtain an annular transmission profile with different inner and outer radii, and panel C shows several imaging modes with different plates positioned over each of four STEM detector diodes.

Table 1 lists signal collection modes. Angles involved in the signal collection modes are shown in FIG. 42, wherein the optic axis and a detector mask centered over a single or multiple diodes can be implemented by using plates for the detector mask in different ways. For example, a variable-annulus transmission profile can be implemented by stacking plates with different transmission orifices as shown in FIG. 18A. The plate on the upper left can be used alone to exclude small-angle scattering from DF images or can be stacked with the plate on the upper right to admit electrons scattered through a specific angular range. BF imaging can be implemented with the lower detector plate by including a small transmission orifice in the center of the plates.

TABLE 1

| STEM-in-SEM Signal Collection Mode | Acceptance Angle Range |
| --- | --- |
| Bright-Field (BF) | $\beta_i = 0$, $\beta_o < \alpha$ |
| Annular Bright-Field (ABF) | $0 < \beta_i$, $\beta_o < \alpha$ |
| Marginal Bright-Field (MBF) | $\beta_i \approx \alpha$, |
| Thin Annular Detector (TAD) | $\beta o \approx 1.1\beta\iota$ |
| Low Angle Annular | $\beta_i > \alpha$ |

TABLE 1-continued

| STEM-in-SEM Signal Collection Mode | Acceptance Angle Range |
|---|---|
| Dark-Field (LAADF)* | $\beta_o \leq 50$ mrad |
| Medium Angle Annular Dark-Field (MAADF)* | $\beta_i > 50$ mrad<br>$\beta_o < 100$ mrad |
| High Angle Annular Dark-Field (HAADF)* | $\beta_i \geq 100$ mrad |

*LAADF, MAADF, and HAADF distinctions are somewhat arbitrary, and the ranges provided are typically associated with high-energy STEM. Because lower-energy electrons scatter more strongly, these values will be somewhat higher for STEM-in-SEM.

The four rectangular detector diodes provide utility when combined with an xyz-positioning stage. For example, if the detector positioning stage aligns individual diodes with the optic axis, each of those diodes can be used for different imaging modes when appropriate transmission profiles are employed. An advantage to locating transmission orifices over individual detector diodes is very small acceptance angles can be selected. In this way, the detector mask enables signal collection modes beyond basic BF and DF imaging (Table 1): BF imaging with transmission orifices other than the existing 100 μm through-hole, annular bright-field imaging, thin annular detection schemes, marginal bright-field imaging in which a thin annular detector collects electrons scattered into acceptance angles straddling the beam convergence angle, as well as annular DF imaging at low, medium, and high angles.

Figure 43:
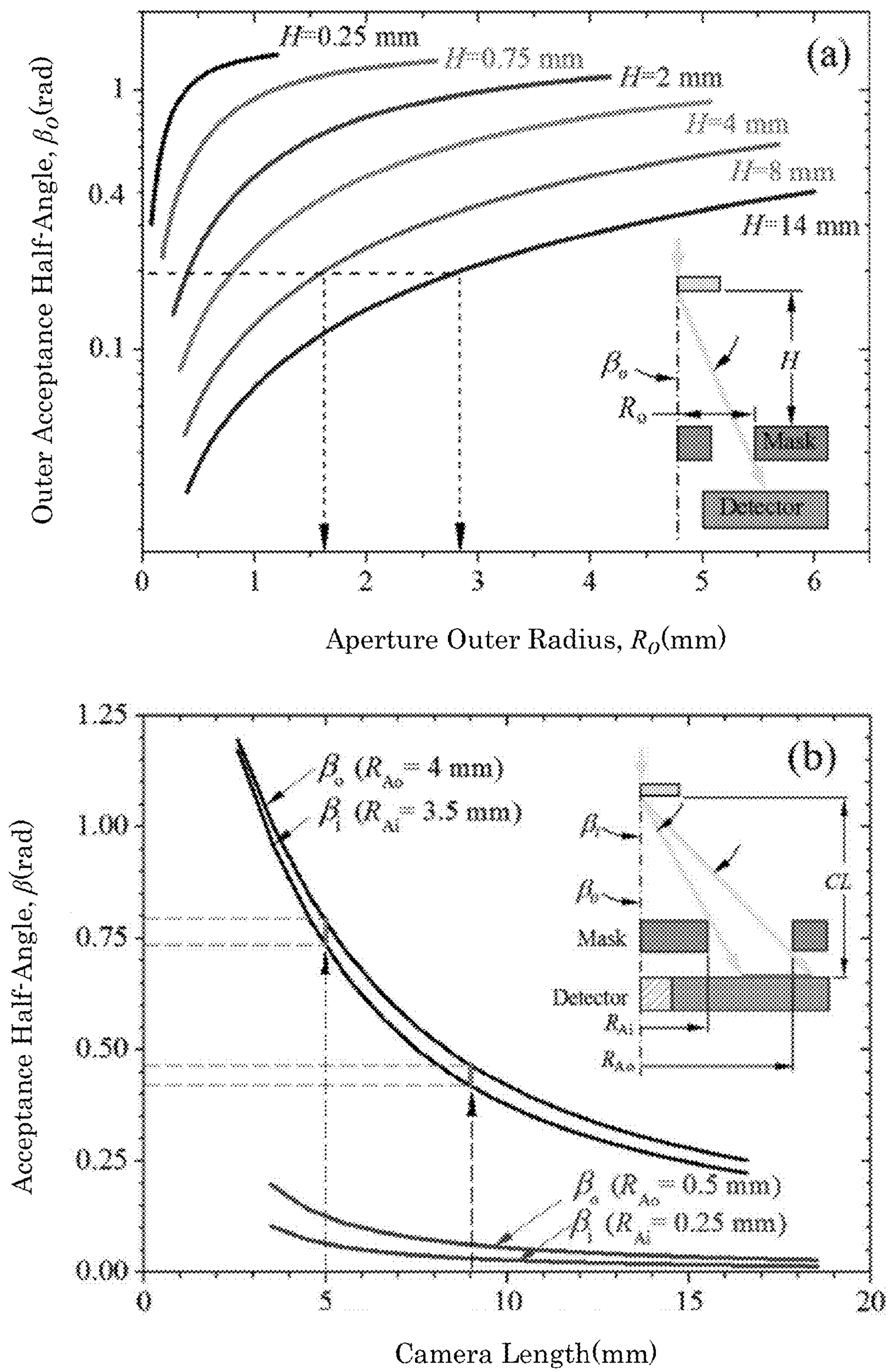
FIG. 43 shows, in panel A, a graph of outer acceptance angle versus transmission orifice outer radius, and panel B shows a graph of acceptance half-angle versus camera length.

Selecting and implementing specific signal collection modes is straightforward with the detector mask. The basic procedure is to choose a mask with specific transmission orifice dimensions and then use the SEM sample positioning stage to adjust the CL and admit electrons scattered into desired acceptance angle ranges. For example, panel A of FIG. 43 shows how $\beta_o$ varies with transmission orifice radius $R_o$ and H, the sample-to-mask distance. Note that CL=H+t+h, where t is the mask thickness, and h is the mask-to-detector distance. As the figure indicates, $\beta_o$=200 mrad can be obtained using all four diodes with different transmission orifices (i.e., with $R_o \approx 1.6$ mm and H=8 mm, or with $R_o \approx 2.8$ mm and H=14 mm). Acceptance angles can also be shifted around the desired values by using the sample positioning stage to change the CL. Panel B of FIG. 43 shows how two different annular transmission orifices can enable thin annular detector configurations to select electrons scattered through different angles. The black lines encompass acceptance angles accessible with a large transmission orifice (inner radius $R_{Ai}$=3.5 mm, outer radius $R_{Ao}$=4 mm) centered over all four diodes, the blue lines encompass acceptance angles accessible with a smaller transmission orifice ($R_{Ai}$=0.25 mm, $R_{Ao}$=0.5 mm) located over a single diode. As the figure indicates, a large acceptance angle range can be accessed with only two transmission orifices and ~20 mm of CL. Although the difference between inner and outer angles changes somewhat as the CL is changed, the angular selectivity that the detector mask provides is apparent, especially when considering that the SEM sample stage can adjust the CL in very small increments.

Detector masks having plates with transmission orifices can be fabricated several ways. One process for making the plate is to cut, poke, or scratch a transmission orifice having a selected transmission profile in a piece of metal foil (e.g., aluminum foil) and dispose the foil with the transmission orifice over the detector. The plates can also be machined on a substrate to provide the detector mask plates that having transmission orifices of varying transmission profiles. Additionally, the plates can be photoetched or otherwise precisely manufactured.

Results for Multi-Wall Carbon Nanotubes.

Figure 44:
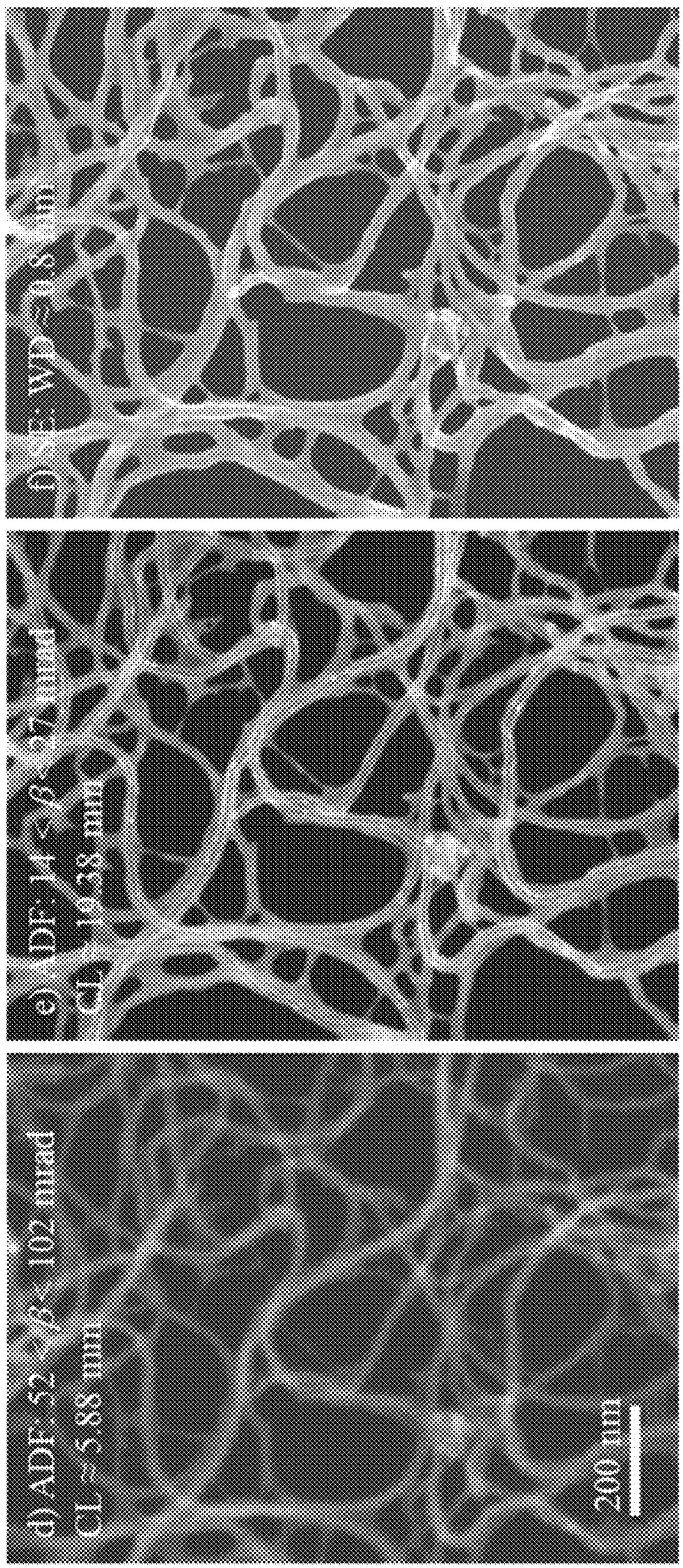
FIG. 44 shows micrographs of MWCNTs in residual organic solvent imaged with different detectors in which BF STEM images were recorded using a detector mask with a 20 μm diameter aperture, and DF STEM images were taken using a detector mask with an annular aperture ($R_{Ai}$=0.25 mm, $R_{Ao}$=0.5 mm) centered over a single diode, wherein panel A is a BF image (CL=3.75 mm, WD=18.2 mm); panel B is a BF image (CL=19.75 mm, WD=1.9 mm); panel C is an SE image (WD=1.9 mm); panel D is an ADF image (CL=5.88 mm, WD=14.2 mm); panel E is an ADF image (CL=19.38 mm, WD=0.8 mm), and panel F is an SE image (WD=0.8 mm)

FIG. 44 shows two examples of how the detector mask and the large CL can be used to reveal different information. Both image sets in this figure show multi-wall carbon nanotubes (MWCNTs) in residual n-methylpyrrolidone. Panels A and B in FIG. 44 show BF images recorded using a mask with a 20 μm diameter transmission orifice, and panel C of FIG. 44 shows a conventional secondary electron (SE) image. Panels D and E of FIG. 44 show annular dark-field (ADF) images recorded using a detector mask with an annular transmission orifice ($R_{Ai}$=0.25 mm, $R_{Ao}$=0.5 mm) centered over one of the STEM detector diodes, and panel F of FIG. 44 shows a conventional SE image recorded simultaneously with panel E of FIG. 44. Individual nanotubes are discernable in panels A and B. In panel B, however, bends and other deformations along many tubes can be observed, and inner and outer tube diameter measurements are feasible. Tubes are discernable in panel C, but diameter measurements are not feasible because of the residual solvent. In panels D and F, many MWCNTs are visible but they are difficult to differentiate from the residual solvent. Nanotubes in panel E, however, can be differentiated from solvent because bright lines delineate the MWCNTs. Angle $\beta_i$=14 mrad is sufficiently small to capture Bragg-scattered electrons, and the bright lines may be due to diffraction.

Results for Au and $TiO_2$ Particles on Lacey Carbon.

Figure 45:
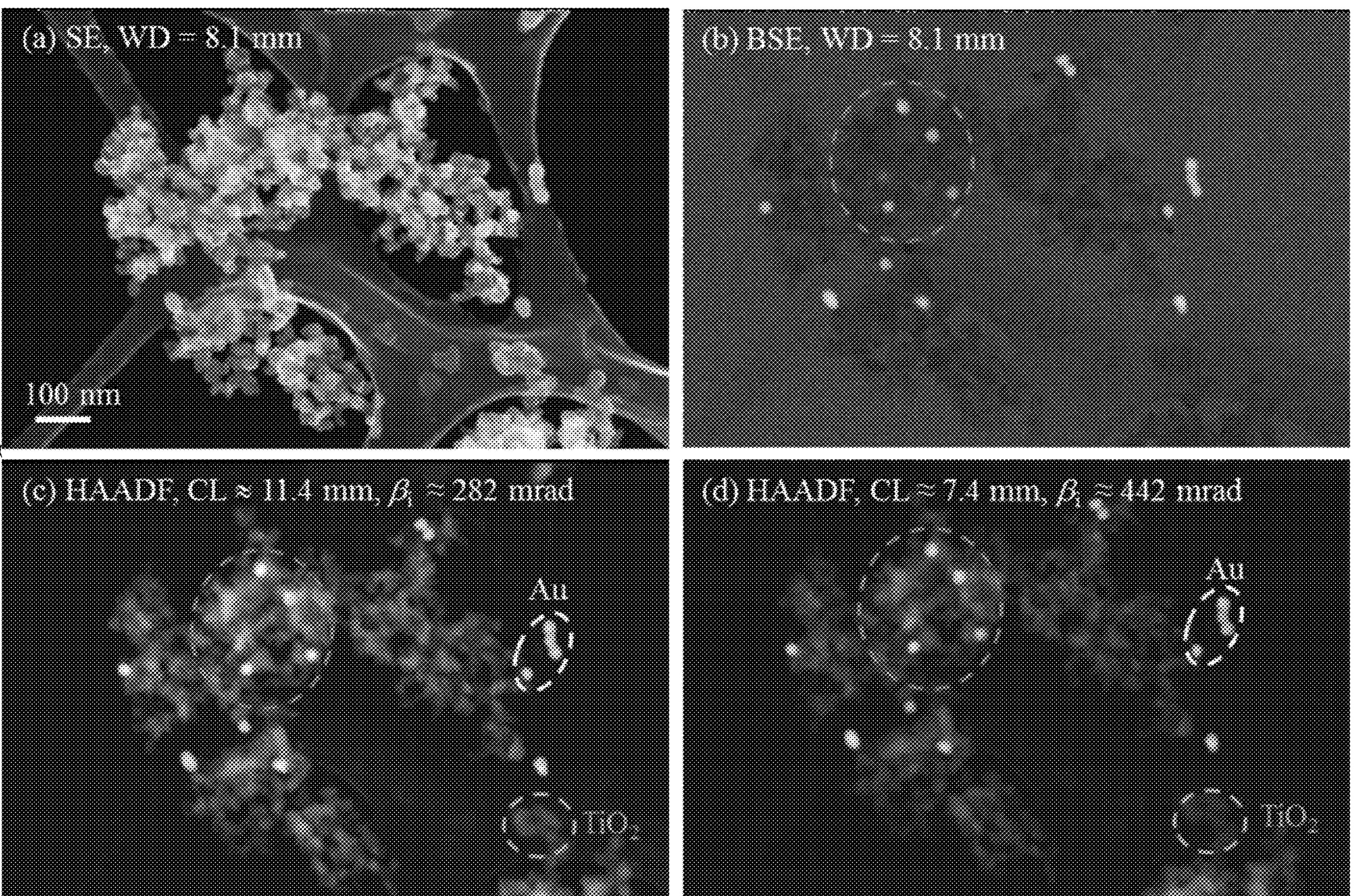
FIG. 45 shows Au and $TiO_2$ particles on lacey carbon imaged with different detectors, wherein panel A is an SE image (WD=8.1 mm); panel B is a BSE image (WD=8.1 mm); panel C is an HAADF STEM image ($R_{Ai}$=3 mm, CL=11.4 mm, WD=8.1 mm); panel D is an HAADF STEM image ($R_{Ai}$=3 mm, CL=7.4 mm, WD=12.1 mm), and STEM detector gain settings were unchanged for the images shown in panel C and panel D.

FIG. 45 shows images of Au and $TiO_2$ particles on a lacey carbon substrate recorded using the SE detector (panel A), the BSE detector (panel B), and the STEM detector in HAADF mode (panels C and D). The STEM images were collected using the same gain settings at CL≈11.4 mm (panel C) and CL≈7.4 mm (panel D). The STEM and BSE images both show Z-contrast information complementary to the SE image in that isolated Au particles can be discerned from isolated $TiO_2$ particles. Although the BSE image shows the Au particles as bright spots, the STEM images simultaneously show the Au particles (four of which are circled in yellow) and the $TiO_2$ particles which are generally less bright.

Depending on the acceptance angles and the sample, STEM image contrast interpretation may or may not be straightforward because a sufficiently large agglomerate of $TiO_2$ particles can elicit the same mass-thickness contrast as a single Au particle. This effect can be observed in the HAADF (Z-contrast) image of panel C of FIG. 45. Within the red dashed circle several regions of strong contrast are visible (both Au and $TiO_2$). The contrast is not particularly amenable to direct visual interpretation. However, panel D of FIG. 45 shows that by moving the sample closer to the STEM detector (i.e., reducing the CL) the acceptance angle increases, and the contrast between the Au particles and the $TiO_2$ particles increases. The persistent bright spots can be assigned to the Au particles.

Results for Catalyst Particles in Bundled Carbon Nanotubes.

Figure 46:
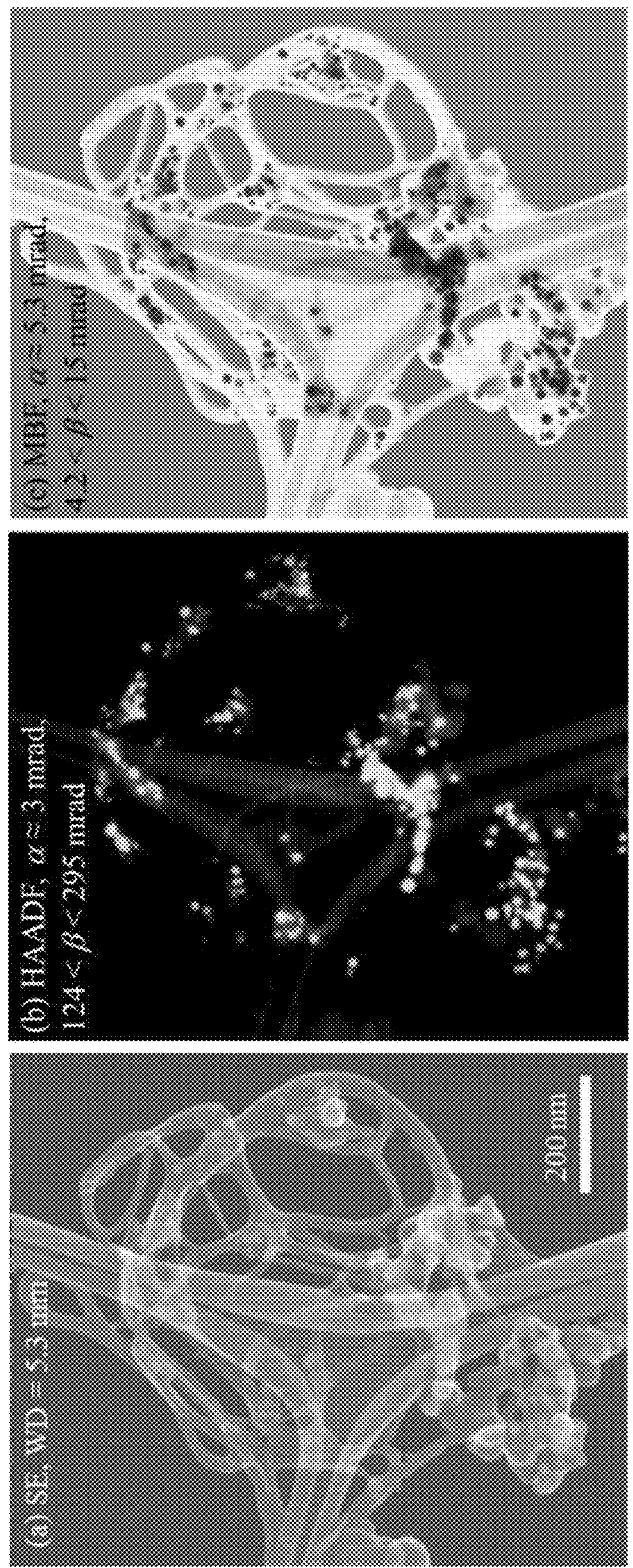
FIG. 46 shows SWCNT bundles with metal catalyst particles and amorphous carbon imaged with an SE detector (panel A), in HAADF STEM mode (panel B, aperture $R_{Ai}$≈0.5 mm and $R_{Ao}$≈1.25 mm), and in marginal BF STEM mode (panel C, aperture $R_{Ai}$≈60 μm and $R_{Ao}$≈0.22 mm.

Combining small transmission orifices and long CLs to mix BF and DF signals can elicit useful contrast. FIG. 46 shows different ways to discriminate metal catalyst particles from carbon in a highly bundled SWCNT sample. Although some catalyst is visible in the SE image (panel A of FIG. 46), the HAADF STEM image (panel B of FIG. 46) directly reveals the catalyst particles as the bright spots. The amorphous carbon and SWCNT bundles, however, are generally not visible. In the marginal BF image (panel C of FIG. 46), residual catalyst and amorphous carbon, SWCNT bundles, and the carbon substrate can all be observed simultaneously, and the image features are generally sharper than those in panels A and B of FIG. 46. The catalyst particles appear dark in the marginal BF image because the STEM detector transmission orifice only admits electrons scattered into acceptance angles between ~4 and 15 mrad.

Regions of the sample with greater mass-thickness can appear darker than regions with lesser mass-thickness. In this instance, the metallic catalyst particles scatter a significant fraction of electrons through angles larger than 15 mrad. Therefore, the signal due to the catalyst will be weak and the particles will appear dark compared to the rest of the image. Scattering angles associated with the carbon are generally more shallow, and therefore a large fraction of the signal is collected resulting in brighter regions in the image. The image background exhibits a moderate level of contrast because electrons in the outer fringe of the incident illumination cone (i.e., primary electrons with incident angles between 4.2 and 5.3 mrad) are able to pass through the transmission orifice and be collected by the STEM detector. Despite the unconventional contrast, discerning the different phases in panel C of FIG. 46 is still straightforward.

Results for Exfoliated 2D Zeolite Sheets.

Figure 47:
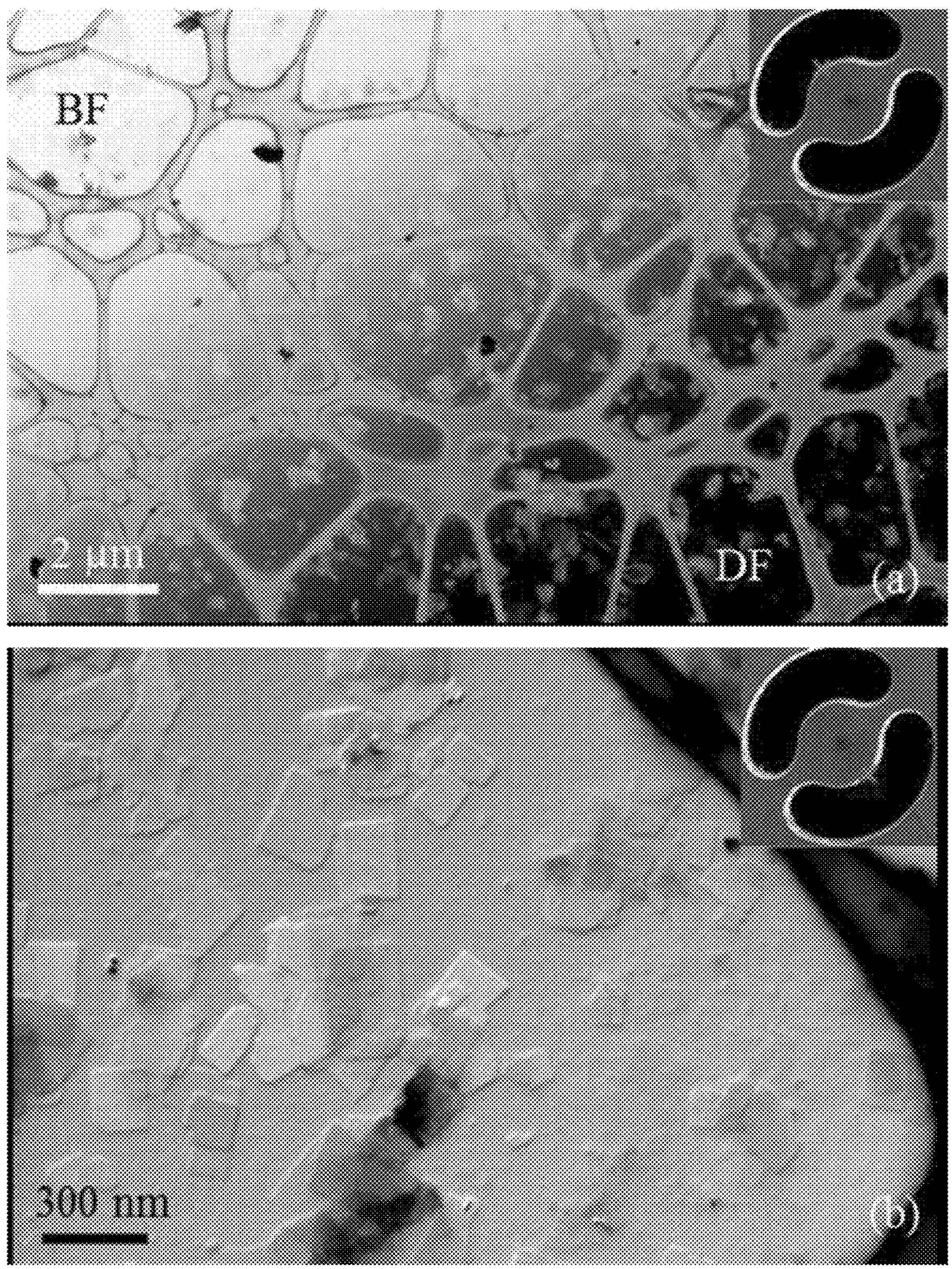
FIG. 47 shows STEM images of 2D exfoliated zeolites with the optic axis positioned at the edge of a small ADF aperture ($R_{Ai}$=0.25 mm, $R_{Ao}$=0.5 mm), wherein panel A shows an image simultaneously showing BF and DF regions and the transition region between the two, and panel B shows an image of the sample in the transition region, wherein red markers in the insets indicate the optic axis position on the transmission orifice.

Another way BF and DF signals can be mixed is by moving the STEM detector laterally with respect to the optic axis. FIG. 47 shows STEM images of ~3 nm-thick exfoliated zeolite sheets on an ultra-thin carbon/lacey carbon substrate. Here, the detector was moved so the optic axis intersected the edge of a small ADF transmission orifice ($R_{Ai}$=0.25 mm, $R_{Ao}$=0.5 mm) at the point indicated by the red '×' in the insets. Panel A of FIG. 47 shows both BF and DF regions, as well as the transition between them. Panel B of FIG. 47 shows a higher magnification image of the transition region. The image is different from conventional STEM images in that it appears to show topographic information.

By using the SEM sample positioning stage to change the CL, the working distance (WD) changes to maintain focus at the sample. As the WD changes to maintain focus at the sample, the beam convergence angle also changes. For the SEM used here, the beam convergence half-angle can be reasonably estimated as $\alpha \approx 2.53 D_a/(WD+9)$, where $D_a$ is the beam condenser transmission orifice diameter, and WD is the working distance (both with mm units). The 30 μm condenser transmission orifice used here, combined with the ~1-20 mm CL, enables $\sim 2.6 < \alpha < \sim 7.5$ mrad. This can be advantageous in a microscope that does not directly enable beam convergence angle control: more parallel illumination can be obtained by employing a long WD or a smaller beam condenser aperture, and more convergent illumination can be obtained by using a short WD or a larger beam condenser transmission orifice. Small-angle coherent scattering (i.e., that due to Bragg diffraction) can be collected in ADF imaging mode by using a long WD, a small beam condenser transmission orifice, and a small STEM detector transmission orifice. Higher-angle incoherent scattering (i.e., scattering that contributes to Z-contrast) can be collected by employing a short WD, a larger beam condenser transmission orifice, and a HAADF STEM detector transmission orifice with a large inner radius. Image contrast can depend on the combination of sample, STEM detector, primary electron beam condenser transmission orifices, WD, CL, and primary electron energy. If the effects of changing beam convergence angle are not desired for a particular experiment, then the sample can be held stationary and the STEM detector xyz-positioning stage can be used to change the CL by ~10 mm.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A sample holder to hold a sample for microscopy or spectroscopy comprising:

a basal member;

an inferior cantilever arm disposed on the basal member to receive the sample and comprising:

a first mount end proximately attached to the basal member; and a first free end disposed distal to and protruding away from the basal member, the first free end being flexible relative to the first mount end; and a superior cantilever arm disposed on the basal member opposing the inferior cantilever arm such that the inferior cantilever arm is interposed between the basal member and the superior cantilever arm, the superior cantilever arm comprising:

a second mount end proximately attached to the basal member;

a second free end disposed distal to and protruding away from the basal member, the second free end being flexible relative to the second mount end; and a curved intermediate armlet interposed between the second mount end and the second free end, the curved intermediate armlet comprising a depressible crook in which the depressible crook is in a relaxed position when not depressed, and the depressible crook is in a stretched position when depressed, wherein the first free end and the second free end opposingly engage and retain the sample between the first free end and the second free end when the depressible crook is in the relaxed position, and the first free end is spaced apart from the second free end to release or to receive the sample between the first free end and the second free end when the depressible crook is in the stretched position.

2. The sample holder of claim 1, further comprising:

a first eyelet disposed on the first free end; and a second eyelet disposed on the second free end, wherein the first eyelet and the second eyelet provide exposure of a portion of the sample to a plurality of probe particles.

3. The sample holder of claim 1, wherein the basal member comprises a mating member to attach the sample holder to a microscope sample manipulator.

4. A scope system comprising:

the sample holder of claim 1 to receive the sample and to expose the sample to a plurality of source particles such that the probe particles are communicated from the sample in response to receipt of the source particles; and a detector mask to transmit selectively a plurality of probe particles to a particle detector, the detector mask comprising:

a plate comprising a plate wall disposed in the plate and enclosing a transmission orifice arranged in a transmission profile to:

transmit probe particles having a trajectory coincident with the transmission orifice, block probe particles having a trajectory external to the transmission orifice, and form a probe particle beam comprising the probe particles transmitted by the transmission orifice to the particle detector, wherein the transmission profile of the detector mask comprises a sector, a semi-circle, an annular sector, or a combination comprising at least one of the foregoing first transmission profiles, and the first plate of the detector mask receives the probe particles from the sample held by the sample holder.

5. The scope system of claim 4, further comprising:

a particle detector to detect the probe particles in the probe particle beam.

6. The detector mask of claim 4, further comprising a support on which the plate is disposed.

7. The detector mask of claim 4, wherein the support mounts on the particle detector.

8. The detector mask of claim 4, wherein the transmission profile further comprises:

a bright field transmission profile;

a dark field transmission profile;

an annular dark field transmission profile;

a low-angle annular dark field transmission profile;

a medium angle annular dark field transmission profile;

a high angle annular dark field transmission profile;

an annular bright field transmission profile; or a combination comprising at least one of the foregoing transmission profiles.

9. The detector mask of claim 4, wherein the plate is segmented into a plurality of quadrants in which the quadrants independently comprise transmission orifices having independent transmission profiles comprising:

a circle, a sector, a semi-circle, an annular sector, a rectangle, or a combination comprising at least one of the foregoing first transmission profiles.

10. The detector mask of claim 4, wherein the plate is segmented into a plurality of sectors in which the sectors independently comprise transmission orifices having independent transmission profiles comprising:

a circle, a sector, a semi-circle, an annular sector, a rectangle, or a combination comprising at least one of the foregoing transmission profiles, the sectors being distributed azimuthally about a center of rotation of the plate.

* * * * *